(12) United States Patent
Matsuda et al.

(10) Patent No.: US 9,187,554 B2
(45) Date of Patent: Nov. 17, 2015

(54) METHOD FOR SECRETORY PRODUCTION OF PROTEIN

(71) Applicant: AJINOMOTO CO., INC., Tokyo (JP)

(72) Inventors: Yoshihiko Matsuda, Kanagawa (JP); Hiroshi Itaya, Kanagawa (JP); Yoshimi Kikuchi, Kanagawa (JP); Haruki Beppu, Kanagawa (JP); Jurgis Antanas Vladovich Jomantas, Moscow (RU); Ekaterina Aleksandrovna Kutukova, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 78 days.

(21) Appl. No.: 14/264,353

(22) Filed: Apr. 29, 2014

(65) Prior Publication Data

US 2014/0255996 A1    Sep. 11, 2014

Related U.S. Application Data

(63) Continuation of application No. PCT/JP2012/078906, filed on Nov. 1, 2012.

(30) Foreign Application Priority Data

Nov. 2, 2011 (JP) ................................. 2011-240745
Nov. 2, 2011 (RU) ............................... 2011144497

(51) Int. Cl.
    C07K 16/00    (2006.01)
    C07K 16/34    (2006.01)
    C12N 15/77    (2006.01)
    C07K 14/34    (2006.01)

(52) U.S. Cl.
    CPC ............... *C07K 16/00* (2013.01); *C07K 14/34* (2013.01); *C12N 15/77* (2013.01)

(58) Field of Classification Search
    None
    See application file for complete search history.

(56) References Cited

U.S. PATENT DOCUMENTS

| | | |
|---|---|---|
| 4,965,197 A | 10/1990 | Liebl et al. |
| 6,027,920 A | 2/2000 | Joliff et al. |
| 7,252,972 B2 | 8/2007 | Kikuchi et al. |
| 7,323,321 B2 | 1/2008 | Rayapati et al. |
| 7,635,579 B2 | 12/2009 | Rayapati et al. |
| 7,723,097 B2 | 5/2010 | D'Elia et al. |
| 7,972,829 B2 | 7/2011 | Kikuchi et al. |
| 8,034,767 B2 | 10/2011 | Kutukova et al. |
| 8,062,869 B2 | 11/2011 | Nakanishi et al. |
| 8,093,346 B2 | 1/2012 | Suzuki et al. |
| 8,105,802 B2 | 1/2012 | Umezawa et al. |
| 8,597,907 B2 | 12/2013 | Date et al. |
| 2003/0082746 A1 | 5/2003 | Kikuchi et al. |
| 2004/0126847 A1 | 7/2004 | Kikuchi et al. |
| 2005/0244935 A1 | 11/2005 | Pompejus et al. |
| 2006/0019367 A1 | 1/2006 | Umezawa et al. |
| 2006/0154345 A1 | 7/2006 | Rayapati et al. |
| 2007/0118916 A1 | 5/2007 | Puzio et al. |
| 2007/0184525 A1 | 8/2007 | Date et al. |
| 2007/0281888 A1 | 12/2007 | Nishikawa et al. |
| 2008/0090272 A1 | 4/2008 | Rayapati et al. |
| 2008/0241888 A1 | 10/2008 | Zakataeva et al. |
| 2010/0159560 A1 | 6/2010 | Umezawa et al. |
| 2010/0297729 A1 | 11/2010 | Kikuchi et al. |

FOREIGN PATENT DOCUMENTS

| | | |
|---|---|---|
| EP | 1059358 | 12/2000 |
| EP | 1548116 | 6/2005 |
| EP | 1602722 A1 | 12/2005 |
| EP | 1748077 | 1/2007 |
| JP | 11-169182 A | 6/1999 |
| JP | 2003-506030 A | 2/2003 |
| WO | WO2013/065772 A1 | 5/2013 |
| WO | WO2013/065869 | 5/2013 |

OTHER PUBLICATIONS

Kikuchi, Y., "Bio Iyakuhin Seisan ni Muketa Atarashii Tanpakushitsu Seisan System no Kaihatsu to Tanpakushitsu Hatsugen Jutaku Service," Pharm. Tech. Japan 2011;27(3);87(491)-91(495).

Pompejus, M., et al., SEQ ID No. 56, Publication Site for Issued and Published Sequences (PSIPS) [online], Nov. 2005; United States Patent and Trademark Office, Alexandria, VA, USA, [retrieved on Jan. 29, 2013] Retrieved from the Internet: <URL:http://seqdata.uspto.govt.psipsv?pageRequest=viewSequence&DociD=20050244935&seqID=56>, SEQ ID No. 56.

International Search Report for PCT Patent App. No. PCT/JP2012/078285 (Feb. 12, 2013).

International Preliminary Report on Patentability for PCT Patent App. No. PCT/JP2012/078285 (May 6, 2014). [submitted as concise explanation of the relevancy of Japanese language document cited herein, Kikuchi et al., Pharm. Tech. Japan 2011;27(3);87(491)-91(495).].

Bayan, N., et al., "Mycomembrane and S-layer: two important structures of Corynebacterium glutamicum cell envelope with promising biotechnology applications," J. Biotechnol. 2003;104:55-67.

Sundaram, R. K., et al., "Expression of a functional single-chain antibody via Corynebacterium pseudodiphtheriticum," Eur. J. Clin. Microbiol. Infect. Dis. 2008;27:617-622.

Office Action from U.S. Appl. No. 14/264,600 (Jul. 30, 2015).

Kikuchi, Y., et al., "TatABC overexpression improves Tat-dependent protein secretion in Corynebacterium glutamicum," New Biotechnol. 2009;25S:S224-S225.

(Continued)

*Primary Examiner* — Suzanne M Noakes
*Assistant Examiner* — Jae W Lee
(74) *Attorney, Agent, or Firm* — Shelly Guest Cermak; Cermak Nakajima & McGowan LLP

(57) ABSTRACT

A method for secretory production of a heterologous protein is provided by developing a novel technique for improving ability of a coryneform bacterium to produce a heterologous protein by secretory production. By utilizing a coryneform bacterium having an ability to produce a heterologous protein by secretory production which has been modified so that the activity of a penicillin-binding protein is reduced and in which the activity of a cell surface layer protein has been reduced as an expression host, a heterologous protein is produced by secretory production.

7 Claims, 11 Drawing Sheets

(56) References Cited

OTHER PUBLICATIONS

Matsuda, Y., et al., "Double mutation of cell wall proteins CspB and PBP1a increases secretion of the antibody Fab fragment from Corynebacterium glutamicum," Microbial Cell Factories 2014;13:1-10.

Radmacher, E., et al., "Ethambutol, a cell wall inhibitor of Mycobacterium tuberculosis, elicits L-glutamate efflux of Corynebacterium glutamicum," Microbiol. 2005;151:1359-1368.

Supplementary European Search Report for European Patent App. No. 12845191.1 (Feb. 18, 2015).

Billman-Jacobe, H., et al., "Expression and Secretion of Heterologous Proteases by Corynebacterium glutannicum," Appl. Environmen. Microbiol. 1995;61(4):1610-1613.

Christensen, T., et al., "High Level Expression of Recombinant Genes in Aspergillus Oryzae," Bio/Technology 1988;6:1419-1422.

Cregg, J. M., et al., "Recent Advances in the Expression of Foreign Genes in Pichia pastoris," Bio/Technology 1993;11:905-910.

Dunn-Coleman, N. S., et al., "Commercial Levels of Chymosin Production by Aspergillus," Bio/Technology 1991;9:976-981.

Hansmeier, N., et al., "Classification of hyper-variable Corynebacterium glutamicum surface-layer proteins by sequence analyses and atomic force microscopy," J. Biotechnol. 2004;112:177-193.

Letek, M., et al., "Cell growth and cell division in the rod-shaped actinomycete Corynebacterium glutamicum," Antonie van Leeuwenhoek 2008;94:99-109.

Liebel, W., et al., "Expression, Secretion, and Processing of Staphylococcal Nuclease by Corynebacterium glutamicum," J. Bacteriol. 1992;174(6):1854-1861.

Salim, K., et al., "Heterologous Expression of the Mycobacterium tuberculosis Gene Encoding Antigen 85A in Corynebacterium glutamicum," Appl. Environmen. Microbiol. 1997;63(11):4392-4400.

Simonen, M., et al., "Protein secretion in *Bacillus Species*," Microbiol. Revs. 1993;57(1):109-137.

Peyret, J. L, et al., "Characterization of the cspB gene encoding PS2, an ordered surface-layer protein in Corynebacterium glutamicum," Mol. Microbiol. 1993;9(1):97-109.

Valbuena, N., et al., "Characterization of HMW-PBPs from the rod-shaped actinomycete Corynebacterium glutamicum: peptidoglycan synthesis in cells lacking actin-like cytoskeletal structures," Mol. Microbiol. 2007;66 (3):643-657.

International Search Report for PCT Patent App. No. PCT/JP2012/078906 (Jan. 31, 2013).

Written Opinion for PCT Patent App. No. PCT/JP2012/078906 (Jan. 31, 2013).

International Preliminary Report on Patentability for PCT Patent App. No. PCT/JP2012/078285 (May 6, 2014).

lane 1, YDK010/pPK4
lane 2, YDK010ΔPBP1a/pPK4
lane 3, YDK010/pPKStrast-Fc(H224D-450)
lane 4, YDK010ΔPBP1a/pPKStrast-Fc(H224D-450)
lane 5, YDK010/pPKStrast-Fc(H231P-450)
lane 6, YDK010ΔPBP1a/pPKStrast-Fc(H231P-450)

lane 1, Marker
lane 2, ATCC13869/pPK4
lane 3, ATCC13869/pPKStrast-FabH(1-229C)+L
lane 4, ATCC13869ΔCspB/pPKStrast-FabH(1-229C)+L
lane 5, ATCC13869ΔPBP1a/pPKStrast-FabH(1-229C)+L
lane 6, ATCC13869ΔCspBΔPBP1a/pPKStrast-FabH(1-229C)+L

SEQUENCE LISTING

```
<160> NUMBER OF SEQ ID NOS: 100

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
gtcggatccg cccccctgag ccaaatattc                                        30

<210> SEQ ID NO 2
<211> LENGTH: 54
<212> TYPE: DNA
<213> ORGANISM: Artificial Sequence
<220> FEATURE:
<223> OTHER INFORMATION: primer

<400> SEQUENCE: 2
tttctagcgg aagaactggt tgatggcgtc gagctttgtc agagaattcg tggt            54

<210> SEQ ID NO 3
<211> LENGTH: 52
<212> TYPE: DNA
<213> ORGANISM: Artificial Sequence
<220> FEATURE:
<223> OTHER INFORMATION: primer

<400> SEQUENCE: 3
gtgtccacca cgaattctct gacaaagctc gacgccatca accagttctt cc              52

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4
agtatctaga ttcgagtcgc ttttggttgg c                                     31

<210> SEQ ID NO 5
<211> LENGTH: 21
<212> TYPE: DNA
<213> ORGANISM: Artificial Sequence
<220> FEATURE:
<223> OTHER INFORMATION: primer
```

```
<400> SEQUENCE: 5
cggcgaactc aaaaacagca t                                              21

<210> SEQ ID NO 6
<211> LENGTH: 44
<212> TYPE: DNA
<213> ORGANISM: Artificial Sequence
<220> FEATURE:
<223> OTHER INFORMATION: primer

<400> SEQUENCE: 6
ggatagtcag ccccggcagg atcctttgc cactgctctt tttg                     44

<210> SEQ ID NO 7
<211> LENGTH: 43
<212> TYPE: DNA
<213> ORGANISM: Artificial Sequence
<220> FEATURE:
<223> OTHER INFORMATION: primer

<400> SEQUENCE: 7
caaaaagagc agtggcaaaa ggatcctgcc ggggctgact atc                     43

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ccaaacaacc cgaagctcaa c                                              21

<210> SEQ ID NO 9
<211> LENGTH: 60
<212> TYPE: DNA
<213> ORGANISM: Artificial Sequence
<220> FEATURE:
<223> OTHER INFORMATION: H chain

<400> SEQUENCE: 9
gaggttcaac tggtggagag cggcggcgga ctggttcaac caggcggcag cctccgcctg    60

<210> SEQ ID NO 10
<211> LENGTH: 60
<212> TYPE: DNA
<213> ORGANISM: Artificial Sequence
<220> FEATURE:
<223> OTHER INFORMATION: H chain

<400> SEQUENCE: 10
caacattaag gatacctaca tccattgggt tcgccaggca ccgggaaaag gattggaatg    60

<210> SEQ ID NO 11
<211> LENGTH: 60
<212> TYPE: DNA
<213> ORGANISM: Artificial Sequence
<220> FEATURE:
<223> OTHER INFORMATION: H chain

<400> SEQUENCE: 11
ctaatggcta cacccgctat gccgattccg ttaagggccg ctttaccatc tccgctgata    60

<210> SEQ ID NO 12
```

```
<211> LENGTH: 60
<212> TYPE: DNA
<213> ORGANISM: Artificial Sequence
<220> FEATURE:
<223> OTHER INFORMATION: H chain

<400> SEQUENCE: 12
ctgcaaatga actccttgcg cgcagaagac accgcagtgt actactgttc ccgctggggc    60

<210> SEQ ID NO 13
<211> LENGTH: 60
<212> TYPE: DNA
<213> ORGANISM: Artificial Sequence
<220> FEATURE:
<223> OTHER INFORMATION: H chain

<400> SEQUENCE: 13
ggattactgg ggccagggca ccctcgtcac ggtctccagc gctagcacca agggtccatc    60

<210> SEQ ID NO 14
<211> LENGTH: 60
<212> TYPE: DNA
<213> ORGANISM: Artificial Sequence
<220> FEATURE:
<223> OTHER INFORMATION: H chain

<400> SEQUENCE: 14
gcagcaagag cacctccggc ggcaccgcgg cactcggctg ccttgtgaaa gattacttcc    60

<210> SEQ ID NO 15
<211> LENGTH: 60
<212> TYPE: DNA
<213> ORGANISM: Artificial Sequence
<220> FEATURE:
<223> OTHER INFORMATION: H chain

<400> SEQUENCE: 15
tggaactccg gcgcccttac ctccggcgtt cataccttcc ccgcagtgct gcaatcctcc    60

<210> SEQ ID NO 16
<211> LENGTH: 60
<212> TYPE: DNA
<213> ORGANISM: Artificial Sequence
<220> FEATURE:
<223> OTHER INFORMATION: H chain

<400> SEQUENCE: 16
cgtcgtgacc gtcccgtcct cctccctggg cacccagacc tatatctgta acgtgaacca    60

<210> SEQ ID NO 17
<211> LENGTH: 60
<212> TYPE: DNA
<213> ORGANISM: Artificial Sequence
<220> FEATURE:
<223> OTHER INFORMATION: H chain

<400> SEQUENCE: 17
tcgataaaaa ggtggaacca aaatcctgtg ataaaactca cacctgccca ccgtgccccg    60

<210> SEQ ID NO 18
<211> LENGTH: 60
<212> TYPE: DNA
<213> ORGANISM: Artificial Sequence
<220> FEATURE:
<223> OTHER INFORMATION: H chain

<400> SEQUENCE: 18
```
ccgtccgtct tcttgttccc tccaaagccc aaagatacct tgatgatttc tcgcacccccg    60

<210> SEQ ID NO 19
<211> LENGTH: 60
<212> TYPE: DNA
<213> ORGANISM: Artificial Sequence
<220> FEATURE:
<223> OTHER INFORMATION: H chain

<400> SEQUENCE: 19
ggatgtgagc cacgaggacc ctgaagttaa gttcaactgg tacgttgatg gcgtggaagt    60

<210> SEQ ID NO 20
<211> LENGTH: 60
<212> TYPE: DNA
<213> ORGANISM: Artificial Sequence
<220> FEATURE:
<223> OTHER INFORMATION: H chain

<400> SEQUENCE: 20
cacgcgaaga acagtacaac tccacttatc gcgttgtctc tgtgctcacc gtcctgcacc    60

<210> SEQ ID NO 21
<211> LENGTH: 60
<212> TYPE: DNA
<213> ORGANISM: Artificial Sequence
<220> FEATURE:
<223> OTHER INFORMATION: H chain

<400> SEQUENCE: 21
gaatacaaat gcaaagtttc caacaaggct ctgccggcac cgattgagaa gaccatctcc    60

<210> SEQ ID NO 22
<211> LENGTH: 60
<212> TYPE: DNA
<213> ORGANISM: Artificial Sequence
<220> FEATURE:
<223> OTHER INFORMATION: H chain

<400> SEQUENCE: 22
cgaacctcaa gtgtacaccc ttcccccgtc tcgtgatgaa ttgacgaaga accaggtcag    60

<210> SEQ ID NO 23
<211> LENGTH: 60
<212> TYPE: DNA
<213> ORGANISM: Artificial Sequence
<220> FEATURE:
<223> OTHER INFORMATION: H chain

<400> SEQUENCE: 23
gtttttatcc ttccgatatt gcggtcgagt gggaatctaa cggccaaccc gaaaacaatt    60

<210> SEQ ID NO 24
<211> LENGTH: 60
<212> TYPE: DNA
<213> ORGANISM: Artificial Sequence
<220> FEATURE:
<223> OTHER INFORMATION: H chain

<400> SEQUENCE: 24
ctggacagcg acggcagctt ctttctttac agcaaactga ccgtggataa atcccgctgg    60

<210> SEQ ID NO 25
<211> LENGTH: 60
<212> TYPE: DNA

<213> ORGANISM: Artificial Sequence
<220> FEATURE:
<223> OTHER INFORMATION: H chain

<400> SEQUENCE: 25
ctgcagcgtc atgcacgagg cactgcacaa ccactatacc cagaaatccc tctcccttc    60

<210> SEQ ID NO 26
<211> LENGTH: 33
<212> TYPE: DNA
<213> ORGANISM: Artificial Sequence
<220> FEATURE:
<223> OTHER INFORMATION: H chain

<400> SEQUENCE: 26
tcacttgcct ggggaaaggg agagggattt ctg                                33

<210> SEQ ID NO 27
<211> LENGTH: 60
<212> TYPE: DNA
<213> ORGANISM: Artificial Sequence
<220> FEATURE:
<223> OTHER INFORMATION: H chain

<400> SEQUENCE: 27
cctcgtgcat gacgctgcag gaaaagacgt tgccctgctg ccagcgggat ttatccacgg    60

<210> SEQ ID NO 28
<211> LENGTH: 60
<212> TYPE: DNA
<213> ORGANISM: Artificial Sequence
<220> FEATURE:
<223> OTHER INFORMATION: H chain

<400> SEQUENCE: 28
aagctgccgt cgctgtccag cacaggcggg gtggtcttat aattgttttc gggttggccg    60

<210> SEQ ID NO 29
<211> LENGTH: 60
<212> TYPE: DNA
<213> ORGANISM: Artificial Sequence
<220> FEATURE:
<223> OTHER INFORMATION: H chain

<400> SEQUENCE: 29
aatatcggaa ggataaaaac ctttgaccag gcacgtgagg ctgacctggt tcttcgtcaa    60

<210> SEQ ID NO 30
<211> LENGTH: 60
<212> TYPE: DNA
<213> ORGANISM: Artificial Sequence
<220> FEATURE:
<223> OTHER INFORMATION: H chain

<400> SEQUENCE: 30
gggtgtacac ttgaggttcg cgaggctggc cttttgcctt ggagatggtc ttctcaatcg    60

<210> SEQ ID NO 31
<211> LENGTH: 60
<212> TYPE: DNA
<213> ORGANISM: Artificial Sequence
<220> FEATURE:
<223> OTHER INFORMATION: H chain

<400> SEQUENCE: 31
gaaactttgc atttgtattc tttaccgttc aaccaatctt ggtgcaggac ggtgagcaca    60

```
<210> SEQ ID NO 32
<211> LENGTH: 60
<212> TYPE: DNA
<213> ORGANISM: Artificial Sequence
<220> FEATURE:
<223> OTHER INFORMATION: H chain

<400> SEQUENCE: 32
gttgtactgt tcttcgcgtg gcttggtctt ggcattatga acttccacgc catcaacgta      60

<210> SEQ ID NO 33
<211> LENGTH: 60
<212> TYPE: DNA
<213> ORGANISM: Artificial Sequence
<220> FEATURE:
<223> OTHER INFORMATION: H chain

<400> SEQUENCE: 33
ggtcctcgtg gctcacatcc acgaccacgc aggtgacttc cggggtgcga gaaatcatca      60

<210> SEQ ID NO 34
<211> LENGTH: 60
<212> TYPE: DNA
<213> ORGANISM: Artificial Sequence
<220> FEATURE:
<223> OTHER INFORMATION: H chain

<400> SEQUENCE: 34
gggaacaaga agacggacgg acctccaaga agttcgggag cggggcacgg tgggcaggtg      60

<210> SEQ ID NO 35
<211> LENGTH: 60
<212> TYPE: DNA
<213> ORGANISM: Artificial Sequence
<220> FEATURE:
<223> OTHER INFORMATION: H chain

<400> SEQUENCE: 35
tggttccacc tttttatcga ccttggtgtt ggacggcttg tggttcacgt tacagatata      60

<210> SEQ ID NO 36
<211> LENGTH: 60
<212> TYPE: DNA
<213> ORGANISM: Artificial Sequence
<220> FEATURE:
<223> OTHER INFORMATION: H chain

<400> SEQUENCE: 36
aggacgggac ggtcacgacg gagctcaggg agtacagtcc ggaggattgc agcactgcgg      60

<210> SEQ ID NO 37
<211> LENGTH: 60
<212> TYPE: DNA
<213> ORGANISM: Artificial Sequence
<220> FEATURE:
<223> OTHER INFORMATION: H chain

<400> SEQUENCE: 37
gtaagggcgc cggagttcca gctcacagta actggttccg ggaagtaatc tttcacaagg      60

<210> SEQ ID NO 38
<211> LENGTH: 60
<212> TYPE: DNA
<213> ORGANISM: Artificial Sequence
<220> FEATURE:
```

```
<223> OTHER INFORMATION: H chain

<400> SEQUENCE: 38
gccggaggtg ctcttgctgc tcggcgccaa aggaaaaacg gatggaccct tggtgctagc    60

<210> SEQ ID NO 39
<211> LENGTH: 60
<212> TYPE: DNA
<213> ORGANISM: Artificial Sequence
<220> FEATURE:
<223> OTHER INFORMATION: H chain

<400> SEQUENCE: 39
tgccctggcc ccagtaatcc atagcgtaga agccgtcgcc gccccagcgg aacagtagt    60

<210> SEQ ID NO 40
<211> LENGTH: 60
<212> TYPE: DNA
<213> ORGANISM: Artificial Sequence
<220> FEATURE:
<223> OTHER INFORMATION: H chain

<400> SEQUENCE: 40
cgcaaggagt tcatttgcag gtatgcagtg tttttggagg tatcagcgga gatggtaaag    60

<210> SEQ ID NO 41
<211> LENGTH: 60
<212> TYPE: DNA
<213> ORGANISM: Artificial Sequence
<220> FEATURE:
<223> OTHER INFORMATION: H chain

<400> SEQUENCE: 41
atagcgggtg tagccattag tgggatagat acgcgccacc cattccaatc cttttcccgg    60

<210> SEQ ID NO 42
<211> LENGTH: 60
<212> TYPE: DNA
<213> ORGANISM: Artificial Sequence
<220> FEATURE:
<223> OTHER INFORMATION: H chain

<400> SEQUENCE: 42
tgtaggtatc cttaatgttg aatccggagg cggcacaaga caggcggagg ctgccgcctg    60

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
gaggttcaac tggtggagag                                               20

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
tcacttgcct ggggaaaggg g                                             21
```

<210> SEQ ID NO 45
<211> LENGTH: 1353
<212> TYPE: DNA
<213> ORGANISM: Artificial Sequence
<220> FEATURE:
<223> OTHER INFORMATION: H chain of Trastuzumab

<400> SEQUENCE: 45

```
gaggttcaac tggtggagag cggcggcgga ctggttcaac caggcggcag cctccgcctg      60
tcttgtgccg cctccggatt caacattaag gatacctaca tccattgggt tcgccaggca     120
ccgggaaaag gattggaatg ggtggcgcgt atctatccca ctaatggcta cacccgctat     180
gccgattccg ttaagggccg ctttaccatc tccgctgata cctccaaaaa cactgcatac     240
ctgcaaatga actccttgcg cgcagaagac accgcagtgt actactgttc ccgctggggc     300
ggcgacggct tctacgctat ggattactgg ggccagggca ccctcgtcac ggtctccagc     360
gctagcacca agggtccatc cgttttcct ttggcgccga gcagcaagag cacctccggc     420
ggcaccgcgg cactcggctg ccttgtgaaa gattacttcc cggaaccagt tactgtgagc     480
tggaactccg gcgcccttac ctccggcgtt catacccttcc ccgcagtgct gcaatcctcc     540
ggactgtact ccctgagctc cgtcgtgacc gtcccgtcct cctccctggg cacccagacc     600
tatatctgta acgtgaacca caagccgtcc aacaccaagg tcgataaaaa ggtggaacca     660
aaatcctgtg ataaaactca cacctgccca ccgtgcccg ctcccgaact tcttggaggt     720
ccgtccgtct tcttgttccc tccaaagccc aaagatacct tgatgatttc tcgcacccg      780
gaagtcacct gcgtggtcgt ggatgtgagc cacgaggacc ctgaagttaa gttcaactgg     840
tacgttgatg gcgtggaagt tcataatgcc aagaccaagc cacgcgaaga acagtacaac     900
tccacttatc gcgttgtctc tgtgctcacc gtcctgcacc aagattggtt gaacggtaaa     960
gaatacaaat gcaaagtttc caacaaggct ctgccggcac cgattgagaa gaccatctcc    1020
aaggcaaaag gccagcctcg cgaacctcaa gtgtacaccc ttccccccgtc tcgtgatgaa    1080
ttgacgaaga accaggtcag cctcacgtgc ctggtcaaag ttttttatcc ttccgatatt    1140
gcggtcgagt gggaatctaa cggccaaccc gaaaacaatt ataagaccac cccgcctgtg    1200
ctggacagcg acggcagctt ctttctttac agcaaactga ccgtggataa atcccgctgg    1260
cagcagggca acgtcttttc ctgcagcgtc atgcacgagg cactgcacaa ccactatacc    1320
cagaaatccc tctcccttt cccaggcaag tga                                   1353
```

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46

```
gaattcgagc tcggtaccca aattcctgtg                                        30
```

<210> SEQ ID NO 47
<211> LENGTH: 40
<212> TYPE: DNA
<213> ORGANISM: Artificial Sequence
<220> FEATURE:
<223> OTHER INFORMATION: primer

<400> SEQUENCE: 47

```
ctctccacca gttgaacctc tgccgttgcc acaggtgcgg                             40
```

```
<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
ggcaggtgtg ggtacctcaa caggattttg                                              30

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
gagcggggca ggtacctcag gtgtgagttt                                              30

<210> SEQ ID NO 50
<211> LENGTH: 30
<212> TYPE: DNA
<213> ORGANISM: Artificial Sequence
<220> FEATURE:
<223> OTHER INFORMATION: primer

<400> SEQUENCE: 50
cgggagcggg ggtacctcag caggtgtgag                                              30

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
gttcgggagc ggtacctcat gggcaggtgt                                              30

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52
gaagttcggg ggtacctcac ggtgggcagg                                              30

<210> SEQ ID NO 53
<211> LENGTH: 30
<212> TYPE: DNA
<213> ORGANISM: Artificial Sequence
<220> FEATURE:
<223> OTHER INFORMATION: primer

<400> SEQUENCE: 53
caagaagttc ggtacctcag cacggtgggc                                              30

<210> SEQ ID NO 54
<211> LENGTH: 30
<212> TYPE: DNA
<213> ORGANISM: Artificial Sequence
<220> FEATURE:
<223> OTHER INFORMATION: primer
```

<400> SEQUENCE: 54
ctccaagaag ggtacctcag gggcacggtg                              30

<210> SEQ ID NO 55
<211> LENGTH: 60
<212> TYPE: DNA
<213> ORGANISM: Artificial Sequence
<220> FEATURE:
<223> OTHER INFORMATION: L chain

<400> SEQUENCE: 55
gatattcaaa tgacccagag cccctccagc ctgtccgcaa gcgtcggcga ccgcgtcacc    60

<210> SEQ ID NO 56
<211> LENGTH: 60
<212> TYPE: DNA
<213> ORGANISM: Artificial Sequence
<220> FEATURE:
<223> OTHER INFORMATION: L chain

<400> SEQUENCE: 56
agacgttaat accgccgtgg catggtatca gcagaagcca ggcaaagcac caaagctgct    60

<210> SEQ ID NO 57
<211> LENGTH: 60
<212> TYPE: DNA
<213> ORGANISM: Artificial Sequence
<220> FEATURE:
<223> OTHER INFORMATION: L chain

<400> SEQUENCE: 57
tgtattccgg cgtcccctct cgcttttccg gttcccgctc cggcaccgac ttcactctta    60

<210> SEQ ID NO 58
<211> LENGTH: 60
<212> TYPE: DNA
<213> ORGANISM: Artificial Sequence
<220> FEATURE:
<223> OTHER INFORMATION: L chain

<400> SEQUENCE: 58
gaagacttcg ccacgtatta ctgccaacaa cactacacga cccccccgac cttcggacag    60

<210> SEQ ID NO 59
<211> LENGTH: 60
<212> TYPE: DNA
<213> ORGANISM: Artificial Sequence
<220> FEATURE:
<223> OTHER INFORMATION: L chain

<400> SEQUENCE: 59
gcgcaccgtc gccgcccct ccgtcttcat tttcccacca tctgacgaac agctgaaatc    60

<210> SEQ ID NO 60
<211> LENGTH: 60
<212> TYPE: DNA
<213> ORGANISM: Artificial Sequence
<220> FEATURE:
<223> OTHER INFORMATION: L chain

<400> SEQUENCE: 60
gcctgttgaa caactttac ccccgcgagg caaaagtgca atggaaggtc gataacgcac    60

<210> SEQ ID NO 61

```
<210> SEQ ID NO 61
<211> LENGTH: 60
<212> TYPE: DNA
<213> ORGANISM: Artificial Sequence
<220> FEATURE:
<223> OTHER INFORMATION: L chain

<400> SEQUENCE: 61
gagtccgtga ccgaacagga ctccaaggat tctacctact ccctcagctc caccctcacc    60

<210> SEQ ID NO 62
<211> LENGTH: 60
<212> TYPE: DNA
<213> ORGANISM: Artificial Sequence
<220> FEATURE:
<223> OTHER INFORMATION: L chain

<400> SEQUENCE: 62
gaaacacaag gtctatgcct gcgaggtgac ccaccagggc ctttcctctc ccgtgaccaa    60

<210> SEQ ID NO 63
<211> LENGTH: 45
<212> TYPE: DNA
<213> ORGANISM: Artificial Sequence
<220> FEATURE:
<223> OTHER INFORMATION: L chain

<400> SEQUENCE: 63
tcagcattcg ccgcggttaa aggacttggt cacgggagag gaaag                    45

<210> SEQ ID NO 64
<211> LENGTH: 60
<212> TYPE: DNA
<213> ORGANISM: Artificial Sequence
<220> FEATURE:
<223> OTHER INFORMATION: L chain

<400> SEQUENCE: 64
aggcatagac cttgtgtttc tcgtagtccg ccttggagag ggtgagggtg gagctgaggg    60

<210> SEQ ID NO 65
<211> LENGTH: 60
<212> TYPE: DNA
<213> ORGANISM: Artificial Sequence
<220> FEATURE:
<223> OTHER INFORMATION: L chain

<400> SEQUENCE: 65
tcctgttcgg tcacggactc ttgggaatta ccggattgca gtgcgttatc gaccttccat    60

<210> SEQ ID NO 66
<211> LENGTH: 60
<212> TYPE: DNA
<213> ORGANISM: Artificial Sequence
<220> FEATURE:
<223> OTHER INFORMATION: L chain

<400> SEQUENCE: 66
gtaaaagttg ttcaacaggc acaccacaga agcagtaccg gatttcagct gttcgtcaga    60

<210> SEQ ID NO 67
<211> LENGTH: 60
<212> TYPE: DNA
<213> ORGANISM: Artificial Sequence
<220> FEATURE:
<223> OTHER INFORMATION: L chain

<400> SEQUENCE: 67
```

```
aggggggcggc gacggtgcgc ttaatctcga ccttggtgcc ctgtccgaag gtcggggggg    60
```

<210> SEQ ID NO 68
<211> LENGTH: 60
<212> TYPE: DNA
<213> ORGANISM: Artificial Sequence
<220> FEATURE:
<223> OTHER INFORMATION: L chain

<400> SEQUENCE: 68

```
taatacgtgg cgaagtcttc tggttgcaag ctggagatgg taagagtgaa gtcggtgccg    60
```

<210> SEQ ID NO 69
<211> LENGTH: 60
<212> TYPE: DNA
<213> ORGANISM: Artificial Sequence
<220> FEATURE:
<223> OTHER INFORMATION: L chain

<400> SEQUENCE: 69

```
agaggggacg ccggaataca agaaagaggc ggagtagatg agcagctttg gtgctttgcc    60
```

<210> SEQ ID NO 70
<211> LENGTH: 60
<212> TYPE: DNA
<213> ORGANISM: Artificial Sequence
<220> FEATURE:
<223> OTHER INFORMATION: L chain

<400> SEQUENCE: 70

```
ccacggcggt attaacgtct tggctggcgc ggcaagtaat ggtgacgcgg tcgccgacgc    60
```

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71

```
gatattcaaa tgacccagag                                                20
```

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72

```
tcagcattcg ccgcggttaa                                                20
```

<210> SEQ ID NO 73
<211> LENGTH: 645
<212> TYPE: DNA
<213> ORGANISM: Artificial Sequence
<220> FEATURE:
<223> OTHER INFORMATION: L chain of Trastuzumab

<400> SEQUENCE: 73

```
gatattcaaa tgacccagag cccctccagc ctgtccgcaa gcgtcggcga ccgcgtcacc    60
attacttgcc gcgccagcca agacgttaat accgccgtgg catggtatca gcagaagcca   120
ggcaaagcac caaagctgct catctactcc gcctctttct gtattccggg cgtcccctct   180
```

| | |
|---|---|
| cgcttttccg gttcccgctc cggcaccgac ttcactctta ccatctccag cttgcaacca | 240 |
| gaagacttcg ccacgtatta ctgccaacaa cactacacga ccccccgac cttcggacag | 300 |
| ggcaccaagg tcgagattaa gcgcaccgtc gccgccccct ccgtcttcat tttcccacca | 360 |
| tctgacgaac agctgaaatc cggtactgct tctgtggtgt gcctgttgaa caacttttac | 420 |
| ccccgcgagg caaaagtgca atggaaggtc gataacgcac tgcaatccgg taattcccaa | 480 |
| gagtccgtga ccgaacagga ctccaaggat tctacctact ccctcagctc caccctcacc | 540 |
| ctctccaagg cggactacga gaaacacaag gtctatgcct gcgaggtgac ccaccagggc | 600 |
| ctttcctctc ccgtgaccaa gtcctttaac cgcggcgaat gctga | 645 |

```
<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
```

| | |
|---|---|
| gaattcgagc tcggatccca aattcctgtg | 30 |

```
<210> SEQ ID NO 75
<211> LENGTH: 40
<212> TYPE: DNA
<213> ORGANISM: Artificial Sequence
<220> FEATURE:
<223> OTHER INFORMATION: primer

<400> SEQUENCE: 75
```

| | |
|---|---|
| ctctgggtca tttgaatatc tgccgttgcc acaggtgcgg | 40 |

```
<210> SEQ ID NO 76
<211> LENGTH: 40
<212> TYPE: DNA
<213> ORGANISM: Artificial Sequence
<220> FEATURE:
<223> OTHER INFORMATION: primer

<400> SEQUENCE: 76
```

| | |
|---|---|
| tcgtcgtcgt cgtcggatcc tcagcattcg ccgcggttaa | 40 |

```
<210> SEQ ID NO 77
<211> LENGTH: 40
<212> TYPE: DNA
<213> ORGANISM: Artificial Sequence
<220> FEATURE:
<223> OTHER INFORMATION: primer

<400> SEQUENCE: 77
```

| | |
|---|---|
| tcgtcgtcgt cgtcggtacc tcacttgcct ggggaaaggg | 40 |

```
<210> SEQ ID NO 78
<211> LENGTH: 40
<212> TYPE: DNA
<213> ORGANISM: Artificial Sequence
<220> FEATURE:
<223> OTHER INFORMATION: primer

<400> SEQUENCE: 78
```

| | |
|---|---|
| ccgcacctgt ggcaacggca gatattcaaa tgacccagag | 40 |

```
<210> SEQ ID NO 79
<211> LENGTH: 40
```

<212> TYPE: DNA
<213> ORGANISM: Artificial Sequence
<220> FEATURE:
<223> OTHER INFORMATION: primer

<400> SEQUENCE: 79

```
ccgcacctgt ggcaacggca ccgtgccccg ctcccgaact                    40
```

<210> SEQ ID NO 80
<211> LENGTH: 25
<212> TYPE: DNA
<213> ORGANISM: Artificial Sequence
<220> FEATURE:
<223> OTHER INFORMATION: primer

<400> SEQUENCE: 80

```
tgccgttgcc acaggtgcgg ccagc                                   25
```

<210> SEQ ID NO 81
<211> LENGTH: 2388
<212> TYPE: DNA
<213> ORGANISM: Corynebacterium glutamicum

<400> SEQUENCE: 81

```
gtgtccacca cgaattctct gacaaagctc gttgcatcta cagtcgccgc tggcgtcctt    60
ggtgcgctcg cacttgtgcc tttcgctagt ctttctggcg ttgcggttgc gcgtaccaat   120
gacacgatgc agaccaacct ttcagatctg acggatggtc gcgggccggg cgtcacgacg   180
attactgatt ccactgacca gccgattgct tatatttatg cgcagcggcg gtttgaggtt   240
gggggtgatc agatttctac gtcgatgaag gatgcgatcg tttcgattga ggatcgcagg   300
ttctatgagc atgatggtgt ggatttgcag ggctttggtc gtgcaatcct gacgaacctg   360
gctgcgggtg gcgtggagca gggtgcttcg acgattaacc agcagtatgt gaagaacttc   420
ttgctgttgg tggaagctga tgatgaggcg agcaggctg ctgctgtgga aacctccatc   480
cctcgtaagc tccgtgagat aagatggcg tctgatttgg aaaagacgtt gtcgaaggat   540
gagattctga ctcgttatct caacattgtt ccttttggta atggtgctta tggtgttgag   600
gctgcggcgc ggacgtattt cggtacgtcg gctgccgagt taaccattcc acagtctgcg   660
atgctcgcgg gcattgtgca gtcttcgtct tatctcaatc catacaccaa tcacgatgct   720
gtgtttgagc gtcgtaatac tgttttgggc gctatggctg atgctggcgc gatttcccca   780
gacgaggctt cggctttcca gcaggaacct ttgggtgtcc tggaaacccc gcaaggctta   840
tccaatggtt gtatcggcgc tggcgatcgt ggtttcttct gcgattacgc tctgcaatat   900
ctttctgagc agggaatcac ccaagatatg ctggcgaagg actcctacac catcaaattg   960
actttggatc cagatgttca ggatgcagcg cacaatgcgg tgtcctccca cgttgatcca  1020
accaccccag gtgtcgctga agttgtgaac gtcattgagc ctggcgagaa ctcccgcgat  1080
attttggcta ttacttcttc ccgcaactac ggccttgacc tggatgctgg tgaaacgatg  1140
ctgcctcagg caacgtcccg tgtgggtaat ggtgccggtt ccattttcaa gatctttacc  1200
gccgctgcag ccattcagca gggcgctggc ctagacacca tgttggatgt tccttctcga  1260
tatgaggtca aggcatgg ctccggcggt gccgcgaact gtcccgcaaa tacttactgc  1320
gtggaaaacg caggatccta cgcgcctcgc atgactctgc aggacgctct cgcgcagtcc  1380
cccaacactg cattcgttga aatgatcgag caggttggcg tggacaccgt tgtggatctt  1440
tcagtaaagc tgggcctgcg aagctacacc gatgaaggtt ccttcgacgg cgaaagctca  1500
```

-continued

```
atcgcggact acatgaagga caacaacctc ggttcttaca ctcttggacc taccgctgtt    1560
aaccctcttg aattgtccaa tgttgctgca accattgcat ccggtggcat gtggtgcgaa    1620
cccaatccca tcgccagcgt ccatgaccgt gaaggcaacg aagtctacat tgaccgccct    1680
gcatgtgagc gcgccatcga tgccgaaacg gcttcagctt tggccgtcgg catgagcaag    1740
gatacggtca gcggaactgc ggcctctgca gccagcatgt acggatggtc cttgccaacc    1800
gcagcgaaga ccggtaccac cgagtccaac cagtcctcag catttatggg cttcaacagc    1860
aactttgccg cagctccata catctacaat gacggcacct ccaccacccc actgtgcagc    1920
ggccccgtcc gccagtgcag cagcggtaac ctcttcggcg taacgaacc agctcaaaca     1980
```
(Note: line 1980 as shown)

```
tggtttaaca tggcaagcaa cgtccccgca gcttcgcaag aacactgcc atccagcagc     2040 gattcattcc gcctcggcac ttccggcgaa ctcctcaacc aggttgtcgg ccaaagcgaa    2100
gcctccgctc gacgcaccct cgaagccaaa ggctacaagg tcaccacgcg ttcagtctcc    2160
ggcgccggca gcgcgcgcgg caccgtagtc agcgcaaccc ctcagggtgc agtgcttatc    2220
gacggtggaa ccgtcatttt ggacatctcc gacggcacaa gccctgcccc cgctgccacc    2280
aacaatgatg acagcgacga tggagacacc cctgctccat caacaaacaa ccgcggaaca    2340
accattgaag acgccatcaa tgacgccatc aaccagttct ccgctag                 2388
```

<210> SEQ ID NO 82
<211> LENGTH: 795
<212> TYPE: PRT
<213> ORGANISM: Corynebacterium glutamicum

<400> SEQUENCE: 82

```
Met Ser Thr Thr Asn Ser Leu Thr Lys Leu Val Ala Ser Thr Val Ala
1               5                  10                  15

Ala Gly Val Leu Gly Ala Leu Ala Leu Val Pro Phe Ala Ser Leu Ser
            20                  25                  30

Gly Val Ala Val Ala Arg Thr Asn Asp Thr Met Gln Thr Asn Leu Ser
        35                  40                  45

Asp Leu Thr Asp Gly Arg Gly Pro Gly Val Thr Thr Ile Thr Asp Ser
    50                  55                  60

Thr Asp Gln Pro Ile Ala Tyr Ile Tyr Ala Gln Arg Arg Phe Glu Val
65                  70                  75                  80

Gly Gly Asp Gln Ile Ser Thr Ser Met Lys Asp Ala Ile Val Ser Ile
                85                  90                  95

Glu Asp Arg Arg Phe Tyr Glu His Asp Gly Val Asp Leu Gln Gly Phe
            100                 105                 110

Gly Arg Ala Ile Leu Thr Asn Leu Ala Ala Gly Gly Val Glu Gln Gly
        115                 120                 125

Ala Ser Thr Ile Asn Gln Gln Tyr Val Lys Asn Phe Leu Leu Leu Val
    130                 135                 140

Glu Ala Asp Asp Glu Ala Glu Gln Ala Ala Val Glu Thr Ser Ile
145                 150                 155                 160

Pro Arg Lys Leu Arg Glu Met Lys Met Ala Ser Asp Leu Glu Lys Thr
                165                 170                 175

Leu Ser Lys Asp Glu Ile Leu Thr Arg Tyr Leu Asn Ile Val Pro Phe
            180                 185                 190

Gly Asn Gly Ala Tyr Gly Val Glu Ala Ala Arg Thr Tyr Phe Gly
        195                 200                 205

Thr Ser Ala Ala Glu Leu Thr Ile Pro Gln Ser Ala Met Leu Ala Gly
    210                 215                 220
```

```
Ile Val Gln Ser Ser Ser Tyr Leu Asn Pro Tyr Thr Asn His Asp Ala
225                 230                 235                 240

Val Phe Glu Arg Arg Asn Thr Val Leu Gly Ala Met Ala Asp Ala Gly
            245                 250                 255

Ala Ile Ser Pro Asp Glu Ala Ser Ala Phe Gln Gln Glu Pro Leu Gly
            260                 265                 270

Val Leu Glu Thr Pro Gln Gly Leu Ser Asn Gly Cys Ile Gly Ala Gly
            275                 280                 285

Asp Arg Gly Phe Phe Cys Asp Tyr Ala Leu Gln Tyr Leu Ser Glu Gln
            290                 295                 300

Gly Ile Thr Gln Asp Met Leu Ala Lys Asp Ser Tyr Thr Ile Lys Leu
305                 310                 315                 320

Thr Leu Asp Pro Asp Val Gln Asp Ala Ala His Asn Ala Val Ser Ser
            325                 330                 335

His Val Asp Pro Thr Thr Pro Gly Val Ala Glu Val Val Asn Val Ile
            340                 345                 350

Glu Pro Gly Glu Asn Ser Arg Asp Ile Leu Ala Ile Thr Ser Ser Arg
            355                 360                 365

Asn Tyr Gly Leu Asp Leu Asp Ala Gly Glu Thr Met Leu Pro Gln Ala
370                 375                 380

Thr Ser Arg Val Gly Asn Gly Ala Gly Ser Ile Phe Lys Ile Phe Thr
385                 390                 395                 400

Ala Ala Ala Ala Ile Gln Gln Gly Ala Gly Leu Asp Thr Met Leu Asp
            405                 410                 415

Val Pro Ser Arg Tyr Glu Val Lys Gly Met Gly Ser Gly Gly Ala Ala
            420                 425                 430

Asn Cys Pro Ala Asn Thr Tyr Cys Val Glu Asn Ala Gly Ser Tyr Ala
            435                 440                 445

Pro Arg Met Thr Leu Gln Asp Ala Leu Ala Gln Ser Pro Asn Thr Ala
            450                 455                 460

Phe Val Glu Met Ile Glu Gln Val Gly Val Asp Thr Val Val Asp Leu
465                 470                 475                 480

Ser Val Lys Leu Gly Leu Arg Ser Tyr Thr Asp Glu Gly Ser Phe Asp
            485                 490                 495

Gly Glu Ser Ser Ile Ala Asp Tyr Met Lys Asp Asn Asn Leu Gly Ser
            500                 505                 510

Tyr Thr Leu Gly Pro Thr Ala Val Asn Pro Leu Glu Leu Ser Asn Val
            515                 520                 525

Ala Ala Thr Ile Ala Ser Gly Gly Met Trp Cys Glu Pro Asn Pro Ile
530                 535                 540

Ala Ser Val His Asp Arg Glu Gly Asn Glu Val Tyr Ile Asp Arg Pro
545                 550                 555                 560

Ala Cys Glu Arg Ala Ile Asp Ala Glu Thr Ala Ser Ala Leu Ala Val
            565                 570                 575

Gly Met Ser Lys Asp Thr Val Ser Gly Thr Ala Ala Ser Ala Ala Ser
            580                 585                 590

Met Tyr Gly Trp Ser Leu Pro Thr Ala Ala Lys Thr Gly Thr Thr Glu
            595                 600                 605

Ser Asn Gln Ser Ser Ala Phe Met Gly Phe Asn Ser Asn Phe Ala Ala
            610                 615                 620

Ala Pro Tyr Ile Tyr Asn Asp Gly Thr Ser Thr Thr Pro Leu Cys Ser
625                 630                 635                 640
```

```
Gly Pro Val Arg Gln Cys Ser Ser Gly Asn Leu Phe Gly Gly Asn Glu
                645                 650                 655

Pro Ala Gln Thr Trp Phe Asn Met Ala Ser Asn Val Pro Ala Ala Ser
            660                 665                 670

Gln Gly Thr Leu Pro Ser Ser Asp Ser Phe Arg Leu Gly Thr Ser
        675                 680                 685

Gly Glu Leu Leu Asn Gln Val Val Gly Gln Ser Glu Ala Ser Ala Arg
    690                 695                 700

Arg Thr Leu Glu Ala Lys Gly Tyr Lys Val Thr Arg Ser Val Ser
705                 710                 715                 720

Gly Ala Gly Ser Ala Arg Gly Thr Val Val Ser Ala Thr Pro Gln Gly
                725                 730                 735

Ala Val Leu Ile Asp Gly Gly Thr Val Ile Leu Asp Ile Ser Asp Gly
            740                 745                 750

Thr Ser Pro Ala Pro Ala Ala Thr Asn Asn Asp Asp Ser Asp Asp Gly
        755                 760                 765

Asp Thr Pro Ala Pro Ser Thr Asn Asn Arg Gly Thr Thr Ile Glu Asp
    770                 775                 780

Ala Ile Asn Asp Ala Ile Asn Gln Phe Phe Arg
785                 790                 795

<210> SEQ ID NO 83
<211> LENGTH: 43
<212> TYPE: PRT
<213> ORGANISM: Corynebacterium glutamicum

<400> SEQUENCE: 83

Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
            20                  25                  30

Leu Thr Met Ser Leu Ala Pro Met Ala Ser Ala
        35                  40

<210> SEQ ID NO 84
<211> LENGTH: 30
<212> TYPE: PRT
<213> ORGANISM: Corynebacterium glutamicum

<400> SEQUENCE: 84

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
            20                  25                  30

<210> SEQ ID NO 85
<211> LENGTH: 25
<212> TYPE: PRT
<213> ORGANISM: Corynebacterium ammoniagenes

<400> SEQUENCE: 85

Met Lys Arg Met Lys Ser Leu Ala Ala Ala Leu Thr Val Ala Gly Ala
1               5                   10                  15

Met Leu Ala Ala Pro Val Ala Thr Ala
            20                  25

<210> SEQ ID NO 86
<211> LENGTH: 450
<212> TYPE: PRT
```

<213> ORGANISM: Artificial Sequence
<220> FEATURE:
<223> OTHER INFORMATION: H chain of Trastuzumab

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

```
385             390              395              400
Leu Asp Ser Asp Gly Ser Phe Phe Leu Tyr Ser Lys Leu Thr Val Asp
                405              410              415

Lys Ser Arg Trp Gln Gln Gly Asn Val Phe Ser Cys Ser Val Met His
                420              425              430

Glu Ala Leu His Asn His Tyr Thr Gln Lys Ser Leu Ser Leu Ser Pro
                435              440              445

Gly Lys
    450

<210> SEQ ID NO 87
<211> LENGTH: 214
<212> TYPE: PRT
<213> ORGANISM: Artificial Sequence
<220> FEATURE:
<223> OTHER INFORMATION: L chain of Trastuzumab

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 88
<211> LENGTH: 1412
<212> TYPE: DNA
<213> ORGANISM: Artificial Sequence
<220> FEATURE:
<223> OTHER INFORMATION: synthesized DNA

<400> SEQUENCE: 88
tctagaaaat tcctgtgaat tagctgattt agtactttc ggaggtgtct attcttacca      60
aatcgtcaag ttgtgggtag agtcacctga atattaattg caccgcacgg gtgatatatg    120
```

-continued

```
cttatttgct caagtagttc gaggttaagt gtattttagg tgaacaaatt tcagcttcgg      180
gtagaagact ttcgatgcgc ttcagagctt ctattgggaa atctgacacc acttgattaa      240
atagcctacc cccgaattgg gggattggtc atttttgct gtgaaggtag ttttgatgca       300
tatgacctgc gtttataaag aaatgtaaac gtgatcagat cgatataaaa gaaacagttt      360
gtactcaggt ttgaagcatt ttctccgatt cgcctggcaa aaatctcaat tgtcgcttac      420
agtttttctc aacgacaggc tgctaagctg ctagttcggt ggcctagtga gtggcgttta      480
cttggataaa agtaatccca tgtcgtgatc agccattttg ggttgtttcc atagcaatcc     540
aaaggtttcg tctttcgata cctattcaag gagccttcgc ctctatgaaa cgcatgaaat      600
cgctggctgc ggcgctcacc gtcgctgggg ccatgctggc cgcacctgtg caacggcag      660 atgttgtcat gacccagacc cccctcagcc tcccggtgag cctcggcgac caagcatcta    720
tttcttgccg ctcttcccaa tccttggtgc actctaacgg aaataccttat cttaactggt   780 acctccaaaa agctggccaa tccccgaagc tgttgatcta taaggtctcc aaccgctttt    840
ctggtgttcc tgatcgcttc tccggctccg gctctggtac cgacttcacc ttgaaaatct    900
ctcgcgtcga agcggaggac ctcggcatct acttctgttc ccagaccacc cacgtgcccc    960
caaccttcgg cggcggtacc aagctggaaa tcaagcgcgg cggatccggt tccggcggat   1020
ctggatccgg tggttccggc tccgaggttc agcttcagca aagcggtcca gaacttgtca   1080
aacccggtgc aagcgtgcgc atgtcctgca agtcctctgg ctacatcttt actgatttct   1140
atatgaactg ggtgcgccaa tcccacggta agtccctcga ctacatcggt tacatctccc   1200
catattccgg cgtcaccggt tacaaccaga aatttaaagg caaggccacc cttaccgtgg   1260
ataaatcttc ctccaccgcg tatatggaac tgcgctccct cacttccgag gactccgcag   1320
tctactattg tgcaggttcc tctggcaaca agtgggccat ggattactgg ggccacggtg   1380
cgtccgtcac tgttagctct taatagtcta ga                                  1412
```

<210> SEQ ID NO 89
<211> LENGTH: 744
<212> TYPE: DNA
<213> ORGANISM: Artificial Sequence
<220> FEATURE:
<223> OTHER INFORMATION: anti- Digoxin scFv

<400> SEQUENCE: 89

```
gatgttgtca tgacccagac ccccctcagc ctcccggtga gcctcggcga ccaagcatct     60
atttcttgcc gctcttccca atccttggtg cactctaacg aaataccta tcttaactgg     120 tacctccaaa aagctggcca atccccgaag ctgttgatct ataaggtctc caaccgcttt    180
tctggtgttc ctgatcgctt ctccggctcc ggctctggta ccgacttcac cttgaaaatc    240
tctcgcgtcg aagcggagga cctcggcatc tacttctgtt cccagaccac ccacgtgccc    300
ccaaccttcg gcggcggtac caagctggaa atcaagcgcg cggatccgg ttccggcgga    360 tctggatccg gtggttccgg ctccgaggtt cagcttcagc aaagcggtcc agaacttgtc   420
aaacccggtg caagcgtgcg catgtcctgc aagtcctctg gctacatctt tactgatttc   480
tatatgaact gggtgcgcca atcccacggt aagtccctcg actacatcgg ttacatctcc   540
ccatattccg gcgtcaccgg ttacaaccag aaatttaaag gcaaggccac ccttaccgtg   600
gataaatctt cctccaccgc gtatatggaa ctgcgctccc tcacttccga ggactccgca   660
gtctactatt gtgcaggttc ctctggcaac aagtgggcca tggattactg gggccacggt   720
```

```
gcgtccgtca ctgttagctc ttaa                                         744
```

<210> SEQ ID NO 90
<211> LENGTH: 247
<212> TYPE: PRT
<213> ORGANISM: Artificial Sequence
<220> FEATURE:
<223> OTHER INFORMATION: anti- Digoxin scFv

<400> SEQUENCE: 90

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Asn Trp Tyr Leu Gln Lys Ala Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Thr
                85                  90                  95

Thr His Val Pro Pro Thr Phe Gly Gly Gly Thr Lys Leu Glu Ile Lys
            100                 105                 110

Arg Gly Gly Ser Gly Ser Gly Ser Gly Ser Gly Ser Gly Ser Gly Ser
        115                 120                 125

Glu Val Gln Leu Gln Gln Ser Gly Pro Glu Leu Val Lys Pro Gly Ala
    130                 135                 140

Ser Val Arg Met Ser Cys Lys Ser Ser Gly Tyr Ile Phe Thr Asp Phe
145                 150                 155                 160

Tyr Met Asn Trp Val Arg Gln Ser His Gly Lys Ser Leu Asp Tyr Ile
                165                 170                 175

Gly Tyr Ile Ser Pro Tyr Ser Gly Val Thr Gly Tyr Asn Gln Lys Phe
            180                 185                 190

Lys Gly Lys Ala Thr Leu Thr Val Asp Lys Ser Ser Thr Ala Tyr
        195                 200                 205

Met Glu Leu Arg Ser Leu Thr Ser Glu Asp Ser Ala Val Tyr Tyr Cys
    210                 215                 220

Ala Gly Ser Ser Gly Asn Lys Trp Ala Met Asp Tyr Trp Gly His Gly
225                 230                 235                 240

Ala Ser Val Thr Val Ser Ser
                245
```

<210> SEQ ID NO 91
<211> LENGTH: 2658
<212> TYPE: DNA
<213> ORGANISM: Artificial Sequence
<220> FEATURE:
<223> OTHER INFORMATION: synthesized DNA

<400> SEQUENCE: 91

```
ggatcccaaa ttcctgtgaa gtagctgatt tagtactttt cggaggtgtc tattcttacc      60
aaatcgtcaa gttgtgggta gagtcacctg aatattaatt gcaccgcacg ggtgatatat     120
gcttatttgc tcaagtagtt cgaggttaag tgtattttag gtgaacaaat ttcagcttcg     180 ggtagaaagac tttcgatgcg cttcagagct tctattggga aatctgacac cacttgatta    240
aatagcctac ccccgaattg ggggattggt cattttttgc tgtgaaggta gttttgatgc     300
```

```
atatgacctg cgtttataaa gaaatgtaaa cgtgatcaga tcgatataaa agaaacagtt    360
tgtactcagg tttgaagcat tttctccgat tcgcctggca aaaatctcaa ttgtcgctta    420
cagttttcct caacgacagg ctgctaagct gctagttcgg tggcctagtg agtggcgttt    480
acttggataa aagtaatccc atgtcgtgat cagccatttt gggttgtttc catagcaatc    540
caaaggtttc gtctttcgat acctattcaa ggagccttcg cctctatgaa acgcatgaaa    600
tcgctggctg cggcgctcac cgtcgctggg gccatgctgg ccgcacctgt ggcaacggca    660
gaagttcagc tggttgagtc cggcggtggc ctggttcagc aggtcgctc cctgcgtctc    720 tcctgcgcag cttccggctt caccttcgat gactacgcaa tgcactgggt cgtcaggct    780 cctggcaagg gcctggaatg ggtgtccgca atcacctgga actccggtca catcgattac    840
gctgactccg tcgagggccg cttcaccatc tcccgtgata cgctaagaa ctccctgtac    900 ctccagatga actccctccg tgcagaagac accgctgtct actactgcgc aaaggtttcc    960
tacctgtcca ccgcttcctc cctcgattac tggggtcagg gcaccctggt taccgtgtcc   1020
tccgcctcca ccaagggtcc atccgtgttc ccgctcgcac catcctccaa gtccacctcc   1080
ggtggcaccg ccgcgctggg ttgcctcgtc aaggactact cccagaacc tgtcaccgtt   1140 tcctggaact ccggtgccct gacctccggt gtgcacacct tcccagcggt cctccagtcc   1200
tccggtctgt actccctctc ctccgtggtc accgtcccta gctcctccct gggcacccag   1260
acctacatct gcaacgtgaa ccacaagcct tccaacacca aggttgataa gaaggtggag   1320
ccgaagtcct gcgacaagac ccacacctgc taacaaattc ctgtgaagta gctgatttag   1380 tactttcgg aggtgtctat tcttaccaaa tcgtcaagtt gtgggtagag tcacctgaat    1440
attaattgca ccgcacgggt gatatatgct tatttgctca agtagttcga ggttaagtgt   1500
attttaggtg aacaaatttc agcttcgggt agaagacttt cgatgcgctt cagagcttct   1560
attgggaaat ctgacaccac ttgattaaat agcctacccc cgaattgggg gattggtcat   1620 ttttgctgt gaaggtagtt ttgatgcata tgacctgcgt ttataaagaa atgtaaacgt   1680
gatcagatcg atataaaga aacagtttgt actcaggttt gaagcatttt ctccgattcg   1740
cctggcaaaa atctcaattg tcgcttacag tttttctcaa cgacaggctg ctaagctgct   1800
agttcggtgg cctagtgagt ggcgtttact tggataaaag taatcccatg tcgtgatcag   1860 ccatttggg ttgtttccat agcaatccaa aggtttcgtc tttcgatacc tattcaagga   1920
gccttcgcct ctatgaaacg catgaaatcg ctggctgcgg cgctcaccgt cgctggggcc   1980
atgctggccg cacctgtggc aacggcagat atccagatga cccagtcccc atcctccctg   2040
tccgcttccg ttggtgaccg cgtgaccatc acctgccgtg catcccaggg catccgcaac   2100
tacctggctt ggtatcagca gaagccgggc aaggccccaa agctgctcat ctacgcagct   2160
tccaccctcc agtccggcgt gccttcccgt ttctccggct ccggttccgg caccgatttc   2220
accctgacca tctcctccct ccagcctgaa gatgtggcga cctactactg ccagcgttac   2280
aaccgtgcac cgtacacctt cggtcagggc accaaggttg aaatcaagcg taccgtggcc   2340
gcgccatccg tcttcatctt cccaccttcc gatgagcagc tgaagtccgg caccgcatcc   2400
gtggtctgcc tgctcaacaa cttctaccct cgcgaggcga aggtccagtg gaaggttgac   2460
aacgcactgc agtccggcaa ctcccaggaa tccgtgaccg agcaggattc caaggactcc   2520
acctactccc tctcctccac cctgaccctc tccaaggctg attacgaaaa gcacaaggtt   2580
tacgcctgcg aggtgaccca ccagggtctc tcctccccag tcaccaagtc cttcaaccgc   2640
```
ggcgaatgct aatctaga 2658

<210> SEQ ID NO 92
<211> LENGTH: 2658
<212> TYPE: DNA
<213> ORGANISM: Artificial Sequence
<220> FEATURE:
<223> OTHER INFORMATION: synthesized DNA

<400> SEQUENCE: 92

| | |
|---|---|
| ggatcccaaa ttcctgtgaa gtagctgatt tagtactttt cggaggtgtc tattcttacc | 60 |
| aaatcgtcaa gttgtgggta gagtcacctg aatattaatt gcaccgcacg ggtgatatat | 120 |
| gcttatttgc tcaagtagtt cgaggttaag tgtattttag gtgaacaaat tcagcttcg | 180 |
| ggtagaagac tttcgatgcg cttcagagct ctattggga atctgacac cacttgatta | 240 |
| aatagcctac ccccgaattg ggggattggt cattttttgc tgtgaaggta gttttgatgc | 300 |
| atatgacctg cgtttataaa gaatgtaaa cgtgatcaga tcgatataaa agaaacagtt | 360 |
| tgtactcagg tttgaagcat tttctccgat tcgcctggca aaaatctcaa ttgtcgctta | 420 |
| cagttttct caacgacagg ctgctaagct gctagttcgg tggcctagtg agtggcgttt | 480 |
| acttggataa aagtaatccc atgtcgtgat cagccatttt gggttgtttc catagcaatc | 540 |
| caaaggtttc gtctttcgat acctattcaa ggagccttcg cctctatgaa acgcatgaaa | 600 |
| tcgctggctg cggcgctcac cgtcgctggg gccatgctgg ccgcacctgt ggcaacggca | 660 |
| gatatccaga tgacccagtc ccatcctcc ctgtccgctt ccgttggtga ccgcgtgacc | 720 |
| atcacctgcc gtgcatccca gggcatccgc aactacctgg cttggtatca gcagaagccg | 780 |
| ggcaaggccc caaagctgct catctacgca gcttccaccc tccagtccgg cgtgccttcc | 840 |
| cgtttctccg gctccggttc cggcaccgat ttcaccctga ccatctcctc cctccagcct | 900 |
| gaagatgtgg cgacctacta ctgccagcgt tacaaccgtg caccgtacac cttcggtcag | 960 |
| ggcaccaagg ttgaaatcaa gcgtaccgtg gccgcgccat ccgtcttcat cttcccacct | 1020 |
| tccgatgagc agctgaagtc cggcaccgca tccgtggtct gcctgctcaa caacttctac | 1080 |
| cctcgcgagc gaaggtcca gtggaaggtt gacaacgcac tgcagtccgg caactcccag | 1140 |
| gaatccgtga ccgagcagga ttccaaggac tccacctact ccctctcctc caccctgacc | 1200 |
| ctctccaagg ctgattacga aaagcacaag gtttacgcct cgcgaggtgac ccaccagggt | 1260 |
| ctctcctccc cagtcaccaa gtccttcaac cgcggcgaat gctaacaaat tcctgtgaag | 1320 |
| tagctgattt agtactttc ggaggtgtct attcttacca aatcgtcaag ttgtgggtag | 1380 |
| agtcacctga atattaattg caccgcacgg gtgatatatg cttatttgct caagtagttc | 1440 |
| gaggttaagt gtattttagg tgaacaaatt cagcttcgg gtagaagact ttcgatgcgc | 1500 |
| ttcagagctt ctattgggaa atctgacacc acttgattaa atagcctacc cccgaattgg | 1560 |
| gggattggtc attttttgct gtgaaggtag ttttgatgca tatgacctgc gtttataaag | 1620 |
| aaatgtaaac gtgatcagat cgatataaaa gaaacagttt gtactcaggt ttgaagcatt | 1680 |
| ttctccgatt cgcctggcaa aaatctcaat tgtcgcttac agttttctc aacgacaggc | 1740 |
| tgctaagctg ctagttcggt ggcctagtga gtggcgttta cttggataaa agtaatccca | 1800 |
| tgtcgtgatc agccattttg ggttgtttcc atagcaatcc aaaggtttcg tctttcgata | 1860 |
| cctattcaag gagccttcgc ctctatgaaa cgcatgaaat cgctggctgc ggcgctcacc | 1920 |
| gtcgctgggg ccatgctggc cgcacctgtg gcaacggcag aagttcagct ggttgagtcc | 1980 |
| ggcggtggcc tggttcagcc aggtcgctcc ctgcgtctct cctgcgcagc ttccggcttc | 2040 |

```
accttcgatg actacgcaat gcactgggtt cgtcaggctc ctggcaaggg cctggaatgg    2100
gtgtccgcaa tcacctggaa ctccggtcac atcgattacg ctgactccgt cgagggccgc    2160
ttcaccatct cccgtgataa cgctaagaac tccctgtacc tccagatgaa ctccctccgt    2220
gcagaagaca ccgctgtcta ctactgcgca aaggtttcct acctgtccac cgcttcctcc    2280
ctcgattact ggggtcaggg caccctggtt accgtgtcct ccgcctccac caagggtcca    2340
tccgtgttcc cgctcgcacc atcctccaag tccacctccg gtggcaccgc cgcgctgggt    2400
tgcctcgtca aggactactt cccagaacct gtcaccgttt cctggaactc cggtgccctg    2460
acctccggtg tgcacacctt cccagcggtc ctccagtcct ccggtctgta ctccctctcc    2520
tccgtggtca ccgtccctag ctcctccctg gcacccagac ctacatctg caacgtgaac    2580 cacaagcctt ccaacaccaa ggttgataag aaggtggagc cgaagtcctg cgacaagacc    2640
cacacctgct aatctaga                                                   2658
```

<210> SEQ ID NO 93
<211> LENGTH: 693
<212> TYPE: DNA
<213> ORGANISM: Artificial Sequence
<220> FEATURE:
<223> OTHER INFORMATION: H chain of Adalimumab

<400> SEQUENCE: 93

```
gaagttcagc tggttgagtc cggcggtggc ctggttcagc aggtcgctc cctgcgtctc      60 tcctgcgcag cttccggctt caccttcgat gactacgcaa tgcactgggt tcgtcaggct    120
cctggcaagg gcctggaatg ggtgtccgca atcacctgga ctccggtca catcgattac    180 gctgactccg tcgagggccg cttcaccatc tcccgtgata cgctaagaa ctccctgtac    240 ctccagatga actccctccg tgcagaagac accgctgtct actactgcgc aaaggtttcc    300
tacctgtcca ccgcttcctc cctcgattac tggggtcagg gcaccctggt taccgtgtcc    360
tccgcctcca ccaagggtcc atccgtgttc ccgctcgcac catcctccaa gtccacctcc    420
ggtggcaccg ccgcgctggg ttgcctcgtc aaggactact cccagaacc tgtcaccgtt    480 tcctggaact ccggtgccct gacctccggt gtgcacacct tcccagcggt cctccagtcc    540
tccggtctgt actccctctc ctccgtggtc accgtcccta gctcctccct gggcacccag    600
acctacatct gcaacgtgaa ccacaagcct tccaacacca aggttgataa gaaggtggag    660
ccgaagtcct gcgacaagac ccacacctgc taa                                  693
```

<210> SEQ ID NO 94
<211> LENGTH: 230
<212> TYPE: PRT
<213> ORGANISM: Artificial Sequence
<220> FEATURE:
<223> OTHER INFORMATION: H chain of Adalimumab

<400> SEQUENCE: 94

```
Glu Val Gln Leu Val Glu Ser Gly Gly Gly Leu Val Gln Pro Gly Arg
1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60
```

-continued

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys
225             230

<210> SEQ ID NO 95
<211> LENGTH: 645
<212> TYPE: DNA
<213> ORGANISM: Artificial Sequence
<220> FEATURE:
<223> OTHER INFORMATION: L chain of Adalimumab

<400> SEQUENCE: 95

```
gatatccaga tgacccagtc cccatcctcc ctgtccgctt ccgttggtga ccgcgtgacc      60
atcacctgcc gtgcatccca gggcatccgc aactacctgg cttggtatca gcagaagccg     120
ggcaaggccc caaagctgct catctacgca gcttccaccc tccagtccgg cgtgccttcc     180
cgtttctccg gctccggttc cggcaccgat ttcaccctga ccatctcctc cctcagcct      240
gaagatgtgg cgacctacta ctgccagcgt acaaccgtg caccgtacac cttcggtcag     300
ggcaccaagg ttgaaatcaa gcgtaccgtg gccgcgccat ccgtcttcat cttcccacct     360
tccgatgagc agctgaagtc cggcaccgca tccgtggtct gcctgctcaa caacttctac     420
cctcgcgagg cgaaggtcca gtggaaggtt gacaacgcac tgcagtccgg caactcccag     480
gaatccgtga ccgagcagga ttccaaggac tccacctact ccctctcctc caccctgacc     540
ctctccaagg ctgattacga aaagcacaag gtttacgcct gcgaggtgac ccaccagggt     600
ctctcctccc cagtcaccaa gtccttcaac cgcggcgaat gctaa                    645
```

<210> SEQ ID NO 96
<211> LENGTH: 214
<212> TYPE: PRT
<213> ORGANISM: Artificial Sequence
<220> FEATURE:
<223> OTHER INFORMATION: L chain of Adalimumab

<400> SEQUENCE: 96

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr

```
                     20                  25                  30
Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
     210

<210> SEQ ID NO 97
<211> LENGTH: 1500
<212> TYPE: DNA
<213> ORGANISM: Corynebacterium glutamicum ATCC13869

<400> SEQUENCE: 97
atgtttaaca accgtatccg cactgcagct ctcgctggtg caatcgcaat ctccaccgca      60
gcttccggcg tagctatccc agcattcgct caggagacca acccaacctt caacatcaac     120
aacggcttca cgatgctga tggatccacc atccagccag ttgagccagt taaccacacc     180
gaggaaaccc tccgcgacct gactgactcc accggcgctt acctggaaga gttccagtac     240
ggcaacgttg aggaaatcgt tgaagcatac ctgcaggttc aggcttccgc agacggattc     300
gatccttctg agcaggctgc ttacgaggct ttcgaggctg ctcgcgttcg tgcatcccag     360
gagctcgcgg cttccgctga gaccatcact aagacccgcg agtccgttgc ttacgcactc     420
aaggctgacc gcgaagctac cgcagctttc gaggcttacc tcagcgctct tcgtcaggtt     480
tcagtcatca cgatctgat cgctgatgct aacgccaaga caagactga ctttgcagag      540
atcgagctct acgatgttct ttacaccgac gccgacatct tggcgatgc tccacttctt      600
gctcctgcat acaaggagct gaaggacctt caggctgagg ttgacgcaga cttcgagtgg     660
ttgggcgagt cgcaattga taacaatgaa gacaactacg tcattcgtac tcacatccct     720
gctgtagagg cactcaaggc agcgatcgat tcactggtcg acaccgttga gccacttcgt     780
gcagacgcta tcgctaagaa catcgaggct cagaagtctg acgttctggt tccccagctc     840
ttcctcgagc gtgcaactgc acagcgcgac accctgcgtg ttgtagaggc aatcttctct     900
acctctgctc gttacgttga actctacgag aacgtcgaga cgttaacgt tgagaacaag     960
acccttcgcc agcactactc ttccctgatc cctaacctct tcatcgcagc ggttggcaac    1020
```

-continued

```
atcaacgagc tcaacaatgc agatcaggct gcacgtgagc tcttcctcga ttgggacacc    1080
gacctcacca ccaacgatga ggacgaagct tactaccagg ctaagctcga cttcgctatc    1140
gagacctacg caaagatcct gatcaacggt gaagtttggc aggagccact cgcttacgtc    1200
cagaacctgg atgcaggcgc acgtcaggaa gcagctgacc gcgaagcaga gcgcgcagct    1260
gacgcagcat accgcgctga gcagctccgc atcgctcagg aagcagctga cgctcagaag    1320
gctctcgctg aggctcttgc taatgcaggc aacaacgaca acggtggcga caactcctcc    1380
gacgacaagg gaaccggttc ttccgacatc ggaacctggg accttttcgc agcaattgca    1440
gctatcatcg cagcaatcgc agctatcttc ccattcctct ccggtatcgt taagttctaa    1500
```

<210> SEQ ID NO 98
<211> LENGTH: 499
<212> TYPE: PRT
<213> ORGANISM: Corynebacterium glutamicum ATCC13869

<400> SEQUENCE: 98

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Asn Pro Thr Phe Asn Ile Asn Asn Gly Phe Asn Asp Ala Asp Gly
        35                  40                  45

Ser Thr Ile Gln Pro Val Glu Pro Val Asn His Thr Glu Glu Thr Leu
    50                  55                  60

Arg Asp Leu Thr Asp Ser Thr Gly Ala Tyr Leu Glu Glu Phe Gln Tyr
65                  70                  75                  80

Gly Asn Val Glu Glu Ile Val Glu Ala Tyr Leu Gln Val Gln Ala Ser
                85                  90                  95

Ala Asp Gly Phe Asp Pro Ser Glu Gln Ala Ala Tyr Glu Ala Phe Glu
            100                 105                 110

Ala Ala Arg Val Arg Ala Ser Gln Glu Leu Ala Ala Ser Ala Glu Thr
        115                 120                 125

Ile Thr Lys Thr Arg Glu Ser Val Ala Tyr Ala Leu Lys Ala Asp Arg
    130                 135                 140

Glu Ala Thr Ala Ala Phe Glu Ala Tyr Leu Ser Ala Leu Arg Gln Val
145                 150                 155                 160

Ser Val Ile Asn Asp Leu Ile Ala Asp Ala Asn Ala Lys Asn Lys Thr
                165                 170                 175

Asp Phe Ala Glu Ile Glu Leu Tyr Asp Val Leu Tyr Thr Asp Ala Asp
            180                 185                 190

Ile Ser Gly Asp Ala Pro Leu Leu Ala Pro Ala Tyr Lys Glu Leu Lys
        195                 200                 205

Asp Leu Gln Ala Glu Val Asp Ala Asp Phe Glu Trp Leu Gly Glu Phe
    210                 215                 220

Ala Ile Asp Asn Asn Glu Asp Asn Tyr Val Ile Arg Thr His Ile Pro
225                 230                 235                 240

Ala Val Glu Ala Leu Lys Ala Ala Ile Asp Ser Leu Val Asp Thr Val
                245                 250                 255

Glu Pro Leu Arg Ala Asp Ala Ile Ala Lys Asn Ile Glu Ala Gln Lys
            260                 265                 270

Ser Asp Val Leu Val Pro Gln Leu Phe Leu Glu Arg Ala Thr Ala Gln
        275                 280                 285
```

```
Arg Asp Thr Leu Arg Val Val Glu Ala Ile Phe Ser Thr Ser Ala Arg
    290                 295                 300

Tyr Val Glu Leu Tyr Glu Asn Val Glu Asn Val Asn Val Glu Asn Lys
305                 310                 315                 320

Thr Leu Arg Gln His Tyr Ser Ser Leu Ile Pro Asn Leu Phe Ile Ala
                325                 330                 335

Ala Val Gly Asn Ile Asn Glu Leu Asn Asn Ala Asp Gln Ala Ala Arg
            340                 345                 350

Glu Leu Phe Leu Asp Trp Asp Asp Leu Thr Thr Asn Asp Glu Asp
        355                 360                 365

Glu Ala Tyr Tyr Gln Ala Lys Leu Asp Phe Ala Ile Glu Thr Tyr Ala
    370                 375                 380

Lys Ile Leu Ile Asn Gly Glu Val Trp Gln Glu Pro Leu Ala Tyr Val
385                 390                 395                 400

Gln Asn Leu Asp Ala Gly Ala Arg Gln Glu Ala Ala Asp Arg Glu Ala
                405                 410                 415

Glu Arg Ala Ala Asp Ala Ala Tyr Arg Ala Glu Gln Leu Arg Ile Ala
            420                 425                 430

Gln Glu Ala Ala Asp Ala Gln Lys Ala Leu Ala Glu Ala Leu Ala Asn
        435                 440                 445

Ala Gly Asn Asn Asp Asn Gly Gly Asp Asn Ser Ser Asp Asp Lys Gly
    450                 455                 460

Thr Gly Ser Ser Asp Ile Gly Thr Trp Gly Pro Phe Ala Ala Ile Ala
465                 470                 475                 480

Ala Ile Ile Ala Ala Ile Ala Ala Ile Phe Pro Phe Leu Ser Gly Ile
                485                 490                 495

Val Lys Phe

<210> SEQ ID NO 99
<211> LENGTH: 25
<212> TYPE: DNA
<213> ORGANISM: Artificial Sequence
<220> FEATURE:
<223> OTHER INFORMATION: primer

<400> SEQUENCE: 99
agctcgtgcg cacctatccg ctgga                                           25

<210> SEQ ID NO 100
<211> LENGTH: 25
<212> TYPE: DNA
<213> ORGANISM: Artificial Sequence
<220> FEATURE:
<223> OTHER INFORMATION: primer

<400> SEQUENCE: 100
ggtcaacgca gcgggttccg cgcca                                           25
```

METHOD FOR SECRETORY PRODUCTION OF PROTEIN

This application is a Continuation of, and claims priority under 35 U.S.C. §120 to, International Application No. PCT/JP2012/078906, filed Nov. 1, 2012, and claims priority therethrough under 35 U.S.C. §119 to Russian Patent Application No. 2011144497, filed Nov. 2, 2011, and Japanese Patent Application No. 2011-240745, filed Nov. 2, 2011, the entireties of which are incorporated by reference herein. Also, the Sequence Listing filed electronically herewith is hereby incorporated by reference (File name: 2014-04-29T_US-509_Seq_List; File size: 57 KB; Date recorded: Apr. 29, 2014).

BACKGROUND OF THE INVENTION

1. Field of the Invention

The present invention relates to a coryneform bacterium that is able to efficiently produce a heterologous protein by secretion, and a method for secretory production of a heterologous protein.

2. Brief Description of the Related Art

To date, secretory production of heterologous proteins by microorganisms has been reported in *Bacillus* bacterium (Microbiol. rev., 57, 109-137 (1993)), methanol-assimilating yeast, *Pichia pastoris* (Biotechnol., 11, 905-910 (1993)), filamentous fungi of the genus *Aspergillus* (Biotechnol., 6, 1419-1422 (1988) and Biotechnol., 9, 976-981 (1991)), and so forth.

Secretory production of heterologous proteins by coryneform bacteria has also been reported, specifically secretion of a nuclease and a lipase by *Corynebacterium glutamicum* (henceforth also abbreviated as *C. glutamicum*) (U.S. Pat. No. 4,965,197 and J. Bacteriol., 174, 1854-1861 (1992)), secretion of a protease such as subtilisin (Appl. Environ. Microbiol., 61, 1610-1613 (1995)), secretion of a protein using signal peptides of cell surface layer proteins PS1 and PS2 (also referred to as CspB) of coryneform bacteria (Japanese Patent Laid-open (Kohyo) No. 6-502548), secretion of a fibronectin-binding protein using the signal peptide of PS2 (CspB) (Appl. Environ. Microbiol., 63, 4392-4400 (1997)), secretion of protransglutaminase using signal peptides of cell surface layer proteins PS2 (CspB) and SlpA (also referred to as CspA) of coryneform bacteria (Japanese Patent No. 4320769), secretion of a protein using a variant type secretion system (Japanese Patent Laid-open (Kokai) No. 11-169182), secretion of a protransglutaminase by a variant strain (Japanese Patent No. 4362651), secretion of a protein using a Tat-dependent signal peptide (Japanese Patent No. 4730302), and so forth.

Various proteins have been suggested as proteins which could be produced by secretory production; however, in coryneform bacteria, there are no reports of secretory production of any multimeric protein, such as, for example, antibody-related molecules.

Penicillin-binding protein (PBP) is a generic term which describes proteins that bind with β-lactam type antibiotics, and as a result, inhibit binding with β-lactam type antibiotics. PBPs are generally membrane-binding proteins, and they are considered essential for cell wall synthesis of eubacteria. PBPs are classified as high molecular weight PBPs (HMW-PBPs) or low molecular weight PBPs (LMW-PBPs), according to their molecular weights. HMW-PBPs are further classified as class A high molecular weight PBPs (class A HMW-PBPs), which have both a transpeptidase activity domain for crosslinking peptidoglycan moieties, and a transglycosylase activity domain for forming a polysaccharide chain from disaccharides, and class B high molecular weight PBPs (class B HMW-PBPs) which have only a transpeptidase activity domain.

The findings about PBPs of *C. glutamicum* are detailed in Mol. Microbiol., 66, 643-57 (2007), Antonie Van Leeuwenhoek, 94, 99-109 (2008), Mol. Microbiol., 9, 97-109 (1993), and J. Biotechnol., 112, 177-193 (2004). In *C. glutamicum*, at least nine PBP homologues have been found so far. Five of them are HMW-PBPs including two class A HMW-PBPs (PBP1a, PBP1b), and three class B HMW-PBPs (FtsI, PBP2a, PBP2b). It is known that the class A HMW-PBPs of *C. glutamicum* are responsible for cell extension, and the class B HMW-PBPs are responsible for formation of peptidoglycan of septal walls at the time of cell division.

Cell surface layer proteins are proteins constituting the cell surface layers (S-layers) of bacteria and archaea. As the cell surface layer proteins of coryneform bacteria, PS1 and PS2 (CspB) of *C. glutamicum* (Mol. Microbiol., 9, 97-109 (1993)), SlpA (CspA) of *C. stationis* (Japanese Patent Laid-open (Kohyo) No. 6-502548), and so forth are known. Regarding PS2 (CspB), for example, amino acid sequences of CspB homologues of 28 strains of *C. glutamicum* have been reported (J. Biotechnol., 112, 177-193 (2004)). As described above, signal peptides of cell surface layer proteins of coryneform bacteria are utilized in secretory productions of proteins (Japanese Patent Laid-open (Kohyo) No. 6-502548; Japanese Patent No. 4320769, and so forth).

However, the relationship between the decrease in the activity of a penicillin-binding protein and/or the decrease in the activity of a cell surface layer protein, and the secretory production of a heterologous protein has not been previously reported.

SUMMARY OF THE INVENTION

Aspects to be Achieved by the Invention

An aspect of the present invention is to develop a novel technique for improving the ability of a coryneform bacterium to produce a heterologous protein by secretory production, and thereby to provide a coryneform bacterium that produces a heterologous protein by secretory production and a method for secretory production of a heterologous protein using such a bacterium.

A method for producing a heterologous protein is described that utilizes a coryneform bacterium as an expression host. The ability of the coryneform bacterium to produce a heterologous protein by secretory production is improved by deleting the gene coding for the penicillin-binding protein PBP1a and the gene coding for the cell surface layer protein CspB of the coryneform bacterium.

It is an aspect of the present invention to provide a coryneform bacterium having an ability to produce a heterologous protein by secretory production, wherein said bacterium is modified to have reduced activities of both a penicillin-binding protein and a cell surface layer protein, and wherein the amount of the heterologous protein produced by secretory production is increased compared with that observed for a non-modified strain.

It is a further aspect of the present invention to provide the bacterium as described above, wherein the bacterium is modified by attenuating expression of a gene coding for the penicillin-binding protein or disrupting a gene coding for the penicillin-binding protein.

It is a further aspect of the present invention to provide the bacterium as described above, wherein the penicillin-binding protein is PBP1a.

It is a further aspect of the present invention to provide the bacterium as described above, wherein the penicillin-binding protein is selected from the group consisting of:

(A) a protein comprising the amino acid sequence of SEQ ID NO: 82, (B) a protein comprising an amino acid sequence of SEQ ID NO: 82, but which includes substitution, deletion, insertion, or addition of 1 to 10 amino acid residues, and wherein said protein has a property that if the protein activity is reduced in the coryneform bacterium, the amount of the heterologous protein produced by secretory production is increased compared with that observed for a non-modified strain.

It is a further aspect of the present invention to provide the bacterium as described above, which has been modified so that the activity of the cell surface layer protein is reduced by attenuating expression of a gene coding for the cell surface layer protein or disrupting the gene.

It is a further aspect of the present invention to provide the bacterium as described above, wherein the cell surface layer protein is CspB.

It is a further aspect of the present invention to provide the bacterium as described above, wherein the cell surface layer protein is selected from the group consisting of:

A) a protein comprising the amino acid sequence of SEQ ID NO: 98,

B) a protein comprising an amino acid sequence of SEQ ID NO: 98, but includes substitution, deletion, insertion, or addition of 1 to 10 amino acid residues, and wherein said protein has a property that if the protein activity is reduced in the coryneform bacterium, the amount of the heterologous protein produced by secretory production is increased compared with that observed for a non-modified strain.

It is a further aspect of the present invention to provide the bacterium as described above, which belongs to the genus *Corynebacterium* or *Brevibacterium*.

It is a further aspect of the present invention to provide the bacterium as described above, which is *Corynebacterium glutamicum*.

It is a further aspect of the present invention to provide the bacterium as described above, wherein the coryneform bacterium has a genetic construct for secretory expression of the heterologous protein, and wherein the genetic construct comprises a promoter sequence that functions in the coryneform bacterium, a nucleic acid sequence coding for a signal peptide that functions in the coryneform bacterium, which is ligated downstream from the promoter sequence, and a nucleic acid sequence coding for the heterologous protein, which is ligated downstream from the nucleic acid sequence coding for the signal peptide.

It is a further aspect of the present invention to provide the bacterium as described above, wherein the heterologous protein is an antibody-related molecule.

It is a further aspect of the present invention to provide the bacterium as described above, wherein the antibody-related molecule is selected from the group consisting of Fab, F(ab')$_2$, an Fc-fusion protein, scFv, and combinations thereof.

It is a further aspect of the present invention to provide a method for producing a heterologous protein, which comprises culturing the coryneform bacterium mentioned above and collecting the heterologous protein produced by secretory production.

DESCRIPTION OF THE PREFERRED EMBODIMENTS

<1> Coryneform Bacterium

Figure 1:
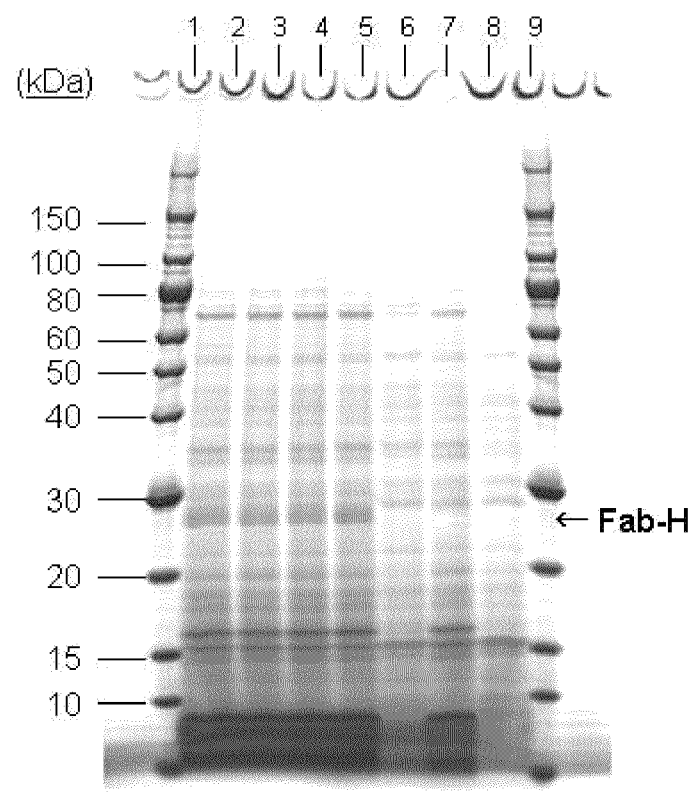
FIG. 1 is a photograph showing the results of reduced SDS-PAGE of the H chain region of the Fab fragment of trastuzumab expressed in the YDK010 strain (parent strain) and the YDK010ΔPBP1a strain.

The present invention provides a coryneform bacterium having an ability to produce a heterologous protein by secretory production, in that the bacterium has been modified to have reduced activities of both a penicillin-binding protein and a cell surface layer protein (henceforth also referred to as the "bacterium of the present invention" or the "coryneform bacterium of the present invention").

The expression that a protein is "secreted" can mean that the protein is transported out of the bacterial cell, that is, extracellularly transported. The expression that a protein is "secreted" of course can include when all the protein molecules are present in the medium in completely free forms, when all the protein molecules are present in the cell surface layer, and/or when some of the protein molecules are present in the medium and some are present in the cell surface layer.

That is, the "ability to produce a heterologous protein by secretory production" can refer to an ability of the bacterium of the present invention to secrete the heterologous protein into the medium or the cell surface layer, and allow it to accumulate in the medium or the cell surface layer to such an extent that the heterologous protein can be collected from the medium or the cell surface layer, when the bacterium is cultured in the medium. As for the amount that can be accumulated, for example, 10 μg/L or more, 1 mg/L or more, 100 mg/L or more, or even 1 g/L or more can be possible. Also, the amount that can be accumulated in the cell surface layer can be to such an extent that if the heterologous protein in the cell surface layer is collected and suspended in the same volume of liquid as the medium, the concentration of the heterologous protein in the suspension can be 10 μg/L or more, 1 mg/L or more, 100 mg/L or more. In addition, the term "protein" produced by secretory production can refer to molecules called a peptide or polypeptide.

The "heterologous protein" can refer to an exogenous protein relative to the coryneform bacterium that expresses and secretes that protein. The heterologous protein may be, for example, a protein derived from a microorganism, a protein derived from a plant, a protein derived from an animal, a protein derived from a virus, or even a protein with an artificially designed amino acid sequence. The heterologous protein may be a monomer protein or a multimeric protein. The multimeric protein can contain two or more subunits. In the multimer, the subunits may be linked by covalent bonds such as disulfide bonds, linked by non-covalent bonds such as hydrogen bonds and hydrophobic interaction, or linked by combination of these. The multimer can include one or more intermolecular disulfide bonds. The multimer can be a homo-multimer consisting of a single kind of subunit, or may be a hetero-multimer consisting of two or more kinds of subunits. For the hetero-multimer, it is sufficient that at least one subunit is a heterologous protein. That is, all the subunits may be heterogenous, or only a part of subunits may be heterogenous. Although the heterologous protein may be a secretory protein in nature, or may be a non-secretory protein in nature, it is preferably a secretory protein in nature. Specific examples of the "heterologous protein" are described herein.

The heterologous protein can be a single kind of protein, or two or more kinds of proteins. Moreover, when the heterologous protein is a hetero-multimer, only one kind of subunit may be produced, or two or more kinds of subunits may be produced. That is, the "secretory production of the heterologous protein" includes secretory production of all the subunits constituting a target heterologous protein, as well as secretory production of only a part of the subunits constituting a target heterologous protein.

The coryneform bacteria are aerobic gram-positive bacilli, and include *Corynebacterium* bacteria, *Brevibacterium* bacteria, *Microbacterium* bacteria, and so forth. The coryneform bacteria include bacteria which have previously been classified into the genus *Brevibacterium*, but are presently united into the genus *Corynebacterium* (Int. J. Syst. Bacteriol., 41, 255 (1991)). The coryneform bacteria also include bacteria which have previously been classified into *Corynebacterium ammoniagenes* but are presently reclassified into *Corynebacterium stationis* by nucleotide sequence analysis of 16S rRNA and so forth (Int. J. Syst. Evol. Microbiol., 60, 874-879 (2010)). Advantages of using coryneform bacteria include the fact that they inherently secrete an extremely small amount of proteins to the outside of cells compared with fungi, yeasts, and *Bacillus* bacteria, which are conventionally used for secretory production of proteins, and therefore the purification process of a heterologous protein produced by secretory production can be simplified or eliminated. Another advantage is the fact that they can grow well in a simple medium containing a saccharide, ammonia, mineral salts, etc., and therefore they are excellent in view of cost of medium, culture method, and culture productivity, and so forth.

Specific examples of such coryneform bacteria include the following species:
Corynebacterium acetoacidophilum
Corynebacterium acetoglutamicum
Corynebacterium alkanolyticum
Corynebacterium callunae
Corynebacterium glutamicum
Corynebacterium lilium
Corynebacterium melassecola
Corynebacterium thermoaminogenes (Corynebacterium efficiens)
Corynebacterium herculis
Brevibacterium divaricatum
Brevibacterium flavum
Brevibacterium immariophilum
Brevibacterium lactofermentum (Corynebacterium glutamicum)
Brevibacterium roseum
Brevibacterium saccharolyticum
Brevibacterium thiogenitalis
Corynebacterium ammoniagenes (Corynebacterium stationis)
Brevibacterium album
Brevibacterium cerinum
Microbacterium ammoniaphilum Specific examples of such coryneform bacteria include the following strains:
Corynebacterium acetoacidophilum ATCC 13870
Corynebacterium acetoglutamicum ATCC 15806
Corynebacterium alkanolyticum ATCC 21511
Corynebacterium callunae ATCC 15991
Corynebacterium glutamicum ATCC 13020, ATCC 13032, ATCC 13060, ATCC 13869, FERM BP-734
Corynebacterium lilium ATCC 15990
Corynebacterium melassecola ATCC 17965
Corynebacterium thermoaminogenes AJ12340 (FERM BP-1539)
Corynebacterium herculis ATCC 13868
Brevibacterium divaricatum ATCC 14020
Brevibacterium flavum ATCC 13826, ATCC 14067, AJ12418 (FERM BP-2205)
Brevibacterium immariophilum ATCC 14068
Brevibacterium lactofermentum ATCC 13869
Brevibacterium roseum ATCC 13825
Brevibacterium saccharolyticum ATCC 14066
Brevibacterium thiogenitalis ATCC 19240
Corynebacterium ammoniagenes (Corynebacterium stationis) ATCC 6871, ATCC 6872
Brevibacterium album ATCC 15111
Brevibacterium cerinum ATCC 15112
Microbacterium ammoniaphilum ATCC 15354

These strains are available from, for example, the American Type Culture Collection (ATCC) (Address: 12301 Parklawn Drive, Rockville, Md. 20852, P.O. Box 1549, Manassas, Va. 20108, United States of America). That is, each strain is given a unique registration number (www.atcc.org), and can be ordered by using this registration number. The registration number of each strain is listed in the catalogue of the ATCC.

In particular, the *C. glutamicum* AJ12036 strain (FERM BP-734), which was isolated from the wild-type strain *C. glutamicum* ATCC 13869, as a streptomycin (Sm) resistant mutant strain, is predicted to have a mutation in the functional gene responsible for secretion of proteins, and shows an extremely high secretory production ability for proteins as high as about 2 to 3 times in terms of the accumulated amount of proteins under optimum culture conditions, compared with the parent strain (wild-type strain), and therefore it is preferred as a host bacterium. The AJ12036 strain (FERM BP-734) was originally deposited at the National Institute of Bioscience and Human-Technology, Agency of Industrial Science and Technology (the independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Mar. 26, 1984 as an international deposit, and assigned an accession number of FERM BP-734.

Moreover, a strain having an enhanced ability to produce a protein by secretory production may be selected from coryneform bacteria obtained from such coryneform bacteria as mentioned above as a parent strain by using a mutagenesis method or a genetic recombination method, and used as a host. For example, after a parent strain is treated with ultraviolet irradiation or a chemical mutation agent such as N-methyl-N'-nitrosoguanidine, a strain having an enhanced ability to produce a protein by secretory production can be selected.

Furthermore, if a strain obtained by modifying such a strain as mentioned above so that it does not produce a cell surface layer protein as the host, purification of the heterologous protein secreted in the medium becomes easy, and therefore it is particularly preferred. Such modification can be carried out by introducing a mutation into the coding region of the cell surface layer protein or an expression control region thereof, on the chromosome by mutagenesis or genetic recombination. Examples of coryneform bacterium modified so that it does not produce a cell surface layer protein can include the *C. glutamicum* YDK010 strain (WO2004/029254), which is deficient in a cell surface layer protein PS2, and is derived from *C. glutamicum* AJ12036 strain (FERM BP-734).

The coryneform bacterium having an ability to produce a heterologous protein by secretory production can be obtained by introducing a genetic construct for secretory expression of the heterologous protein into such a coryneform bacterium as mentioned above so that the construct is harbored by the bacterium. That is, the bacterium of the present invention has a genetic construct for secretory expression of a heterologous protein. The "genetic construct for secretory expression of a heterologous protein" and a method for introducing it is described herein.

The bacterium of the present invention can be obtained by modifying a coryneform bacterium that is able to produce a heterologous protein by secretory production so that the activity of a penicillin-binding protein and the activity of a cell surface layer protein are reduced. Alternatively, the bacterium of the present invention can also be obtained by modifying a coryneform bacterium so that the activity of a penicillin-binding protein and the activity of a cell surface layer protein are both reduced, and then imparting the ability to produce a heterologous protein by secretory production to the bacterium. Furthermore, the bacterium of the present invention can also be obtained by modifying a coryneform bacterium that inherently has reduced activity of a cell surface layer protein so that the bacterium additionally is able to produce a heterologous protein and the activity of a penicillin-binding protein is reduced. In the present invention, the modification and impartation of the ability for constructing the bacterium of the present invention can be carried out in an arbitrary order. The bacterium of the present invention may be a bacterium obtained from a bacterium that can produce a heterologous protein by secretory production before it is modified so that the activity of a penicillin-binding protein and/or the activity of a cell surface layer protein are reduced. In addition, the bacterium of the present invention may also be a bacterium that cannot produce a heterologous protein by secretory production even when it has a genetic construct for secretory expression of a heterologous protein before it is modified so that the activity of a penicillin-binding protein and/or the activity of a cell surface layer protein are reduced, which is then able to produce the heterologous protein by secretory production as a result of reducing the activity of the penicillin-binding protein and/or the activity of a cell surface layer protein. In addition, the bacterium of the present invention may be further modified so that expression of a gene encoding a metallopeptidase or a gene encoding a protein having a region homologous to a motif of a metallopeptidase is increased.

Hereafter, penicillin-binding proteins and genes coding for them will be explained.

In general, the penicillin-binding proteins (PBPs) can refer to proteins that bind with β-lactam type antibiotics, and as a result, inhibit their enzymatic function. The penicillin-binding proteins include high molecular weight PBPs (HMW-PBPs) and low molecular weight PBPs (LMW-PBPs). The high molecular weight PBPs include class A high molecular weight PBPs (class A HMW-PBPs) and class B high molecular weight PBPs (class B HMW-PBPs). The class A HMW-PBPs have both a transpeptidase activity domain for crosslinking peptidoglycan moieties and a transglycosylase activity domain for forming a polysaccharide chain from disaccharides. The class B HMW-PBPs have a transpeptidase activity domain. For example, as for *C. glutamicum*, PBP1a and PBP1b can be mentioned as the class A HMW-PBPs. As for *C. glutamicum*, FtsI, PBP2a, and PBP2b can be mentioned as the class B HMW-PBPs.

When the activity of a penicillin-binding protein is reduced in a coryneform bacterium, the amount of a heterologous protein produced by secretory production is increased as compared with that observed for a non-modified strain. Examples of a penicillin-binding protein, for example, include PBP 1a, class B HMW-PBPs, and LMW-PBPs, specifically include PBP1a and class B HMW-PBPs, or more specifically include PBP1a.

The phrase regarding the "property that if the activity of the protein is reduced in a coryneform bacterium, the amount of a heterologous protein to be produced by secretory production is increased compared with that observed for a non-modified strain" can refer to a property that if the activity of the protein is reduced in a coryneform bacterium, an ability to produce a heterologous protein by secretory production in an amount larger than that observed for a non-modified strain such as wild-type strain or parent strain is imparted to the coryneform bacterium. Although the degree of the increase in amount of the heterologous protein to be produced by secretory production is not particularly limited so long as the amount of the heterologous protein produced by secretory production increases compared with that observed for a non-modified strain, the amount to be produced can mean, for example, 10% or more, 20% or more, 30% or more, 100% or more, in terms of the accumulation amount in the medium and/or the cell surface layer. In addition, to produce a heterologous protein by secretory production in an amount larger than that observed for a non-modified strain may mean that whereas the heterologous protein cannot be detected when non-concentrated culture supernatant of a non-modified strain is applied to SDS-PAGE and stained with CBB, the heterologous protein can be detected when non-concentrated culture supernatant of a modified strain is applied to SDS-PAGE and stained with CBB.

Also, the phrase regarding the "property that if the activity of the protein is reduced in a coryneform bacterium, the amount of a heterologous protein to be produced by secretory production is increased compared with that observed for a non-modified strain" regarding a penicillin-binding protein can also include a property that if the activity of the protein is reduced in a strain in which the activity of a cell surface layer protein is not reduced, the ability of the strain to produce a heterologous protein by secretory production is not increased, however, if the activity of the protein is reduced in a strain in which the activity of a cell surface layer protein is reduced, the ability of the strain to produce a heterologous protein by secretory production is increased.

Whether a protein has a property that if the activity of the protein is reduced in a coryneform bacterium, the amount of a heterologous protein produced by secretory production is increased compared with that observed for a non-modified strain can be confirmed by modifying a coryneform bacterium so that the activity of the protein is reduced, quantifying the amount of the heterologous protein produced by secretory production observed when the modified strain is cultured in a medium, and comparing the quantified amount with the amount of the heterologous protein produced by secretory production observed when an unmodified strain is cultured in the medium.

The Cgl0278 gene coding for the PBP1a protein of the *C. glutamicum* ATCC 13032 corresponds to a sequence complementary to the sequence of the 294001 to 296388 positions in the genome sequence registered at the NCBI database as GenBank accession BA000036 (VERSION BA000036.3 GI: 42602314). Also, the PBP1a protein of the *C. glutamicum* ATCC 13032 is registered as GenBank accession NP_599531 (version NP_599531.1 GI: 19551529, locus_tag="NCgl0274"). The nucleotide sequence of the Cgl0278 gene of *C. glutamicum* ATCC 13032 and the amino acid sequence of the PBP1a protein encoded by this gene are shown as SEQ ID NOS: 81 and 82, respectively.

Since a nucleotide sequence of a gene coding for a penicillin-binding protein may differ depending on species or strain to which the coryneform bacterium belongs, the gene coding for a penicillin-binding protein may be a variant of the aforementioned nucleotide sequence, so long as the gene codes for a protein having a property that if the activity of the protein is reduced in a coryneform bacterium, the amount of a heterologous protein to be produced by secretory production is increased compared with that observed for a non-modified strain. In addition, the variant of the Cgl0278 gene includes a homologue of the gene. Homologues of the Cgl0278 gene can be easily obtained from public databases by BLAST search or FASTA search using the wild-type Cgl0278 gene of the aforementioned *C. glutamicum* as a query sequence, and can also be obtained by PCR using a chromosome of a coryneform bacterium as a template and oligonucleotides prepared on the basis of a known gene sequence such as those mentioned above as primers.

The gene coding for a penicillin-binding protein may be a gene coding for a protein having the aforementioned amino acid sequence including substitution, deletion, insertion, or addition of one or several amino acid residues at one or several positions, so long as the gene codes for a protein having a property that if the activity of the protein is reduced in a coryneform bacterium, the amount of a heterologous protein to be produced by secretory production is increased compared with that observed for a non-modified strain. In such a case, usually 70% or more, 80% or more, 90% or more, of the above-defined property that if the activity of the protein is reduced in a coryneform bacterium, the amount of a heterologous protein produced by secretory production is increased compared with that observed for a non-modified strain is maintained based on the same protein but without with the above substitution, deletion, insertion, or addition of one or several amino acid residues. Although the number of the "one or several" amino acid residues may differ depending on the position in the three-dimensional structure or types of amino acid residues of the protein, specifically, it can be 1 to 20, 1 to 10, 1 to 5.

The aforementioned substitution, deletion, insertion, or addition of one or several amino acid residues can be a conservative mutation that maintains the normal function of the protein. Typical examples of conservative mutations are conservative substitutions. The conservative substitution can be a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, inversion or the like of amino acid residues as mentioned above can include a naturally occurring mutation due to an individual difference, or a difference of species of a bacterium from which the gene is derived (mutant or variant).

Furthermore, the gene having such a conservative mutation as mentioned above may be a gene coding for a protein having a homology of 80% or more, 90% or more, 95% or more, 97% or more, 99% or more, to the total encoded amino acid sequence and having a property that if the activity of the protein is reduced in a coryneform bacterium, the amount of a heterologous protein produced by secretory production is increased compared with that observed for a non-modified strain. In addition, in this specification, "homology" may mean "identity".

Moreover, the gene coding for a penicillin-binding protein may be a DNA that is able to hybridize with a probe that can be prepared from a known gene sequence, for example, a sequence complementary to a part or all of the aforementioned nucleotide sequence, under stringent conditions, and coding for a protein having a property that if the activity of the protein is reduced in a coryneform bacterium, the amount of a heterologous protein to be produced by secretory production is increased compared with that observed for a non-modified strain. The "stringent conditions" can refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, not less than 99% homologous, hybridize to each other, and DNAs less homologous than the above do not hybridize to each other, or conditions of a typical Southern hybridization, i.e., conditions of washing once, preferably 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing the nucleotide sequence as a template. For example, when a DNA fragment having a length of about 300 bp is used as the probe, the washing conditions of the hybridization may be, for example, 50° C., 2×SSC and 0.1% SDS.

In addition, the aforementioned explanations concerning variants of genes and proteins can also be applied mutatis mutandis to arbitrary proteins such as a cell surface layer protein and a heterologous protein to be produced by secretory production in the present invention, and genes coding for them.

Hereafter, cell surface layer proteins and genes coding for them will be explained.

The cell surface layer proteins are proteins constituting the cell surface layers (S-layer) of bacteria and archaea. Examples of the cell surface layer proteins of coryneform bacteria can include PS1 and PS2 (also referred to as CspB) of *C. glutamicum* and SlpA (also referred to as CspA) of *C. stationis*. Among them, it is preferred that the activity of PS2 protein is reduced.

The nucleotide sequence of the cspB gene of *C. glutamicum* ATCC 13869 and the amino acid sequence of the PS2 protein encoded by this gene are shown as SEQ ID NOS: 97 and 98, respectively.

Also, for example, amino acid sequences of CspB homologues regarding 28 strains of *C. glutamicum* have been reported (J. Biotechnol., 112, 177-193 (2004)). These 28 strains of *C. glutamicum* and the GenBank accession numbers of the cspB gene homologues in NCBI database are exemplified below (the GenBank accession numbers are shown in the parentheses).

*C. glutamicum* ATCC13058 (AY524990)
*C. glutamicum* ATCC13744 (AY524991)
*C. glutamicum* ATCC13745 (AY524992)
*C. glutamicum* ATCC14017 (AY524993)
*C. glutamicum* ATCC14020 (AY525009)
*C. glutamicum* ATCC14067 (AY524994)
*C. glutamicum* ATCC14068 (AY525010)
*C. glutamicum* ATCC14747 (AY525011)
*C. glutamicum* ATCC14751 (AY524995)
*C. glutamicum* ATCC14752 (AY524996)
*C. glutamicum* ATCC14915 (AY524997)
*C. glutamicum* ATCC15243 (AY524998)
*C. glutamicum* ATCC15354 (AY524999)
*C. glutamicum* ATCC17965 (AY525000)
*C. glutamicum* ATCC17966 (AY525001)
*C. glutamicum* ATCC19223 (AY525002)
*C. glutamicum* ATCC19240 (AY525012)
*C. glutamicum* ATCC21341 (AY525003)
*C. glutamicum* ATCC21645 (AY525004)
*C. glutamicum* ATCC31808 (AY525013)
*C. glutamicum* ATCC31830 (AY525007)
*C. glutamicum* ATCC31832 (AY525008)
*C. glutamicum* LP-6 (AY525014)
*C. glutamicum* DSM20137 (AY525015)
*C. glutamicum* DSM20598 (AY525016)
*C. glutamicum* DSM46307 (AY525017)
*C. glutamicum* 22220 (AY525005)
*C. glutamicum* 22243 (AY525006)

Since nucleotide sequence of a gene coding for a cell surface layer protein may differ depending on species or strain to which the coryneform bacterium belongs, the gene coding for a cell surface layer protein may be a variant of the aforementioned nucleotide sequence, so long as the gene codes for a protein having a property that if the activity of the protein is reduced in a coryneform bacterium, the amount of a heterologous protein produced by secretory production is increased compared with that observed for a non-modified strain. For example, the gene coding for a cell surface layer protein may be a gene coding for a protein having the aforementioned amino acid sequence including substitution, deletion, insertion, or addition of one or several amino acid residues at one or several positions, so long as the gene codes for a protein having a property that if the activity of the protein is reduced in a coryneform bacterium, the amount of a heterologous protein produced by secretory production is increased compared with that observed for a non-modified strain. The aforementioned explanations concerning variants of a penicillin-binding protein and a gene encoding it can also be applied mutatis mutandis to variants of a cell surface layer protein and a gene encoding it.

Also, the phrase regarding the "property that if the activity of the protein is reduced in a coryneform bacterium, the amount of a heterologous protein to be produced by secretory production is increased compared with that observed for a non-modified strain" regarding a cell surface layer protein can include when the activity of the protein is reduced and the penicillin-binding protein activity is not reduced, the ability of the strain to produce a heterologous protein by secretory production is not increased. However, when the activity of the protein is reduced in a strain in which the activity of a penicillin-binding protein is also reduced, the ability of the strain to produce a heterologous protein by secretory production can be increased.

The expression "activity of a cell surface layer protein is reduced" or "reduced activity of a cell surface layer protein" can include the situation when a coryneform bacterium has been modified so that the activity of a cell surface layer protein is reduced, and when the activity of a cell surface layer protein is inherently reduced in a coryneform bacterium. The "case where the activity of a cell surface layer protein is inherently reduced in a coryneform bacterium" can include when a coryneform bacterium is inherently deficient in a cell surface layer protein. That is, examples of a coryneform bacterium in which the activity of a cell surface layer protein is reduced can include a coryneform bacterium that is inherently deficient in a cell surface layer protein. Examples of the "case where a coryneform bacterium is inherently deficient in a cell surface layer protein" can include when a coryneform bacterium is inherently deficient in a gene encoding a cell surface layer protein. The expression "a coryneform bacterium is inherently deficient in a cell surface layer protein" can mean that a coryneform bacterium is inherently deficient in one or more proteins selected from cell surface layer protein(s) found in other strain(s) of the species to which the coryneform bacterium belongs. For example, "*C. glutamicum* is inherently deficient in a cell surface layer protein" can mean that a *C. glutamicum* strain is inherently deficient in one or more proteins selected from cell surface layer protein(s) found in other *C. glutamicum* strain(s), i.e. for example, deficient in PS1 and/or PS2 (CspB). Examples of the coryneform bacterium that is inherently deficient in a cell surface layer protein include *C. glutamicum* ATCC 13032, which is inherently deficient in the cspB gene.

Hereafter, means for reducing the activity of a protein will be explained.

The expression "activity of a protein is reduced" or "reduced activity" can mean that the activity of the target protein is decreased compared with that of a non-modified strain such as a wild-type strain or parent strain, which includes when the activity completely disappears. Specifically, the expression "activity of a protein is reduced" can mean that the number of molecules of the protein per cell is reduced, and/or the function of each molecule of the protein is reduced compared with those of a non-modified strain. That is, the term "activity" regarding the expression "activity of a protein is reduced" can mean the transcription amount (the amount of mRNA) of a gene encoding the protein or the amount of the protein, as well as the catalytic activity of the protein. In addition, the case where "number of molecules of the protein per cell is reduced" includes when the protein does not exist at all. Further, the case where "function of each molecule of the protein is reduced" includes when the function of each molecule of the protein completely disappears.

The modification for reducing the activity of a protein can be attained by, for example, reducing expression of a gene coding for the protein. "Reduction of gene expression" can also be referred to as "attenuation of gene expression". The reduction of gene expression may be induced by, for example, reduction of transcription efficiency, reduction of translation efficiency, or a combination of these. Reduction of expression of a gene can be attained by modifying an expression control sequence of the gene such as a promoter and the Shine-Dalgarno (SD) sequence. When an expression control sequence is modified, one nucleotide or more, two nucleotides or more, or three nucleotides or more, of the expression control sequence can be modified. Moreover, a part or all of the expression control sequence may be deleted. Reduction of gene expression can also be attained by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth.

The modification for reducing the activity of a protein can also be attained by, for example, disrupting the gene coding for the protein. Disruption of a gene can be attained by, for example, deleting a part or all of the coding region of the gene on a chromosome. Furthermore, the total gene including sequences upstream and downstream from the gene on a chromosome may be deleted. The region to be deleted may be any region such as an N-terminus region, an internal region, or a C-terminus region, so long as reduction of the activity of the protein is attained. Deletion of a longer region can usually more surely inactivate the gene. Further, it is preferred that the reading frames of the sequences upstream and downstream from the region to be deleted are not the same.

Disruption of a gene can also be attained by, for example, introduction of a mutation for an amino acid substitution (missense mutation), a stop codon (nonsense mutation), a frame shift mutation which adds or deletes one or two nucleotides into the coding region of the gene on a chromosome, or the like (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into the coding region of the gene on a chromosome. Site of the insertion may be any region of the gene, and insertion of a longer region can usually more surely inactivate the gene. It is preferred that the reading frames of the sequences upstream and downstream from the insertion site are not the same. The other sequence is not particularly limited so long as a sequence that reduces or eliminates the activity of the encoded protein is chosen, and examples include, for example, a marker gene such as an antibiotic resistance gene, a gene useful for production of a heterologous protein, and so forth.

Such modification of a gene on a chromosome as described above can be attained by, for example, preparing a deficient type gene in which a partial sequence of the gene is deleted so that it cannot produce a protein that can normally function, and transforming a bacterium with a recombinant DNA containing the deficient type gene to cause homologous recombination between the deficient type gene and the gene on a chromosome and thereby substituting the deficient type gene for the gene on the chromosome. In such a case, if a marker gene selected according to the characteristics of the host such as auxotrophy is included in the recombinant DNA, the operation becomes easy. The protein encoded by the deficient type gene has a conformation different from that of a wild-type protein, even if it is produced, and thus the function thereof can be reduced or eliminated. Such gene disruption based on gene substitution utilizing homologous recombination has been already established, and include methods called "Red driven integration" (Datsenko, K. A, and Wanner, B. L., Proc. Natl. Acad. Sci. USA, 97:6640-6645 (2000)), a method of using a linear DNA such as by utilizing the Red driven integration in combination with an excision system derived from λ phage (Cho, E. H., Gumport, R. I., Gardner, J. F., J. Bacteriol., 184:5200-5203 (2002)), a method of using a plasmid containing a temperature sensitive replication origin, a method of using a plasmid capable of conjugative transfer, a method of using a suicide vector not having replication origin which functions in a host (U.S. Pat. No. 6,303,383, Japanese Patent Laid-open (Kokai) No. 05-007491), and so forth.

The modification for reducing the activity of a protein can also be attained by, for example, a mutagenesis treatment. Examples of the mutagenesis treatment include usual mutagenesis treatments such as irradiation of X-ray or ultraviolet radiation and mutagenesis treatment with a mutation agent such as N-methyl-N'-nitro-N-nitrosoguanidine (MNNG), ethyl methanesulfonate (EMS), and methyl methanesulfonate (MMS).

Reduction of the activity of a target protein can be confirmed by measuring the activity of the protein. In the case of a penicillin-binding protein, whether the activity of the protein has been reduced can be confirmed by, for example, measuring the transpeptidase activity and/or the transglycosylase activity depending on the class to which the protein belongs. The transpeptidase activity and/or the transglycosylase activity can be measured by, for example, a method well known to those skilled in the art. Specifically, for example, the transpeptidase and transglycosylase activities of PBP1a can be measured by measuring the reaction of oligomerizing lipid II to glycan strands and forming peptide cross-links (Born P, et al., J Biol. Chem. 2006 Sep. 15; 281(37): 26985-93.). Specifically, the activity of a protein can be decreased by, for example, 50% or less, 20% or less, 10% or less, 5% or less, or even 0%, of that observed in a non-modified strain.

Reduction of expression of a target gene can be confirmed by confirming reduction of the transcription amount of the gene or reduction of the amount of the target protein expressed from the gene.

Reduction of the transcription amount of a target gene can be confirmed by comparing the amount of mRNA transcribed from the gene with that observed in a non-modified strain. Examples of the method for measuring the amount of mRNA include Northern hybridization, RT-PCR, and so forth (Molecular Cloning, Cold spring Harbor Laboratory Press, Cold Spring Harbor (USA), 2001). The amount of mRNA can be decreased by, for example, 50% or less, 20% or less, 10% or less, 5% or less, or 0%, of that observed in a non-modified strain.

Reduction of the amount of a target protein can be confirmed by Western blotting using antibodies that bind to the protein (Molecular Cloning, Cold Spring Harbor Laboratory Press, Cold Spring Harbor (USA) 2001). The amount of the protein can be decreased by, for example, 50% or less, 20% or less, 10% or less, 5% or less, or 0%, of that observed in a non-modified strain.

Disruption of a target gene can be confirmed by determining nucleotide sequence or restriction enzyme map of a part or all of the gene, full length of the gene, or the like depending on the means used for the disruption.

The methods mentioned above for reducing the activity of a protein can also be applied mutatis mutandis to arbitrary proteins and genes coding for them as well as for reducing the activity of a penicillin-binding protein and reducing the activity of a cell surface layer protein.

Hereafter, the "genetic construct for secretory expression of a heterologous protein" and a method for introducing it will be explained.

It is known that a secretory protein is generally translated as a preprotein (also referred to as prepeptide) or preproprotein (also referred to as prepropeptide), and then becomes a mature protein through processing. Specifically, a secretory protein is generally translated as a preprotein or preproprotein, then a signal peptide as the pre-part is cleaved with a protease (generally called signal peptidase), and the secretory protein is thereby converted into a mature protein or proprotein. As for the proprotein, the pro-part thereof is further cleaved by a protease, and the proprotein thereby becomes a mature protein. Hence, it is preferable to use a signal peptide for the secretory production of a heterologous protein. A preprotein and a preproprotein of a secretory protein may be collectively referred to as "secretory protein precursor". The "signal peptide" (also referred to as "signal sequence") can refer to an amino acid sequence present at the N-terminus of a secretory protein precursor, and usually not present in a natural mature protein.

Although the genetic construct is not particularly limited so long as secretory production of the heterologous protein is attained, it can contain a promoter sequence that functions in a coryneform bacterium, a nucleic acid sequence coding for a signal peptide that is ligated downstream from the promoter sequence and functions in the coryneform bacterium, and a nucleic acid sequence coding for the heterologous protein that is ligated downstream from the nucleic acid sequence coding for the signal peptide. The nucleic acid sequence coding for a signal peptide may be ligated downstream from the promoter sequence so that the signal peptide is expressed under the control of the promoter. The nucleic acid sequence coding for the heterologous protein may be ligated downstream from the nucleic acid sequence coding for the signal peptide so that the heterologous protein is expressed as a fusion protein with the signal peptide. The genetic construct can also contain a control sequence (operator, terminator, etc.) effective for expression of the heterologous protein gene in a coryneform bacterium at such an appropriate position that it can function.

The promoter is not particularly limited so long as a promoter that functions in a coryneform bacterium is chosen, and it may be a promoter derived from a coryneform bacterium, or a heterogenous promoter. The "promoter that functions in a coryneform bacterium" can refer to a promoter that has a promoter activity in a coryneform bacterium. Specific examples of the heterogenous promoter include, for example, promoters derived from E. coli such as tac promoter, lac promoter, trp promoter, and araBAD promoter. Among these, potent promoters such as tac promoter are preferred, and inducible promoters such as araBAD promoter are also preferred.

Examples of the promoter derived from a coryneform bacterium include, for example, promoters of the cell surface layer proteins PS1, PS2 (also referred to as CspB), and SlpA (also referred to as CspA), and promoters of various amino acid biosynthesis system genes. Specific examples of the promoters of various amino acid biosynthesis system genes include, for example, promoters of the glutamate dehydrogenase gene of the glutamic acid biosynthesis system, the glutamine synthetase gene of the glutamine synthesis system, the aspartokinase gene of the lysine biosynthesis system, the homoserine dehydrogenase gene of the threonine biosynthesis system, the acetohydroxy acid synthetase gene of the isoleucine and valine biosynthesis system, 2-isopropylmalate synthetase gene of the leucine biosynthesis system, the glutamate kinase gene of the proline and arginine biosynthesis system, the phosphoribosyl-ATP pyrophosphorylase gene of the histidine biosynthesis system, the deoxyarabinoheptulosonate phosphate (DAHP) synthetase gene of the aromatic amino acid biosynthesis systems such as those of tryptophan, tyrosine, and phenylalanine, the phosphoribosyl pyrophosphate (PRPP) amidotransferase gene of the nucleic acid biosynthesis systems such as those of inosinic acid and guanylic acid, the inosinic acid dehydrogenase gene, and the guanylic acid synthetase gene.

As the promoter, a high activity type of an existing promoter may be obtained by using various reporter genes and used. For example, by making the −35 and −10 regions in a promoter region closer to a consensus sequence, the activity of the promoter can be enhanced (International Patent Publication WO00/18935). Examples of method for evaluating strength of a promoter and strong promoters are described in the paper of Goldstein et al. (Prokaryotic promoters in biotechnology, Biotechnol. Annu. Rev., 1, 105-128 (1995)) and so forth. Additionally, it is known that substitution, insertion, or deletion of several nucleotides in a spacer region between the ribosome-binding site (RBS) and the translation initiation codon, especially a sequence immediately upstream from the initiation codon (5'-UTR), greatly affects stability of mRNA and translation efficiency of mRNA, and therefore, this sequence can be modified.

The signal peptide is not particularly limited so long as a signal peptide that functions in the coryneform bacterium is chosen, and it may be a signal peptide derived from the coryneform bacterium, or it may be a heterogenous signal peptide. The "signal peptide that functions in the coryneform bacterium" can refer to a peptide that, when it is ligated to the N-terminus of an objective protein, allows the coryneform bacterium to secrete the protein. The signal peptide can be a signal peptide of a secretory protein of the coryneform bacterium as the host, or a signal peptide of a cell surface layer protein of the coryneform bacterium. Examples of the cell surface layer protein of coryneform bacteria include PS1 and PS2 (CspB) derived from C. glutamicum (Japanese Patent Laid-open (Kohyo) No. 6-502548), and SlpA (CspA) derived from C. ammoniagenes (C. stationis) (Japanese Patent Laid-open (Kokai) No. 10-108675). The amino acid sequence of the signal peptide of PS1 is shown as SEQ ID NO: 83, the amino acid sequence of the signal peptide of PS2 (CspB) is shown as SEQ ID NO: 84, and the amino acid sequence of the signal peptide of SlpA (CspA) is shown as SEQ ID NO: 85. Moreover, U.S. Pat. No. 4,965,197 describes that there are signal peptides for DNases derived from coryneform bacteria, and such signal peptides can also be used for the present invention.

Although signal peptides have a certain characteristic of sequence common over biological species, a signal peptide that exhibits a secretory function in a certain biological species does not necessarily exhibit a secretory function in another biological species. Therefore, when a heterogenous signal peptide is used, a signal peptide that functions in the coryneform bacterium may be appropriately chosen. Whether a certain signal peptide functions in the coryneform bacterium can be confirmed by, for example, expressing the objective protein as a fusion protein with that signal peptide, and confirming whether the protein is secreted or not.

The signal peptide may include a part of N-terminus amino acid sequence of the secretory protein from which the signal peptide is derived. The signal sequence is generally cleaved by a signal peptidase, when the translation product is secreted out of the cell. In addition, as a gene coding for a signal peptide, although a naturally occurring gene may be used as it is, it may be modified so that it has the optimal codons according to codon frequencies in the chosen host.

Examples of the heterologous protein produced by secretory production by the method of the present invention include, for example, bioactive proteins, receptor proteins, antigenic proteins which can be used as vaccines, and enzymes. Examples of the enzymes include, for example, transglutaminases, proteases, endopeptidases, exopeptidases, aminopeptidases, carboxypeptidases, collagenases, chitinases, and so forth.

Examples of the bioactive proteins include, for example, growth factors, hormones, cytokines, antibody-related molecules.

Specific examples of the growth factor include, for example, Epidermal growth factor (EGF), Insulin-like growth factor (IGF), Transforming growth factor (TGF), Nerve growth factor (NGF), Brain-derived neurotrophic factor (BDNF), Vesicular endothelial growth factor (VEGF), Granulocyte-colony stimulating factor (G-CSF), Granulocyte-macrophage-colony stimulating factor (GM-CSF), Platelet-derived growth factor (PDGF), Erythropoietin (EPO), Thrombopoietin (TPO), acidic fibroblast growth factor (aFGF or FGF1), basic fibroblast growth factor (bFGF or FGF2), keratinocyto growth factor (KGF-1 or FGF7, and KGF-2 or FGF10), and Hepatocyte growth factor (HGF).

Specific examples of the hormone include, for example, insulin, glucagon, somatostatin, human growth hormone (hGH), parathyroid hormone (PTH), and calcitonin Specific examples of the cytokine include, for example, interleukins, interferons, tumor necrosis factors (TNFs).

Growth factors, hormones, and cytokines may not be strictly distinguished from each other. For example, a bioactive protein may be a protein such as a growth factor, hormone, and cytokine, or may be a protein that is classified as more than one of these.

A bioactive protein may be an intact protein, or may be a part of a protein. Examples of a part of a protein include, for example, a part having physiological activity. Specific examples of a part having physiological activity include, for example, Teriparatide, a bioactive peptide, which consists of 34 amino acid residues of N-terminus of parathyroid hormone (PTH).

The antibody-related molecule can refer to a protein that includes a single domain or a combination of two or more domains, such as domains that constitute a complete antibody. Examples of the domains that constitute a complete antibody include VH, CH1, CH2, and CH3, which are domains of a heavy chain, and VL and CL, which are domains of a light chain. The antibody-related molecule may be a monomer protein or a multimeric protein so long as it includes the above-mentioned molecular species. In the case where the antibody-related molecule is a multimeric protein, the antibody-related molecule may be a homo-multimer consisting of a single kind of subunit, or may be a hetero-multimer consisting of two or more kinds of subunits. Specific examples of the antibody-related molecule include, for example, complete antibodies, Fab, F(ab'), F(ab')$_2$, Fc, dimer consisting of the heavy chain (H chain) and the light chain (L chain), Fc-fusion proteins, the heavy chain (H chain), the light chain (L chain), single chain Fv (scFv), sc(Fv)$_2$, disulfide-linked Fv (sdFv), and diabody.

The receptor protein is not particularly limited, and can be, for example, a receptor protein for any of the bioactive proteins and other bioactive substances. Examples of other bioactive substances can include, for example, neurotransmitters such as dopamine. In addition, the receptor protein can also be an orphan receptor, of which ligand has not been identified.

The antigenic protein which can be used as a vaccine is not particularly limited so long as it is a protein which causes an immune response, and the antigenic protein can be appropriately chosen according to the intended target of the immune response.

Specific examples of the monomer protein include, for example, transglutaminases and the insulin-like growth factor 1 (IGF-1). Examples of transglutaminase gene include genes of secretory transglutaminases of actinomycetes such as *Streptoverticillium mobaraense* IFO 13819, *Streptoverticillium cinnamoneum* IFO 12852, *Streptoverticillium griseocarneum* IFO 12776, *Streptomyces lydicus* [WO9606931], filamentous fungi such as Oomycetes [WO96/22366], and so forth. In addition, specific examples of the monomer protein further include monomer proteins as the antibody-related molecules, for example, the heavy chain (H chain), the light chain (L chain), scFv, and sdFv.

Further, specific examples of the multimeric protein include, for example, the vascular endothelial growth factor (VEGF), insulin, interleukin-5, interferon-γ, tumor necrosis factors (TNFs). In addition, specific examples of the multimeric protein further include multimeric proteins as the antibody-related molecules, for example, complete antibodies, Fab, F(ab'), F(ab')$_2$, Fc, dimer consisting of the heavy chain (H chain) and the light chain (L chain), Fc-fusion proteins, sc(Fv)$_2$, and diabody. Among these, Fab, F(ab')$_2$, and Fc-fusion proteins are preferred.

Fab (fragment, antigen binding) is a part of a complete antibody except for the Fc region of the H chain, and it is an antibody fragment consisting only of an antigen-binding region. Fab is a dimer consisting of one molecule of the Fab moiety of the H chain and one molecule of L chain, and they aggregate by a disulfide bond at the C-terminus. The complete antibody is an H2L2 tetramer, and has a huge molecular weight of about 150 kDa, whereas Fab has a small molecular weight of about 50 kDa, and therefore Fab is thought to show superior permeability for an objective tissue. Since Fab does not have the Fc region, it has neither the complement activity nor crystallization ability, but since it has antigen-binding ability, it is mainly used for the purpose of neutralizing an antigen. Among the antibody drugs, Fab especially attracts attention in recent years.

F(ab') is a part of a complete antibody except for the Fc' region of the H chain. F(ab') is a dimer consisting of one molecule of the F(ab') moiety of the H chain and one molecule of the L chain, and they aggregate by a disulfide bond at the C-terminus The reminder moiety of the H chain in F(ab') is longer than the reminder moiety of the H chain in Fab, and hence, in F(ab'), the disulfide bond moiety linking the H chains remains. Therefore, two molecules of F(ab') can form F(ab')$_2$ by a disulfide bond. F(ab') and F(ab')$_2$ can also be used as antibody drugs like a Fab fragment.

Fc (fragment, crystallizable) is an antibody fragment consisting only of the Fc region that participates in the complement activity and crystallization ability. A protein consisting of the Fc region of the H chain and another functional protein fused to each other is called an Fc-fusion protein.

Genes coding for these proteins can be modified according to the chosen host and to obtain a desired activity. For example, the genes coding for these proteins may be modified so that the proteins include addition, deletion, substitution, or the like of one or several amino acid residues. The explanations concerning variants of the penicillin-binding proteins and the genes coding for them mentioned above can also be applied mutatis mutandis to the heterologous protein to be produced by secretory production by the method of the present invention and the gene coding for it. Further, in the genes coding for these proteins, any codon may be replaced with an equivalent codon thereof. For example, in the genes coding for these proteins, codons may be optimized as required according to codon frequencies observed in the host.

The N-terminus region of the heterologous protein obtained by the method of the present invention may be the same as that of the natural protein, or may not be the same as that of the natural protein. For example, the N-terminus region of the eventually obtained heterologous protein may be that of the natural protein including addition or deletion of one or several amino acid residues. Although the number of the "one or several" amino acid residues may differ depending on the full length or structure of the objective heterologous protein, specifically, it can be 1 to 20, 1 to 10, or 1 to 5.

Further, the heterologous protein to be produced by secretory production may be a protein containing a pro-structure part (proprotein). In the case where the heterologous protein to be produced by secretory production is a proprotein, the heterologous protein to be eventually obtained may be the proprotein or may not be the proprotein. That is, the proprotein may be processed into the mature protein by cleavage of the pro-structure part. The cleavage can be attained with, for example, a protease. When a protease is used, in view of the activity of the protein to be eventually obtained, the proprotein is generally cleaved preferably at a position substantially the same as that of the natural protein, or more preferably at a position exactly the same as that of the natural protein to obtain the same mature protein as the natural mature protein. Therefore, a specific protease that cleaves the proprotein at such a position that the same protein as the naturally occurring mature protein is generated is most preferred. However, the N-terminus region of the heterologous protein to be eventually obtained may not be the same as that of the natural protein as described above. For example, depending on type, purpose of use, etc. of the heterologous protein to be produced, a protein having an N-terminus longer or shorter by one to several amino acid residues compared with the natural protein may have more appropriate activity. Proteases that can be used include, for example, commercially available proteases such as Dispase (produced by Boehringer Mannheim) as well as those obtainable from culture broth of a microorganism such as culture broth of actinomycetes. Such proteases can be used in an un-purified state, or may also be used after purification to an appropriate purity as required.

The method for introducing the genetic construct into the coryneform bacterium is not particularly limited. In the bacterium of the present invention, the genetic construct can be present on a vector that autonomously replicates out of the chromosome such as a plasmid, or may be incorporated into the chromosome. In addition, as described above, for constructing the bacterium of the present invention, modifications such as the introduction of the genetic construct, impartation or enhancement of the ability to produce a protein by secretory production, reduction of activity of a penicillin-binding protein, and reduction of activity of a cell surface layer protein can be performed in an arbitrary order.

The genetic construct can be introduced into a host by using, for example, a vector including the genetic construct. The vector is not particularly limited so long as a vector autonomously replicable in the coryneform bacterium is chosen, and may be, for example, a vector derived from a bacterial plasmid, a vector derived from a yeast plasmid, a vector derived from a bacteriophage, cosmid, phagemid, or the like. As the vector, for example, a plasmid derived from a coryneform bacterium is preferred. Specific examples of vector autonomously replicable in coryneform bacteria include pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVC7 described in Japanese Patent Laid-open (Kokai) No. 9-070291; and so forth.

Further, an artificial transposon and so forth can also be used. When a transposon is used, a heterologous protein gene is introduced into a chromosome by homologous recombination or translocation ability of the transposon itself. Other examples of the introduction method utilizing homologous recombination include, for example, the methods utilizing a linear DNA, a plasmid having a temperature sensitive replication origin, a plasmid capable of conjugative transfer, a suicide vector not having a replication origin which functions in a host, and so forth. In addition, when a heterologous protein gene is introduced into a chromosome, so long as the genetic construct is present on the chromosome, either one or both of a promoter sequence and a nucleic acid sequence coding for the signal peptide contained in the genetic construct may be native to the host chromosome. Specifically, for example, by using a promoter sequence and a nucleic acid sequence coding for the signal peptide ligated downstream from the promoter sequence native to the host chromosome as they are, and replacing only the gene ligated downstream from the nucleic acid sequence coding for the signal peptide with the objective heterologous protein gene, the genetic construct can be present on the chromosome, and the bacterium of the present invention can be thereby constructed.

Also, in the case where two or more kinds of proteins are expressed, genetic constructs for secretory expression of the proteins may be harbored by the bacterium of the present invention so that secretory expression of the target heterologous protein(s) can be attained. Specifically, for example, all of the genetic constructs for secretory expression of the proteins may be harbored on a single vector, or may be harbored on a chromosome. Further, the genetic constructs for secretory expression of the proteins may be harbored separately on a plurality of vectors, or may be harbored separately on a single or a plurality of vectors and a chromosome. The "case where two or more kinds of proteins are expressed" can include, for example, the case where two or more kinds of heterologous proteins are produced by secretory production, or the case where a hetero-multimeric protein is produced by secretory production.

The method for introducing the genetic construct into the coryneform bacterium is not particularly limited, and a generally used method, for example, the protoplast method (Gene, 39, 281-286 (1985)), the electroporation method (Bio/Technology, 7, 1067-1070 (1989)), and so forth can be used.

<2> Method for Producing a Heterologous Protein of the Present Invention

The present invention provides a method for producing a heterologous protein by culturing the bacterium of the present invention and collecting the heterologous protein produced by secretory production (henceforth also referred to as the "method of the present invention" or the "method for producing a heterologous protein of the present invention").

The bacterium of the present invention can be cultured according to usually used method and conditions. For example, the bacterium of the present invention can be cultured in a usual medium containing a carbon source, a nitrogen source, and inorganic ions. In order to obtain still higher proliferation, organic micronutrients such as vitamins and amino acids can also be added as required.

As the carbon source, carbohydrates such as glucose and sucrose, organic acids such as acetic acid, alcohols, and others can be used. As the nitrogen source, ammonia gas, aqueous ammonia, ammonium salts, and others can be used. As the inorganic ions, calcium ions, magnesium ions, phosphate ions, potassium ions, iron ions, and so forth are appropriately used as required. The culture is performed within appropriate ranges of pH 5.0 to 8.5 and 15 to 37° C. for 1 to 7 days under aerobic conditions. Further, the culture conditions for L-amino acid production by coryneform bacteria and other conditions described in the methods for producing a protein using a signal peptide of the Sec type or the Tat type can be used (refer to WO01/23591 and WO2005/103278). Further, when an inducible promoter is used for expression of the heterologous protein, culture may also be performed with adding a promoter-inducing agent to the medium. By culturing the bacterium of the present invention under such conditions, a large amount of the objective protein can be produced in cells and efficiently secreted out of the cells. In addition, the produced heterologous protein can be secreted out of the cells, and therefore a protein that may be lethal if it is accumulated in a large amount in cells of microorganisms, such as transglutaminases, can also be continuously produced without lethal effect.

The protein secreted in the medium according to the method of the present invention can be separated and purified from the medium after the culture by a method well known to those skilled in the art. For example, after the cells are removed by centrifugation or the like, the protein can be separated and purified by a known appropriate method such as salting out, ethanol precipitation, ultrafiltration, gel filtration chromatography, ion exchange column chromatography, affinity chromatography, medium or high pressure liquid chromatography, reverse phase chromatography, and hydrophobic chromatography, or a combination of these. Further, in a certain case, culture or culture supernatant may be used as it is. The protein secreted in the cell surface layer according to the method of the present invention can also be separated and purified in the same manner as that for the case where the protein is secreted in the medium, after solubilizing it by a method well known to those skilled in the art such as elevation of salt concentration and use of a surfactant. Further, in a certain case, the protein secreted in the cell surface layer may be used as, for example, an immobilized enzyme, without solubilizing it.

Secretory production of the objective heterologous protein can be confirmed by performing SDS-PAGE for the culture supernatant and/or a fraction containing the cell surface layer as a sample thereby confirming the molecular weight of the separated protein bands. In addition, secretory production of the objective heterologous protein can be confirmed by performing Western blotting using antibodies for the culture supernatant and/or a fraction containing the cell surface layer as a sample (Molecular Cloning, Cold spring Harbor Laboratory Press, Cold Spring Harbor (USA), 2001). Further, secretory production of the objective heterologous protein can be confirmed by determination of N-terminus amino acid sequence using protein sequencer. Furthermore, secretory production of the objective heterologous protein can be confirmed by measuring its mass using mass spectrometer. Also, when the objective heterologous protein is an enzyme or a protein having some kind of bioactivity that can be measured, secretory production of the objective heterologous protein can be confirmed by measuring enzyme activity or bioactivity of the protein in the culture supernatant and/or a fraction containing the cell surface layer as a sample.

EXAMPLES

The present invention will be further specifically explained with reference to the following non-limiting examples.

Example 1

Construction of a *Corynebacterium glutamicum* that is Deficient in Each of Penicillin-Binding Proteins PBP1a and PBP1b (1) Construction of vector pBSΔCgl0278 for deleting Cgl0278 gene coding for PBP1a The genome sequence of *C. glutamicum* ATCC 13032 and the nucleotide sequence of the Cgl0278 gene coding for the penicillin-binding protein PBP1a have already been determined (Genbank Accession No. BA000036, NCBI gene entry NCgl0274). With reference to this sequence, the primers shown as SEQ ID NOS: 1, 2, 3, and 4 were synthesized. By PCR using the chromosomal DNA of the *C. glutamicum* ATCC 13869 strain prepared in a conventional manner (method of Saito and Miura [Biochim Biophys. Acta, 72, 619 (1963)]) as a template, and the primers of SEQ ID NOS: 1 and 2, and SEQ ID NOS: 3 and 4, about 1 kbp of the 5' side upstream region and about 1 kbp of 3' side downstream region of Cgl0278 coding for PBP1a were amplified, respectively. Then, by PCR using both the amplified DNA fragments as a template and DNAs shown as SEQ ID NOS: 1 and 4 as primers, a DNA fragment of about 2 kbp having both the fragments fused to each other was obtained. In the primers of SEQ ID NOS: 1 and 4, recognition sequences for the restriction enzymes BamH I and Xba I were designed, respectively. For PCR, Pyrobest DNA Polymerase (produced by Takara Bio) was used, and the reaction conditions were those of the protocol recommended by the manufacturer. This DNA fragment was treated with the restriction enzymes BamH I and Xba I, and inserted into the BamH I-Xba I site of pBS4 described in WO2005/113744 to obtain a vector pBSΔ-Cgl0278 for deleting the Cgl0278 gene. For the ligation reaction, DNA Ligation Kit Ver. 2.1 (produced by Takara Bio) was used, and the reaction conditions were those of the protocol recommended by the manufacturer.

(2) Construction of Vector pBSΔCgl2986 for Deleting Cgl2986 Gene Coding for PBP1b The genome sequence of *C. glutamicum* ATCC 13032 and the nucleotide sequence of the Cgl2986 gene coding for the penicillin-binding protein PBP1b have already been determined (Genbank Accession No. BA000036, NCBI gene entry NCgl2884). In the same manner as that for Cgl0278, with reference to this sequence, the primers shown as SEQ ID NOS: 5, 6, 7, and 8 were synthesized. By PCR using the prepared chromosomal DNA of the *C. glutamicum* ATCC 13869 strain as a template, and the primers of SEQ ID NOS: 5 and 6, and SEQ ID NOS: 7 and 8, about 1.3 kbp of 5' side upstream region and about 1.1 kbp of 3' side downstream region of Cgl2986 coding for PBP1b were amplified, respectively. Then, by PCR using both the amplified DNA fragments as a template and DNAs shown as SEQ ID NOS: 05 and 08 as primers, a DNA fragment of about 2.4 kbp consisting of both the fragments fused to each other was obtained. The obtained DNA fragment of about 2.4 kbp contained one recognition sequence for the restriction enzyme Pst I and one recognition sequence for the restriction enzyme Sal I. For PCR, Pyrobest DNA Polymerase (produced by Takara Bio) was used, and the reaction conditions were those of the protocol recommended by the manufacturer. A fragment of about 2.2 kbp obtained by treating the above DNA fragment with the restriction enzymes Pst I and Sal I was inserted into the Pst I-Sal I site of pBS5T described in WO2006/057450 to obtain a vector pBSΔCgl2986 for deleting the Cgl2986 gene.

(3) Construction of PBP1a-Deficient Strain and PBP1b-Deficient Strain

Then, the *C. glutamicum* YDK010 strain described in WO2004/029254 was transformed with each of the constructed pBSΔCgl0278 and pBSΔCgl2986. The *C. glutamicum* YDK010 strain is a cell surface layer protein PS2 deficient strain of the *C. glutamicum* AJ12036 strain (FERM BP-734) (WO2004/029254). Strains were selected from the obtained transformants according to the methods described in WO2005/113744 and WO2006/057450 to obtain YDK010ΔPBP1a strain deficient in the Cgl0278 gene and YDK010ΔPBP1b strain deficient in the Cgl2986 gene.

Example 2

Secretory Expression of H Chain Region of Fab Fragment of Antibody Trastuzumab Using *Corynebacterium glutamicum* Strains Made Deficient in Penicillin-Binding Proteins PBP1a and PBP1b, Respectively Construction of Plasmid for Secretory Expression of H Chain Region of Fab Fragment of Antibody Trastuzumab The gene sequence of the variable region of the H chain in the breast cancer cell specific antibody, trastuzumab, has already been determined (Genbank Accession No. AY513484). With reference to this sequence and a sequence of the non-variable region of the H chain of a common antibody, DNAs shown as SEQ ID NOS: 9 to 42 were synthesized in consideration of the codon frequencies in *C. glutamicum*. The full length H chain region of trastuzumab was amplified by PCR using the above DNAs as a template and separately synthesized DNAs shown as SEQ ID NOS: 43 and 44 as primers thereby to obtain a DNA fragment of about 1.4 kbp shown as SEQ ID NO: 45. The amino acid sequence of the H chain of the antibody trastuzumab encoded by the DNA of SEQ ID NO: 45 was shown in SEQ ID NO: 86.

Then, by using pPKSPTG1 described in WO01/23591 (pPKSPTG1 is a vector for secretory expression of protransglutaminase (transglutaminase containing a pro-structure part), and contains a promoter derived from the PS2 gene of the *C. glutamicum* ATCC 13869 strain, a DNA coding for the signal peptide derived from SlpA of the *C. ammoniagenes* (*C. stationis*) ATCC 6872 strain expressibly ligated downstream from the promoter, and the protransglutaminase gene derived from *Streptoverticillium mobaraense* ligated so that the protein is expressed as a fusion protein with the above signal peptide) as a template and the primers shown as SEQ ID NOS: 46 and 47, a region including the aforementioned promoter region and the aforementioned signal peptide region was amplified by PCR thereby to obtain a DNA fragment of about 0.7 kbp.

Then, by PCR using both the amplified DNA fragments (the fragment including the full length H chain region of trastuzumab and the fragment including the promoter region and the signal peptide region) as a template and DNAs shown as SEQ ID NOS: 44 and 46 as primers, a DNA fragment of about 2.0 kbp having both the DNA fragments fused to each other was obtained.

Then, by PCR using this fusion DNA fragment as a template and DNAs shown as SEQ ID NOS: 46 and 48, SEQ ID NOS: 46 and 49, SEQ ID NOS 46 and 50, SEQ ID NOS: 46 and 51, SEQ ID NOS: 46 and 52, SEQ ID NOS: 46 and 53, and SEQ ID NOS: 46 and 54 as primers, DNA fragments of about 1.4 kbp each was obtained, respectively. In the primer of SEQ ID NO: 46, a recognition sequence for the restriction enzyme Kpn I was designed. In each of the primers of SEQ ID NOS: 48, 49, 50, 51, 52, 53 and 54, the stop codon and a recognition sequence for the restriction enzyme Kpn I were designed. For PCR, Pyrobest DNA Polymerase (produced by Takara Bio) was used, and the reaction conditions were those of the protocol recommended by the manufacturer. These DNA fragments were treated with the restriction enzyme Kpn I, and each inserted into the Kpn I site of pPK4 described in Japanese Patent Laid-open (Kokai) No. 9-322774 to obtain plasmids enabling secretory expression of the H chain region of the Fab moiety of trastuzumab, pPKStrast-FabH(1-223C), pPKStrast-FabH(1-228T), pPKStrast-FabH(1-229C), pPK-Strast-FabH(1-230P), pPKStrast-FabH(1-231P), pPKStrast-FabH(1-232C), and pPKStrast-FabH(1-233P). Specifically, with these plasmids, an amino acid sequence of the H chain of trastuzumab from the first amino acid residue to 223rd, 228th, 229th, 230th, 231st, 232nd or 233rd amino acid residue can be expressed (numbers of expressible amino acid residues are included in the plasmid names). By determining the nucleotide sequences of the inserted fragments, it was confirmed that expected genes were constructed. The nucleotide sequences were determined by using BigDye® Terminator v3.1 Cycle Sequencing Kit (produced by Applied Biosystems), and 3130 Genetic Analyzer (produced by Applied Biosystems).

Figure 2:
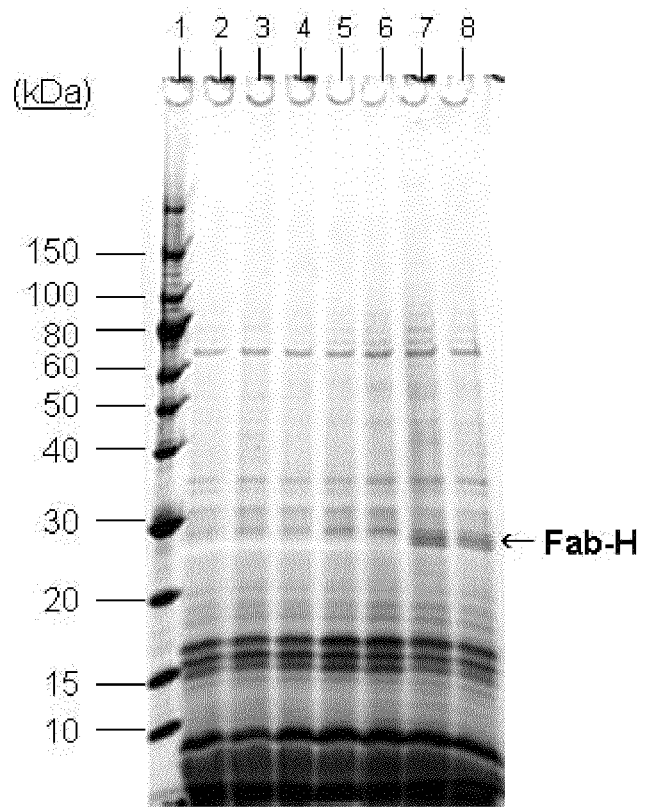
FIG. 2 is a photograph showing the results of reduced SDS-PAGE of the H chain region of the Fab fragment of trastuzumab expressed in the YDK010 strain (parent strain), the YDK010ΔPBP1a strain, and the YDK010ΔPBP1b strain.

(2) Secretory Expression of H Chain Region of Fab Fragment of Antibody Trastuzumab Using Penicillin-Binding Protein PBP1a-Deficient Strain and PBP1b-Deficient Strain By using the plasmid for secretory expression of the H chain region of the Fab fragment of the antibody trastuzumab constructed in Example 2 (1), pPKStrast-FabH(1-229C), each of the YDK010 strain, the YDK010ΔPBP1a strain, and the YDK010ΔPBP1b strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 μg of thiamine hydrochloride, 450 μg of biotin, 0.15 g of DL-methionine, and 50 g of calcium carbonate in a volume of 1 L with water, adjusted to pH 7.0) containing 25 mg/l of kanamycin at 30° C. for 72 hours. After completion of the culture, culture supernatant obtained by centrifuging each culture broth was subjected to reduced SDS-PAGE, and then stained with SYPRO Orange (produced by Invitrogen). As a result, the band of the objective protein was not detected for the parent strain YDK010 and the YDK010ΔPBP1b strain, whereas a band of a protein of the same molecular weight as that of the objective H chain of the Fab fragment of the antibody trastuzumab was detected only for the YDK010ΔPBP1a strain (FIGS. 1 and 2). When the N-terminus sequence of the protein of this band was determined by using a protein sequencer PPSQ-21A (produced by Shimadzu), the sequence agreed with the N-terminus sequence of the objective H chain of the Fab fragment of the antibody trastuzumab, and therefore secretory expression of the H chain of the Fab fragment of the antibody trastuzumab in the culture supernatant was confirmed.

Figure 3:
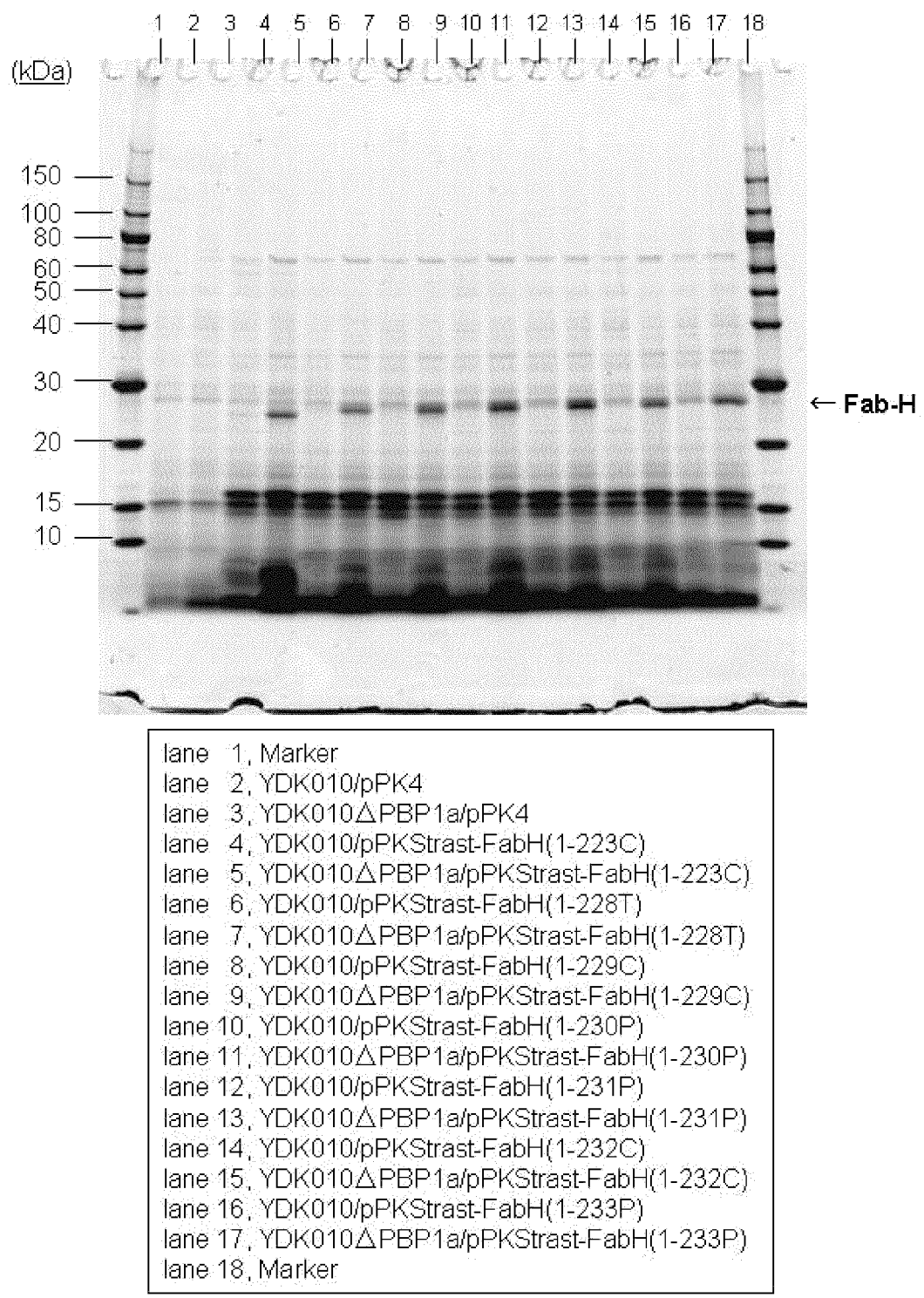
FIG. 3 is a photograph showing the results of reduced SDS-PAGE of the H chain region of the Fab fragment of trastuzumab expressed in the YDK010 strain (parent strain) and the YDK010ΔPBP1a strain.

Then, by using each of the plasmids for secretory expression of the H chain region of the Fab fragment of the antibody trastuzumab constructed in Example 2 (1), pPKStrast-FabH(1-223C), pPKStrast-FabH(1-228T), pPKStrast-FabH(1-229C), pPKStrast-FabH(1-230P), pPKStrast-FabH(1-231P), pPKStrast-FabH(1-232C), and pPKStrast-FabH(1-233P), each of the YDK010 strain and the YDK010ΔPBP1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 μg of thiamine hydrochloride, 450 μg of biotin, 0.15 g of DL-methionine, and 50 g of calcium carbonate in a volume of 1 L with water, adjusted to pH 7.0) containing 25 mg/l of kanamycin at 30° C. for 72 hours. After completion of the culture, culture supernatant obtained by centrifuging each culture broth was subjected to reduced SDS-PAGE, and then stained with SYPRO Orange (produced by Invitrogen). As a result, even when any of the secretory expression plasmids was used, the band of the objective protein was not detected for the parent strain YDK010, whereas a band of a protein of the same molecular weight as that of the H chain of the Fab fragment of the objective antibody trastuzumab was detected only for the YDK010ΔPBP1a strain (FIG. 3).

Example 3

Secretory Expression of L Chain Region of Fab Fragment of Antibody Trastuzumab Using *Corynebacterium glutamicum* Made Deficient in Penicillin-Binding Protein PBP1a Construction of Plasmid for Secretory Expression of L Chain Region of Fab Fragment of Antibody Trastuzumab The gene sequence of the variable region of the L chain in the breast cancer cell specific antibody, trastuzumab, has already been determined (Genbank Accession No. AY513485). With reference to this sequence and a sequence of the non-variable region of the L chain of a common antibody, DNAs shown as SEQ ID NOS: 55 to 70 were synthesized in consideration of the codon frequencies in *C. glutamicum*. The full length L chain region of trastuzumab was amplified by PCR using the above DNAs as a template and separately synthesized DNAs shown as SEQ ID NOS: 71 and 72 as primers thereby to obtain a DNA fragment shown as SEQ ID NO: 73 of about 0.6 kbp. The amino acid sequence of the L chain of the antibody trastuzumab encoded by the DNA of SEQ ID NO: 73 was shown in SEQ ID NO: 87. Then, by using pPKSPTG1 described in WO01/23591 (containing a promoter derived from the *C. glutamicum* ATCC 13869 strain and a signal peptide region derived from the *C. ammoniagenes* (*C. stationis*) ATCC 6872 strain) as a template and the primers shown as SEQ ID NOS: 74 and 75, a region including the aforementioned promoter region and the aforementioned signal peptide region was amplified by PCR thereby to obtain a DNA fragment of about 0.7 kbp. Then, by PCR using both the amplified DNA fragments (the fragment including the L chain region of trastuzumab and the fragment including the promoter region and the signal peptide region) as a template and DNAs shown as SEQ ID NOS: 74 and 76 as primers, a DNA fragment of about 1.3 kbp consisting of both the DNA fragments fused to each other was obtained. In the primers of SEQ ID NOS: 74 and 76, a recognition sequence for the restriction enzyme BamH I was designed. For PCR, Pyrobest DNA Polymerase (produced by Takara Bio) was used, and the reaction conditions were those of the protocol recommended by the manufacturer. This fusion DNA fragment was treated with the restriction enzyme BamH I, and inserted into the BamH I site of pPK4 described in Japanese Patent Laid-open (Kokai) No. 9-322774 to obtain a plasmid enabling secretory expression of the L chain region of the Fab moiety of trastuzumab, pPKStrast-FabL. By determining the nucleotide sequence of the inserted fragment, it was confirmed that expected gene was constructed. The nucleotide sequence was determined by using BigDye® Terminator v3.1 Cycle Sequencing Kit (produced by Applied Biosystems), and 3130 Genetic Analyzer (produced by Applied Biosystems).

Figure 4:
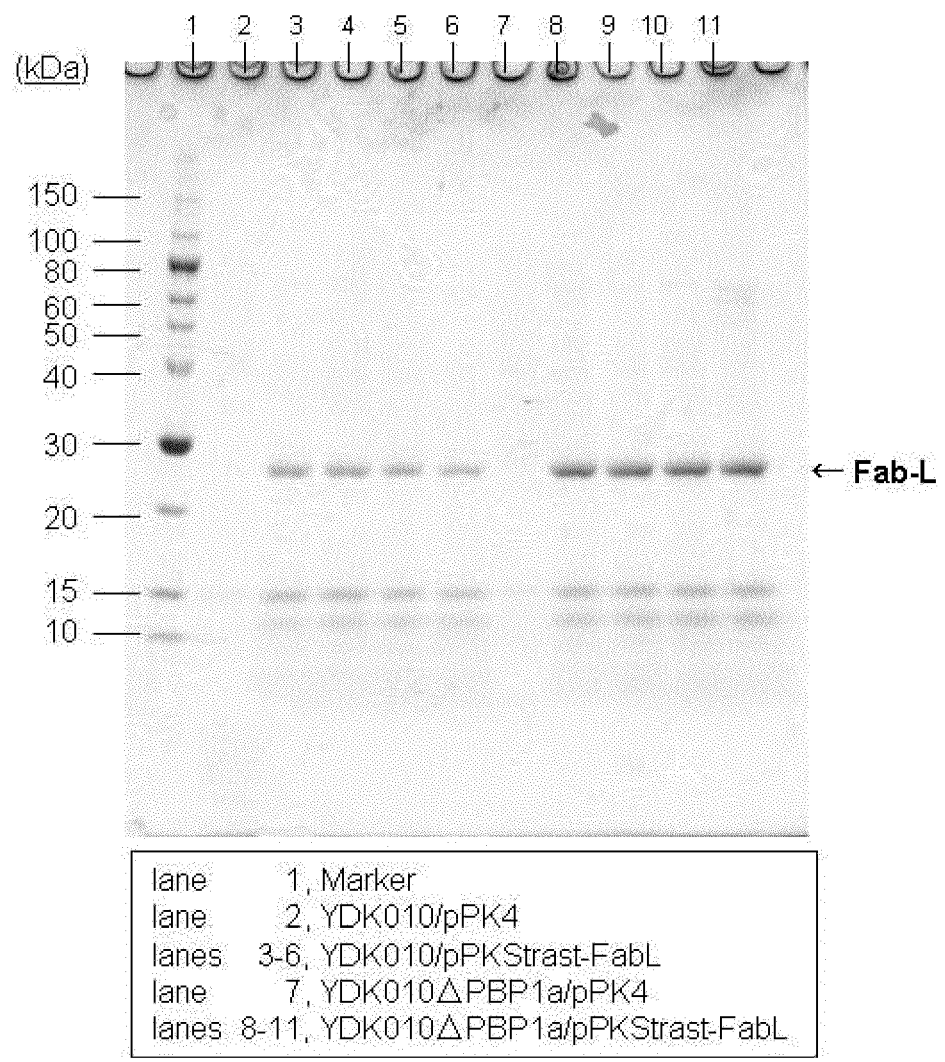
FIG. 4 is a photograph showing the results of reduced SDS-PAGE of the L chain region of the Fab fragment of trastuzumab expressed in the YDK010 strain (parent strain) and the YDK010ΔPBP1a strain.

(2) Secretory Expression of L Chain Region of Fab Fragment of Antibody Trastuzumab Using Penicillin-Binding Protein PBP1a-Deficient Strain By using the plasmid for secretory expression of the L chain region of the Fab fragment of the antibody trastuzumab constructed in Example 3 (1), pPKStrast-FabL, each of the YDK010 strain and the YDK010ΔPBP1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 μg of thiamine hydrochloride, 450 μg of biotin, 0.15 g of DL-methionine, and 50 g of calcium carbonate in a volume of 1 L with water, adjusted to pH 7.0) containing 25 mg/l of kanamycin at 30° C. for 72 hours. After completion of the culture, culture supernatant obtained by centrifuging each culture broth was subjected to reduced SDS-PAGE, and then stained with CBB R250 (produced by Bio-Rad). As a result, a band of a protein of the same molecular weight as that of the L chain of the Fab fragment of the objective antibody trastuzumab was detected for the YDK010ΔPBP1a strain with a band strength higher than at least twice the strength observed for the parent strain YDK010 (FIG. 4). When the N-terminus sequence of the protein of this band was determined by using a protein sequencer PPSQ-21A (produced by Shimadzu), the sequence agreed with the N-terminus sequence of the L chain of the Fab fragment of the objective antibody trastuzumab, and therefore secretory expression of the L chain of the Fab fragment of the antibody trastuzumab in the culture supernatant could be confirmed.

Example 4

Secretory Expression of Fab(H&L) Fragment of Antibody Trastuzumab Using *Corynebacterium glutamicum* Strain Made Deficient in Penicillin-Binding Proteins PBP1a (1) Construction of Plasmid for Secretory Expression of Fab(H&L) Fragment of Antibody Trastuzumab By inserting DNA fragments of about 1.4 kbs each, which were obtained by digesting the expression plasmids for the H chain region of the Fab fragment of the antibody trastuzumab constructed in Example 2 (1) with the restriction enzyme Kpn I, into the Kpn I site of pPKStrast-FabL, which was an expression plasmid for the L chain region of the Fab fragment of the antibody trastuzumab constructed in Example 3 (1), plasmids for coexpression of the H chain region and the L chain region of the Fab fragment of trastuzumab, pPKStrast-FabH(1-223C)+L, pPKStrast-FabH(1-228T)+L, pPKStrast-FabH(1-229C)+L, pPKStrast-FabH(1-230P)+L, pPKStrast-FabH(1-231P)+L, pPKStrast-FabH(1-232C)+L, and pPKStrast-FabH(1-233P)+L were obtained.

Figure 5:
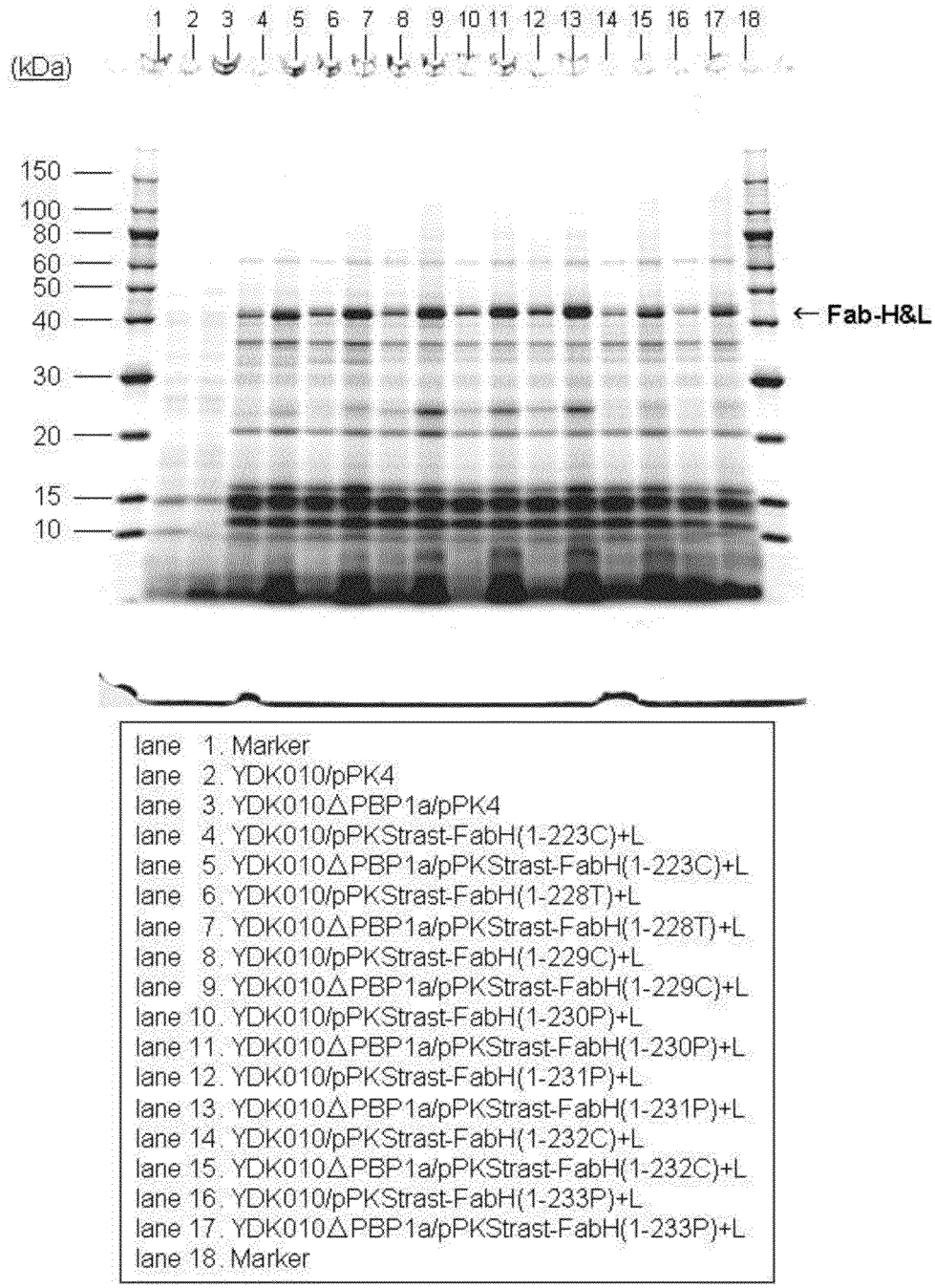
FIG. 5 is a photograph showing the results of non-reduced SDS-PAGE of the H chain region and the L chain region of the Fab fragment of trastuzumab coexpressed in the YDK010 strain (parent strain) and the YDK010ΔPBP1a strain.

(2) Secretory Expression of Fab(H&L) Fragment of Antibody Trastuzumab Using Penicillin-Binding Protein PBP1a Deficient Strain By using the plasmids for secretory expression of the Fab (H&L) fragment of the antibody trastuzumab constructed in Example 4 (1), pPKStrast-FabH(1-223C)+L, pPKStrast-FabH(1-228T)+L, pPKStrast-FabH(1-229C)+L, pPKStrast-FabH(1-230P)+L, pPKStrast-FabH(1-231P)+L, pPKStrast-FabH(1-232C)+L, and pPKStrast-FabH(1-233P)+L, each of the YDK010 strain and the YDK010ΔPBP1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 μg of thiamine hydrochloride, 450 μg of biotin, 0.15 g of DL-methionine, and 50 g of calcium carbonate in a volume of 1 L with water, adjusted to pH 7.0) containing 25 mg/l of kanamycin at 30° C. for 96 hours. After completion of the culture, culture supernatant obtained by centrifuging each culture broth was subjected to non-reduced SDS-PAGE, and then stained with SYPRO Orange (produced by Invitrogen), and secretion amounts of the Fab(H&L) fragments of the antibody trastuzumab were compared. As a result, even when any of the secretory expression plasmids was used, the secretion amount of the Fab(H&L) fragment of the antibody trastuzumab was significantly improved in the YDK010ΔPBP1a strain compared with that observed for the parent strain YDK010 (FIG. 5). When the N-terminus sequence of the Fab(H&L) protein in the band detected for the transformant obtained from the YDK010ΔPBP1a strain using pPKStrast-FabH(1-229C)+L was determined with a protein sequencer PPSQ-21A (produced by Shimadzu), both sequences of the N-terminus sequence of the H chain and the N-terminus sequences of the L chain of the Fab fragment of the objective antibody trastuzumab were included, and therefore it could be confirmed that the Fab(H&L) fragments of the antibody trastuzumab were expressed and secreted to form aggregates in the culture supernatant.

Figure 6:
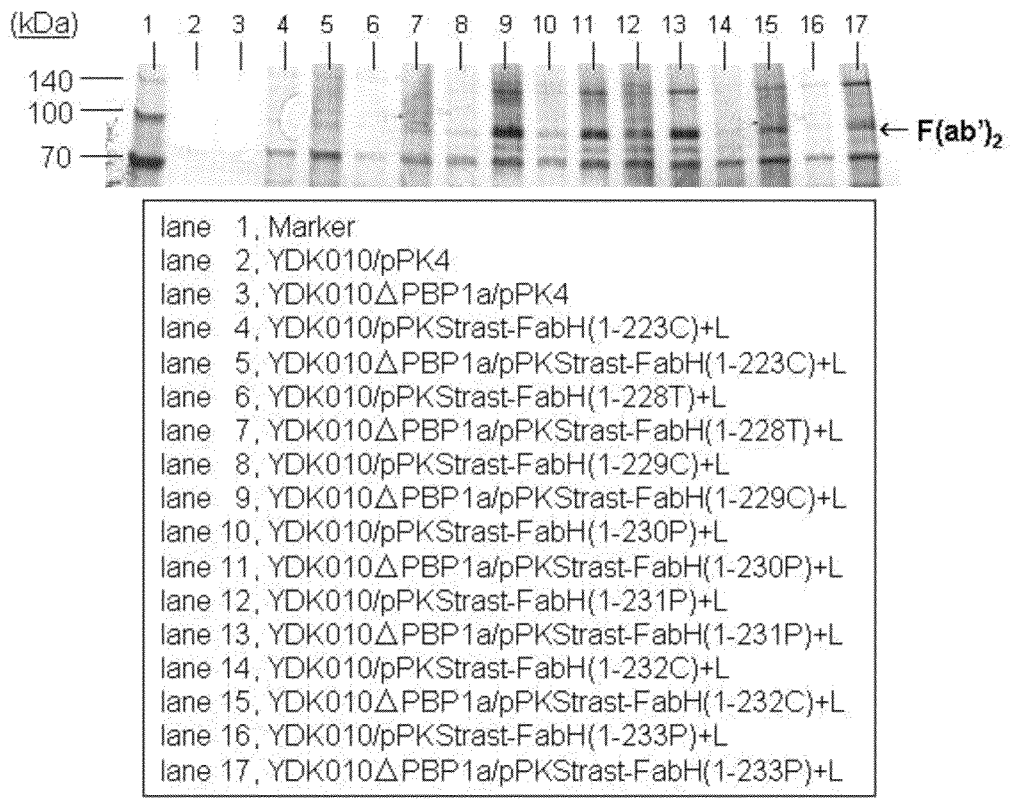
FIG. 6 is a photograph showing the results of Western blotting of the F(ab')$_2$ fragment of trastuzumab expressed in the YDK010 strain (parent strain) and the YDK010ΔPBP1a strain.

(3) Secretory Expression of F(Ab')$_2$ Fragment of Antibody Trastuzumab Using Penicillin-Binding Protein PBP 1a Deficient Strain Each of the culture supernatants obtained in Example 4 (2) was subjected to non-reduced SDS-PAGE, and then proteins were transferred onto a PVDF membrane by using iBlot® Gel Transfer Stacks PVDF, Mini (produced by Invitrogen) and iBlot™ Gel Transfer System (produced by Invitrogen). Western blotting was performed for this PVDF membrane by using an alkaline phosphatase-labeled anti-human IgG [H&L] antibody (produced by ROCKLAND) and Alkaline Phosphatase Conjugate Substrate Kit (produced by Bio-Rad) thereby to detect F(ab')$_2$ of the antibody trastuzumab. As a result, the band of a protein of the same molecular weight as that of F(ab')$_2$ fragment of the antibody trastuzumab was detected for the culture supernatant of the transformant harboring each of pPKStrast-FabH(1-229C)+L, pPKStrast-FabH(1-230P)+L, pPKStrast-FabH(1-231P)+L, pPKStrast-FabH(1-232C)+L, and pPKStrast-FabH(1-233P)+L, which are plasmids for coexpression of the H chain region comprising Cys residue which forms disulfide bond linking the H chains, and the L chain region. Further, even when any of these secretory expression plasmids was used, the intensity of the band of the protein of the same molecular weight as that of F(ab')$_2$ fragment of the antibody trastuzumab was significantly improved in the YDK010ΔPBP 1a strain compared with that observed for the parent strain YDK010 (FIG. 6).

Example 5

Secretory Expression of Fc Fragment of Antibody Trastuzumab Using *Corynebacterium glutamicum* Made Deficient in Penicillin-Binding Protein PBP 1a (1) Construction of Plasmid for Secretory Expression of Fc Fragment of Antibody Trastuzumab The Fc region of the H chain of trastuzumab was amplified by PCR using the DNA shown as SEQ ID NO: 45 containing the full length H chain region of trastuzumab, which was synthesized in Example 2 (1), as a template, and separately synthesized DNAs shown as SEQ ID NOS: 77 and 78, and SEQ ID NOS: 77 and 79 as primers thereby to obtain DNA fragments of about 0.7 kbp each. Then, by using pPKSPTG1 described in WO01/23591 (containing a promoter region derived from the *C. glutamicum* ATCC 13869 strain and a signal peptide region derived from the *C. ammoniagenes* (*C. stationis*) ATCC 6872 strain) as a template and the primers shown as SEQ ID NOS: 46 and 80, a region including the aforementioned promoter region and the aforementioned signal peptide region was amplified by PCR thereby to obtain a DNA fragment of about 0.7 kbp. Then, by PCR using both the amplified DNA fragments (each of the fragments including the Fc region of the H chain region of trastuzumab and the fragment including the promoter region and the signal peptide region) as a template and DNAs shown as SEQ ID NOS: 46 and 77 as primers, DNA fragments of about 1.4 kbp each consisting of both the DNA fragments fused to each other were obtained. In the primers of SEQ ID NOS: 46 and 77, a recognition sequence for the restriction enzyme Kpn I was designed. For PCR, Pyrobest DNA Polymerase (produced by Takara Bio) was used, and the reaction conditions were those of the protocol recommended by the manufacturer. These DNA fragments were treated with the restriction enzyme Kpn I, and then each inserted into the Kpn I site of pPK4 described in Japanese Patent Laid-open (Kokai) No. 9-322774 to obtain plasmids enabling secretory expression of the Fc region of the H chain region of trastuzumab, pPKStrast-Fc(H224D-450) and pPKStrast-Fc (H231P-450). Specifically, with these plasmids, an amino acid sequence of the H chain of trastuzumab from the 224th or 231st amino acid residue to the 450th amino acid residue can be expressed (numbers of expressible amino acid residues are included in the plasmid names). By determining the nucleotide sequences of the inserted fragments, it was confirmed that expected genes were constructed. The nucleotide sequences were determined by using BigDye® Terminator v3.1 Cycle Sequencing Kit (produced by Applied Biosystems), and 3130 Genetic Analyzer (produced by Applied Biosystems).

Figure 7:
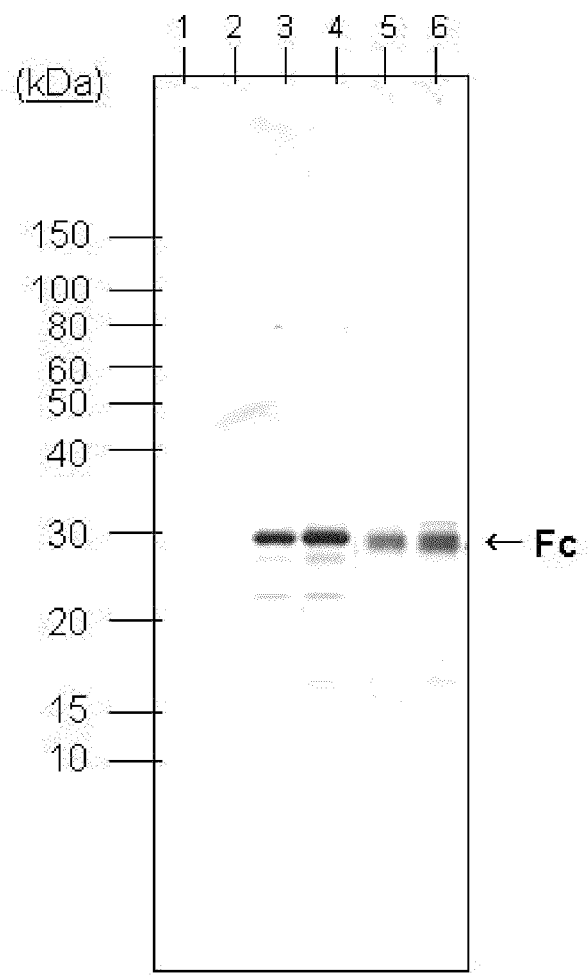
FIG. 7 is a photograph showing the results of Western blotting of the Fc fragment of trastuzumab expressed in the YDK010 strain (parent strain) and the YDK010ΔPBP1a strain.

(2) Secretory Expression of Fc Fragment of Antibody Trastuzumab Using Penicillin-Binding Protein PBP1a-Deficient Strain By using the plasmids for secretory expression of the Fc fragment of the antibody trastuzumab constructed in Example 5 (1), pPKStrast-Fc(H224D-450) and pPKStrast-Fc (H231P-450), each of the YDK010 strain and the YDK010ΔPBP1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate in a volume of 1 L with water, adjusted to pH 7.0) containing 25 mg/l of kanamycin at 30° C. for 72 hours. After completion of the culture, culture supernatant obtained by centrifuging each culture broth was subjected to reduced SDS-PAGE, and then proteins were transferred onto a PVDF membrane by using iBlot® Gel Transfer Stacks PVDF, Mini (produced by Invitrogen) and iBlot™ Gel Transfer System (produced by Invitrogen). Western blotting was performed for this PVDF membrane by using an alkaline phosphatase-labeled anti-human IgG [H&L] antibody (produced by ROCKLAND) and Alkaline Phosphatase Conjugate Substrate Kit (produced by Bio-Rad) to compare secretion amounts of the Fc fragment of the antibody trastuzumab. As a result, even when any of the secretory expression plasmids was used, the secretion amount of the Fc fragment of the antibody trastuzumab was significantly improved in the YDK010ΔPBP1a strain compared with that observed for the parent strain YDK010 (FIG. 7).

Example 6

Figure 8:
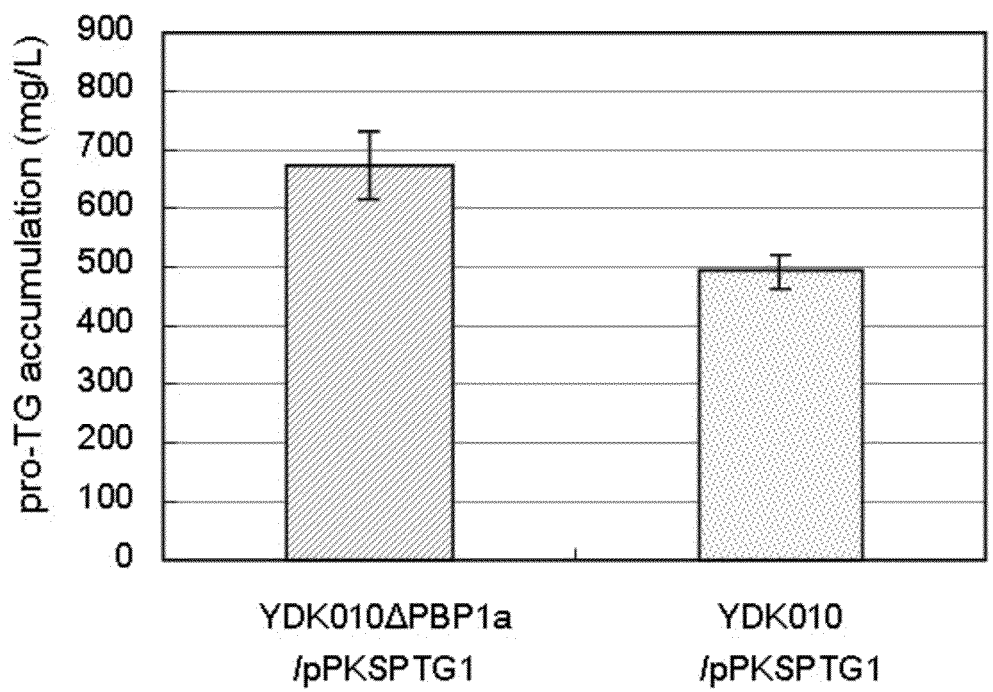
FIG. 8 is a graph showing the expression amount of a protransglutaminase expressed in the YDK010 strain (parent strain) and the YDK010ΔPBP1a strain.

Secretory Expression of Protransglutaminase Using Corynebacterium Glutamicum Made Deficient in Penicillin-Binding Protein PBP1a (1) Secretory Expression of Protransglutaminase Using Penicillin-Binding Protein PBP1a-Deficient Strain The secretory expression system of the protransglutaminase using C. glutamicum has already been reported (WO01/23591). Then, by using the plasmid vector pPKSPTG1 for secretory expression of protransglutaminase described in WO01/23591, each of the YDK010 strain and the YDK010ΔPBP1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate in a volume of 1 L with water, adjusted to pH 7.0) containing 25 mg/l of kanamycin at 30° C. for 72 hours. After completion of the culture, culture supernatant obtained by centrifuging each culture broth was subjected to reduced SDS-PAGE, and then stained with CBB R250 (produced by Bio-Rad). Secretion amounts of the protransglutaminase were determined according to the previous report (Protein Expr. Purif., 26:329-335), and the amounts were compared. As a result, the secretion amount of the protransglutaminase was significantly improved in the YDK010ΔPBP1a strain compared with that observed for the parent strain YDK010 (FIG. 8).

Example 7

Secretory Expression of Anti-Digoxin Single-Chain Antibody (scFv) Using Corynebacterium glutamicum Made Deficient in Penicillin-Binding Protein PBP1a (1) Construction of Plasmid for Secretory Expression of Anti-Digoxin Single-Chain Antibody (scFv)

The gene sequence of the anti-digoxin scFv has already been determined and the expression thereof using Bacillus subtilis has been explored (Biotechnology (N Y)., 11(1): 71-76 (1993)). With reference to this sequence, a DNA fragment shown in SEQ ID NO: 88 comprising the promoter derived from the PS2 gene of the C. glutamicum ATCC 13869 strain, a DNA coding for the signal peptide derived from SlpA of the C. ammoniagenes (C. stationis) ATCC 6872 strain expressibly ligated downstream from the promoter, and a DNA coding for the anti-digoxin scFv ligated so that the protein is expressed as a fusion protein with the above signal peptide was totally synthesized. The synthesized DNA of SEQ ID NO: 88 comprises the recognition sites of the restriction enzyme Xba I at 5' terminus and 3' terminus. The DNA coding for the anti-digoxin scFv in the synthesized DNA was designed in view of the codon usage frequency of C. glutamicum. The nucleotide sequence of the DNA coding for the anti-digoxin scFv in the synthesized DNA was shown in SEQ ID NO: 89, and the amino acid sequence of the anti-digoxin scFv was shown in SEQ ID NO: 90. The totally-synthesized DNA fragment was digested with the restriction enzyme Xba I, and inserted into the Xba I site of pPK4 described in JP9-322774A, thereby to obtain a plasmid enabling expression of the anti-digoxin scFv, pPKSSCA1.

Figure 9:
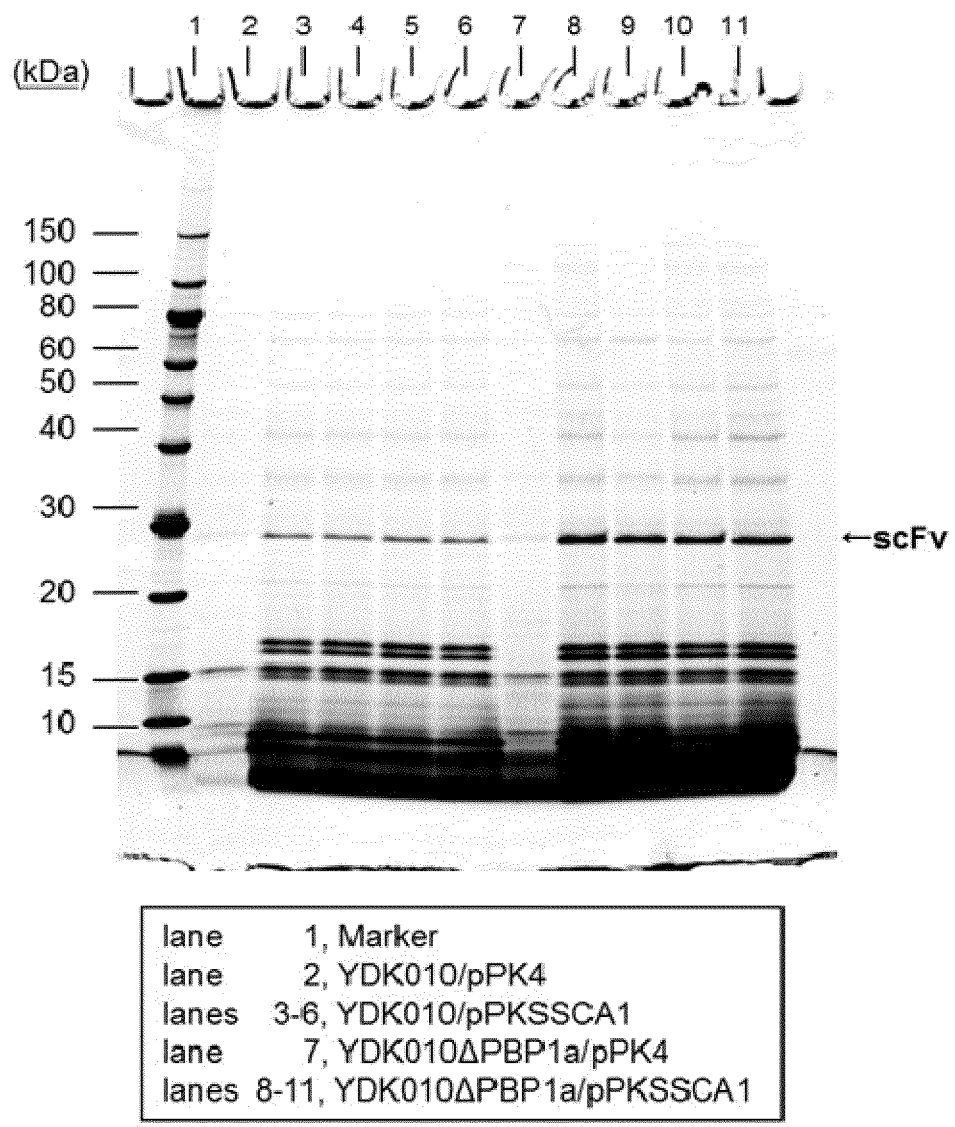
FIG. 9 is a photograph showing the results of reduced SDS-PAGE of an anti-digoxin single-chain antibody expressed in the YDK010 strain (parent strain) and the YDK010ΔPBP1a strain.

(2) Secretory Expression of Anti-Digoxin Single-Chain Antibody (scFv) Using Penicillin-Binding Protein PBP1a-Deficient Strain By using the plasmid for secretory expression of the anti-digoxin scFv constructed in Example 7 (1), pPKSSCA1, each of the YDK010 strain and the YDK010ΔPBP 1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate in a volume of 1 L with water, adjusted to pH 7.0) containing 25 mg/l of kanamycin at 30° C. for 72 hours. After completion of the culture, culture supernatant obtained by centrifuging each culture broth was subjected to reduced SDS-PAGE, and then stained with SYPRO Orange (produced by Invitrogen). As a result, a band of a protein of the same molecular weight as that of the objective anti-digoxin scFv was detected for the YDK010ΔPBP1a strain with a band strength higher than at least twice the strength observed for the parent strain YDK010 (FIG. 9). When the N-terminus sequence of the protein of this band was determined by using a protein sequencer PPSQ-21A (produced by Shimadzu), the sequence agreed with the N-terminus sequence of the objective anti-digoxin scFv, and therefore secretory expression of the anti-digoxin scFv in the culture supernatant could be confirmed.

Example 8

Secretory Expression of Fab(H&L) Fragment of Antibody Adalimumab Using *Corynebacterium glutamicum* Made Deficient in Penicillin-Binding Protein PBP1a (1) Construction of Plasmid for Secretory Expression of Fab(H&L) Fragment of Antibody Adalimumab The amino acid sequence of the tumor necrosis factor-α (TNF-α) specific antibody, adalimumab, has already been determined (Assessment Report on Feb. 14, 2008, Pharmaceuticals and Medical Devices Agency). With reference to this sequence, a DNA fragment shown in SEQ ID NO: 91 that includes the promoter derived from the PS2 gene of the *C. glutamicum* ATCC 13869 strain, a DNA coding for the signal peptide derived from SlpA of the *C. ammoniagenes* (*C. stationis*) ATCC 6872 strain expressibly ligated downstream from the promoter, and a DNA coding for the amino acid sequence from position 1 to Cys residue at position 230 of the H chain of adalimumab ligated so that the protein is expressed as a fusion protein with the above signal peptide, and further includes in the downstream thereof the promoter derived from the PS2 gene of the *C. glutamicum* ATCC 13869 strain, a DNA coding for the signal peptide derived from SlpA of the *C. ammoniagenes* (*C. stationis*) ATCC 6872 strain expressibly ligated downstream from the promoter, and a DNA coding for the L chain of adalimumab ligated so that the protein is expressed as a fusion protein with the above signal peptide was totally synthesized. Similarly, a DNA fragment shown in SEQ ID NO: 92 that includes the promoter derived from the PS2 gene of the *C. glutamicum* ATCC 13869 strain, a DNA coding for the signal peptide derived from SlpA of the *C. ammoniagenes* (*C. stationis*) ATCC 6872 strain expressibly ligated downstream from the promoter, and a DNA coding for the L chain of adalimumab ligated so that the protein is expressed as a fusion protein with the above signal peptide, and further includes in the downstream thereof the promoter derived from the PS2 gene of the *C. glutamicum* ATCC 13869 strain, a DNA coding for the signal peptide derived from SlpA of the *C. ammoniagenes* (*C. stationis*) ATCC 6872 strain expressibly ligated downstream from the promoter, and a DNA coding for the amino acid sequence from position 1 to Cys residue at position 230 of the H chain of adalimumab ligated so that the protein is expressed as a fusion protein with the above signal peptide was totally synthesized. Each of the synthesized DNAs of SEQ ID NOS: 91 and 92 comprises the recognition site of the restriction enzyme BamH I at 5' terminus and the recognition site of the restriction enzyme Xba I at 3' terminus. The DNAs coding for the H chain and the L chain of adalimumab in the synthesized DNAs were designed in view of the codon usage frequency of *C. glutamicum*. The nucleotide sequence of the DNA coding for the amino acid sequence from position 1 to position 230 of the H chain of adalimumab in the synthesized DNA was shown in SEQ ID NO: 93, and the amino acid sequence was shown in SEQ ID NO: 94. Also, the nucleotide sequence of the DNA coding for the L chain of adalimumab in the synthesized DNA was shown in SEQ ID NO: 95, and the amino acid sequence of the L chain of adalimumab was shown in SEQ ID NO: 96. Each of the totally-synthesized DNA fragments of about 2.7 kbp was digested with the restriction enzymes BamH I and Xba I, and inserted into the BamH I-Xba I site of pPK4 described in JP9-322774A, thereby to obtain plasmids enabling coexpression of the H chain (1-230C) and the L chain of adalimumab, pPKSada-FabHL and pPKSada-FabLH. "FabHL" and "FabLH" in the names of the respective plasmids indicate the incorporation order of the H chain gene and the L chain gene of adalimumab in the expression plasmids.

Figure 10:
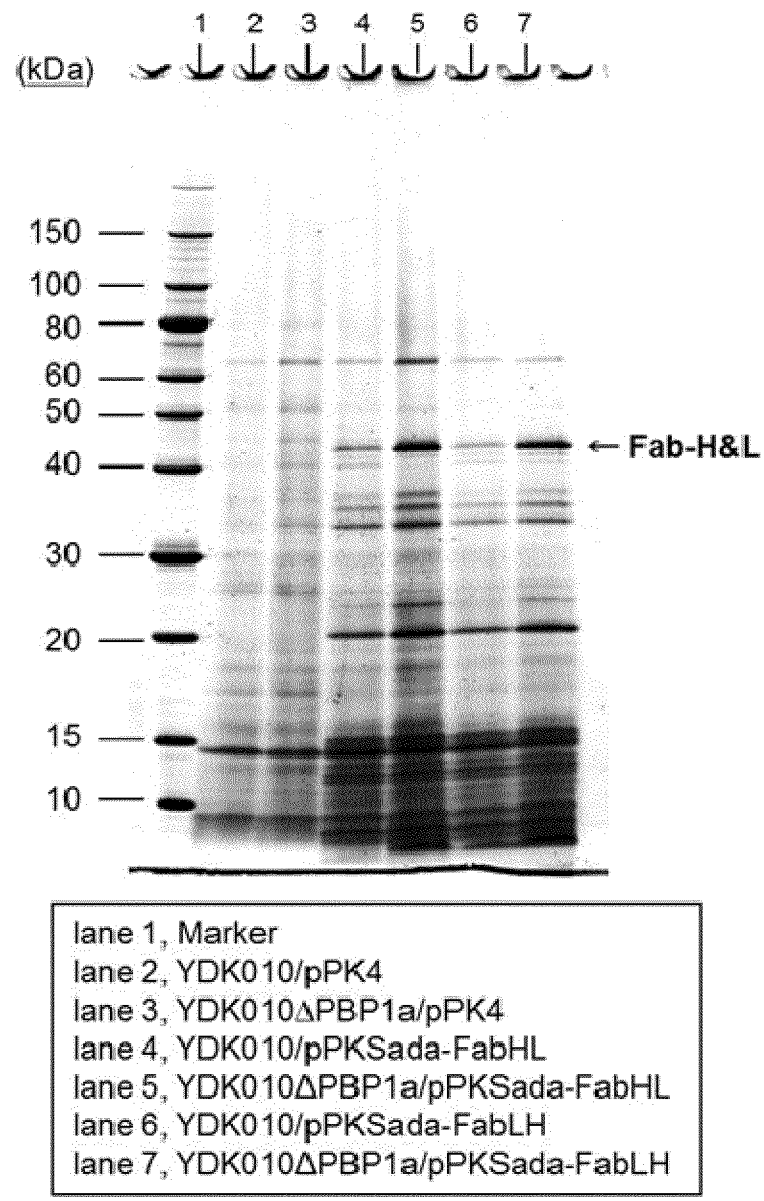
FIG. 10 is a photograph showing the results of non-reduced SDS-PAGE of the Fab(H&L) fragment of adalimumab expressed in the YDK010 strain (parent strain) and the YDK010ΔPBP1a strain.

(2) Secretory Expression of Fab(H&L) Fragment of Antibody Adalimumab Using Penicillin-Binding Protein PBP1a Deficient Strain By using the plasmids for secretory expression of the Fab (H&L) fragment of the antibody adalimumab constructed in Example 8 (1), pPKSada-FabHL and pPKSada-FabLH, each of the YDK010 strain and the YDK010ΔPBP1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 μg of thiamine hydrochloride, 450 μg of biotin, 0.15 g of DL-methionine, and 50 g of calcium carbonate in a volume of 1 L with water, adjusted to pH 7.0) containing 25 mg/l of kanamycin at 30° C. for 96 hours. After completion of the culture, culture supernatant obtained by centrifuging each culture broth was subjected to non-reduced SDS-PAGE, and then stained with SYPRO Orange (produced by Invitrogen), and secretion amounts of the Fab(H&L) fragments of the antibody adalimumab were compared. As a result, even when any of the secretory expression plasmids was used, the secretion amount of the Fab(H&L) fragment of the antibody adalimumab was significantly improved in the YDK010ΔPBP1a strain compared with that observed for the parent strain YDK010 (FIG. 10). When the N-terminus sequence of the Fab(H&L) protein in the band detected for the transformant obtained from the YDK010ΔPBP1a strain using pPKSada-FabHL was determined with a protein sequencer PPSQ-21A (produced by Shimadzu), both sequences of the N-terminus sequence of the H chain and the N-terminus sequences of the L chain of the Fab fragment of the objective antibody adalimumab were included, and therefore it could be confirmed that the Fab(H&L) fragments of the antibody adalimumab were expressed and secreted to form aggregates in the culture supernatant. Accordingly, it was revealed that the secretion amount of an antibody Fab(H&L) fragment could be improved by using a penicillin-binding protein PBP1a deficient strain in the case of expressing the Fab(H&L) fragment of adalimumab as well as in the case of expressing the Fab (H&L) fragment of trastuzumab.

Example 9

Construction of Penicillin-Binding Protein PBP1a Deficient Strain of *Corynebacterium glutamicum* ATCC13869 and Secretory Expression of Fab(H&L) Fragment of Antibody Trastuzumab (1) Construction of *C. glutamicum* ATCC13869ΔPBP1a The *C. glutamicum* ATCC13869 strain was transformed with pBSΔCgl0278, the vector for deleting the gene of the penicillin-binding protein PBP1a constructed in Example 1 (1). Strains were selected from the obtained transformants according to the method described in WO2005/113744 to obtain ATCC13869ΔPBP1a strain deficient in the Cgl0278 gene.

(2) Secretory Expression of Fab(H&L) Fragment of Antibody Trastuzumab by *C. glutamicum* ATCC13869ΔPBP1a By using the plasmid for secretory expression of the Fab (H&L) fragment of the antibody trastuzumab constructed in Example 4 (1), pPKStrast-FabH(1-229C)+L, each of the ATCC13869 strain and the ATCC13869ΔPBP1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate in a volume of 1 L with water, adjusted to pH 7.0) containing 25 mg/l of kanamycin at 30° C. for 96 hours. After completion of the culture, culture supernatant obtained by centrifuging each culture broth was subjected to non-reduced SDS-PAGE, and then stained with SYPRO Orange (produced by Invitrogen), and secretion amounts of the Fab(H&L) fragments of the antibody trastuzumab were compared. As a result, in contrast to the case of using the YDK010 strain as the expression host, the secretion amount of the Fab(H&L) fragment of the antibody trastuzumab was not improved even by using a penicillin-binding protein PBP1a deficient strain in the case of using the ATCC13869 strain as the expression host (lanes 3 and 5 of FIG. 11).

Example 10

Construction of Cell Surface Layer Protein CspB and Penicillin-Binding Protein PBP1a Double-Deficient Strain of Corynebacterium glutamicum ATCC13869 and Secretory Expression of Fab(H&L) Fragment of Antibody Trastuzumab The C. glutamicum YDK010 strain, of which the secretion amount of a protein was improved due to the deficiency of the penicillin-binding protein PBP1a, is a cell surface layer protein PS2 (CspB) deficient strain of the C. glutamicum AJ12036 strain (FERM BP-734) (WO2004/029254). Thus, a CspB deficient strain of ATCC13869 and a CspB and PBP1a double-deficient strain of ATCC13869 were constructed, and secretory expressions of Fab(H&L) fragment of the antibody trastuzumab were performed. The nucleotide sequence of the gene coding for the CspB of the ATCC 13869 strain was shown in SEQ ID NO: 97, and the amino acid sequence of the CspB of the ATCC13869 strain was shown in SEQ ID NO: 98.

(1) Construction of C. glutamicum ATCC13869ΔCspB and ATCC13869ΔCspBΔPBP1a

By PCR using the chromosomal DNA of the C. glutamicum YDK010 strain prepared in a conventional manner (method of Saito and Miura [Biochim Biophys. Acta, 72, 619 (1963)]) as a template, and the DNAs of SEQ ID NOS: 99 and 100 as primers, a DNA fragment of about 2.0 kbp that includes the region of which the gene coding for the CspB had been made deficient was amplified. For PCR, Pyrobest DNA Polymerase (produced by Takara Bio) was used, and the reaction conditions were those of the protocol recommended by the manufacturer. This DNA fragment was inserted into the Sma I site of pBS5T described in WO2006/057450 to obtain a vector pBS5T-ΔcspB for deleting the cspB gene.

Then, the C. glutamicum ATCC13869 strain was transformed with the constructed pBS5T-ΔcspB. Strains were selected from the obtained transformants according to the method described in WO2006/057450 to obtain ATCC13869ΔCspB strain deficient in the cspB gene.

Then, the C. glutamicum ATCC13869ΔCspB strain was transformed with pBSΔCgl0278, the vector for deleting the gene of the penicillin-binding protein PBP1a constructed in Example 1 (1). Strains were selected from the obtained transformants according to the method described in WO2005/113744 to obtain ATCC13869ΔCspBΔPBP1a strain deficient in both of the cspB gene and the Cgl0278 gene.

Figure 11:
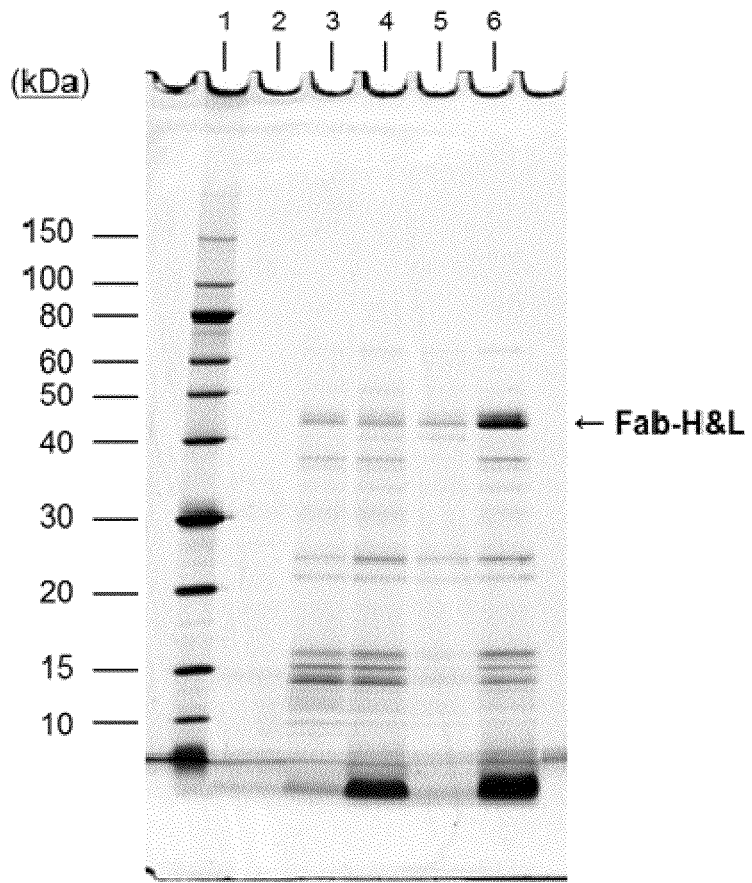
FIG. 11 is a photograph showing the results of non-reduced SDS-PAGE of the Fab(H&L) fragment of trastuzumab expressed in the ATCC 13869 strain (parent strain), the ATCC13869ΔCspB strain, the ATCC13869ΔPBP1a strain, and the ATCC13869ΔCspBΔPBP1a strain.

(2) Secretory Expression of Fab(H&L) Fragment of Antibody Trastuzumab by ATCC13869ΔCspB and ATCC13869ΔCspBΔPBP1a By using the plasmid for secretory expression of the Fab (H&L) fragment of the antibody trastuzumab constructed in Example 4 (1), pPKStrast-FabH(1-229C)+L, each of the ATCC13869ΔCspB strain and the ATCC13869ΔCspBΔPBP1a strain was transformed. Each of the obtained transformants was cultured in the MM liquid medium (120 g of glucose, 3 g of magnesium sulfate heptahydrate, 30 g of ammonium sulfate, 1.5 g of potassium dihydrogenphosphate, 0.03 g of iron sulfate heptahydrate, 0.03 g of manganese sulfate pentahydrate, 450 µg of thiamine hydrochloride, 450 µg of biotin, 0.15 g of DL-methionine, and 50 g of calcium carbonate in a volume of 1 L with water, adjusted to pH 7.0) containing 25 mg/l of kanamycin at 30° C. for 96 hours. After completion of the culture, culture supernatant obtained by centrifuging each culture broth was subjected to non-reduced SDS-PAGE, and then stained with SYPRO Orange (produced by Invitrogen), and secretion amounts of the Fab(H&L) fragments of the antibody trastuzumab were compared. As a result, the secretion amount of the Fab(H&L) fragment of the antibody trastuzumab was not improved in either the ATCC13869ΔCspB strain or the ATCC13869ΔPBP1a strain, which is a single deficient strain of the CspB or the PBP1a, compared with that observed for the parent strain ATCC 13869, however, the secretion amount of the Fab(H&L) fragment of the antibody trastuzumab was significantly improved in the ATCC13869ΔCspBΔPBP1a strain, which is a double-deficient strain (FIG. 11). Accordingly, it was revealed that the secretion amount of an antibody Fab(H&L) fragment could be improved by using a double-deficient strain of the cell surface layer protein CspB and penicillin-binding protein PBP1a.

Industrial Applicability

According to the present invention, a coryneform bacterium that can efficiently produce a heterologous protein by secretory production can be provided. Further, by using the coryneform bacterium provided by the present invention as an expression host, heterologous proteins such as industrially useful proteins can be efficiently produced by secretory production.

While the invention has been described in detail with reference to preferred embodiments thereof, it will be apparent to one skilled in the art that various changes can be made, an equivalents employed, without departing from the scope of the invention. Each of the aforementioned documents is incorporated by reference herein in its entirety.

Explanation of Sequence Listing

SEQ ID NOS: 01-08: primers
SEQ ID NOS: 09-42: nucleotide sequences of DNAs for total synthesis of H chain of trastuzumab
SEQ ID NOS: 43 and 44: primers
SEQ ID NO: 45: nucleotide sequence of gene coding for H chain of trastuzumab
SEQ ID NOS: 46-54: primers
SEQ ID NOS: 55-70: nucleotide sequences of DNAs for total synthesis of L chain of trastuzumab
SEQ ID NOS: 71 and 72: primers
SEQ ID NO: 73: nucleotide sequence of gene coding for L chain of trastuzumab
SEQ ID NOS: 74-80: primers
SEQ ID NO: 81: nucleotide sequence of Cgl0278 gene of C. glutamicum ATCC13032
SEQ ID NO: 82: amino acid sequence of protein encoded by Cgl0278 gene of C. glutamicum ATCC13032

SEQ ID NO: 83: amino acid sequence of signal peptide of PS1 of *C. glutamicum*
SEQ ID NO: 84: amino acid sequence of signal peptide of PS2 (CspB) of *C. glutamicum*
SEQ ID NO: 85: amino acid sequence of signal peptide of SlpA (CspA) of *C. ammoniagenes* (*C. stationis*)
SEQ ID NO: 86: amino acid sequence of H chain of trastuzumab
SEQ ID NO: 87: amino acid sequence of L chain of trastuzumab
SEQ ID NO: 88: nucleotide sequence of totally-synthesized DNA for expression of anti-digoxin single-chain antibody
SEQ ID NO: 89: nucleotide sequence of gene coding for anti-digoxin single-chain antibody
SEQ ID NO: 90: amino acid sequence of anti-digoxin single-chain antibody
SEQ ID NOS: 91 and 92: nucleotide sequences of totally-synthesized DNAs for expression of Fab(H&L) fragments of adalimumab
SEQ ID NO: 93: nucleotide sequence of gene coding for H chain of adalimumab (coding region of 1-230C)
SEQ ID NO: 94: amino acid sequence of H chain of adalimumab (1-230C)
SEQ ID NO: 95: nucleotide sequence of gene coding for L chain of adalimumab
SEQ ID NO: 96: amino acid sequence of L chain of adalimumab
SEQ ID NO: 97: nucleotide sequence of cspB gene of *C. glutamicum* ATCC 13869
SEQ ID NO: 98: amino acid sequence of protein encoded by cspB gene of *C. glutamicum* ATCC13869
SEQ ID NOS: 99 and 100: primers

---

The invention claimed is:

1. A coryneform bacterium having an ability to produce a heterologous protein by secretory production, wherein said bacterium is modified to have reduced activities of a penicillin-binding protein and a cell surface layer protein, and wherein the penicillin-binding protein is a PBP1a protein selected from the group consisting of:
(A) a protein comprising the amino acid sequence of SEQ ID NO: 82,
(B) a protein comprising an amino acid sequence of SEQ ID NO: 82, but which includes substitution, deletion, insertion, or addition of 1 to 10 amino acid residues, and wherein said protein has a property that if the protein activity is reduced in the coryneform bacterium, the amount of the heterologous protein produced by secretory production is increased compared with that observed for a non-modified strain; and
wherein the cell surface layer protein is a CspB protein selected from the group consisting of:
(A) a protein comprising the amino acid sequence of SEQ ID NO: 98,
(B) a protein comprising an amino acid sequence of SEQ ID NO: 98, but includes substitution, deletion, insertion, or addition of 1 to 10 amino acid residues, and wherein said protein has a property that if the protein activity is reduced in the coryneform bacterium, the amount of the heterologous protein produced by secretory production is increased compared with that observed for a non-modified strain.

2. The coryneform bacterium according to claim 1, which belongs to the genus *Corynebacterium* or *Brevibacterium*.

3. The coryneform bacterium according to claim 1, which is *Corynebacterium glutamicum*.

4. The coryneform bacterium according to claim 1,
wherein the coryneform bacterium has a genetic construct for secretory expression of the heterologous protein, and
wherein the genetic construct comprises a promoter sequence that functions in the coryneform bacterium, a nucleic acid sequence coding for a signal peptide that functions in the coryneform bacterium, which is ligated downstream from the promoter sequence, and a nucleic acid sequence coding for the heterologous protein, which is ligated downstream from the nucleic acid sequence coding for the signal peptide.

5. The coryneform bacterium according to claim 1, wherein the heterologous protein is an antibody-related molecule.

6. The coryneform bacterium according to claim 5, wherein the antibody-related molecule is selected from the group consisting of Fab, F(ab')$_2$, an Fc-fusion protein, scFv, and combinations thereof.

7. A method for producing a heterologous protein, which comprises culturing the coryneform bacterium according to claim 1 and collecting the heterologous protein produced by secretory production.

* * * * *